US007947468B2

(12) United States Patent
Alessi et al.

(10) Patent No.: US 7,947,468 B2
(45) Date of Patent: May 24, 2011

(54) METHODS

(75) Inventors: Dario Alessi, Dundee (GB); R. Jeremy Nichols, Dundee (GB)

(73) Assignee: Medical Research Council, London (GB)

( * ) Notice: Subject to any disclaimer, the term of this patent is extended or adjusted under 35 U.S.C. 154(b) by 463 days.

(21) Appl. No.: 12/244,715

(22) Filed: Oct. 2, 2008

(65) Prior Publication Data

US 2009/0142784 A1 Jun. 4, 2009

Related U.S. Application Data

(63) Continuation-in-part of application No. PCT/GB2008/001211, filed on Apr. 7, 2008.

(60) Provisional application No. 60/910,242, filed on Apr. 5, 2007.

(30) Foreign Application Priority Data

Apr. 5, 2007 (GB) .................................. 0706709.3

(51) Int. Cl.
*C12Q 1/48* (2006.01)
(52) U.S. Cl. ......................................................... 435/15
(58) Field of Classification Search ...................... 435/15
See application file for complete search history.

(56) References Cited

U.S. PATENT DOCUMENTS

| 2003/0166222 A1 | 9/2003 | Meyers |
| 2004/0265849 A1 | 12/2004 | Cargill et al. |

FOREIGN PATENT DOCUMENTS

| WO | 2004074485 A | 9/2004 |
| WO | 2007104763 A1 | 9/2007 |
| WO | 2008091799 A2 | 7/2008 |
| WO | 2008122789 A2 | 10/2008 |

OTHER PUBLICATIONS

Marin, The Parkinson Disease Gene LRRK2: Evolutionary and Structural Insights, Mol. Biol. Evol., 2006, 2423-2433, 23(12), Oxford University Press on behalf of the Society for Molecular Biology and Evolution.
Goldberg et al, Identification of four candidate cGMP targets in Dictyostelium, PNAS, 2002, 6749-6754, vol. 99, No. 10, Boston Biomedical Research Institute.
West et al, Parkinson's disease-associated mutations in leucine-rich repeat kinase 2 augment kinase activity, PNAS, 2005, 16842-19847, vol. 102, No. 46, Institute for Cell Engineering, Departments of Neurology, Neuroscience, and Physiology.
Bosgraaf et al, A novel cGMP signalling pathway mediating myosin phosphorylation and chemotaxis in Dictyostelium, The EMBO Journal, 2002, 4560-4570, vol. 21, No. 17, Department of Biochemistry, University of Groningen.
Tran Quang et al, Ezrin function is required for ROCK-mediated fibroblast transformation by the Net and Dbl oncogenes, The EMBO Journal, 2000, 4565-4576, vol. 19, No. 17, Imperial Cancer Research Fund Laboratories.
Cohen et al, Kestrel: a powerful method for identifying the physiological substrates of protein kinases, Biochemical Journal, 2006, 1-6, 393, MRC protein Phosphorylation Unit.
Gary et al, Ezrin Self-Association Involves Binding of an N-Terminal Domain to a Normally Masked C-Terminal Domain that Includes the F-Actin Binding Site, Molecular Biology of the Cell, 1995, 1061-1075, vol. 6, The American Society for Cell Biology.
Pestonjamasp et al, Moesin, Ezrin, and p205 Are Actin-binding Proteins Associated with Neurophil Plasma Membranes, Molecular Biology of the Cell, 1995, 247-259, vol. 6, The American Society for Cell Biology.
Nakamura et al, Regulation of F-Actin Binding to Platelet Moesin in Vitro by Both Phosphorylation of Threonine 558 and Polyphosphatidylinositides, Molecular Biology of the Cell, 1999, 2669-2685, vol. 10, The American Society for Cell Biology.
Turunen et al, Ezrin Has a COOH-Terminal Actin-binding Site That is Conserved in the Ezrin Protein Family, The Journal of Cell Biology, 1994, 1445-1453, vol. 126, No. 6, The Rockefeller University Press.
Matsui et al, Rho-Kinase Phosphorylates COOH-terminal Threonines of Ezrin/Radixin/Moesin (ERM) Proteins and Regulates Their Head-to-Tail Association, The Journal of Cell Biology, 1998, 647-657, vol. 140, No. 3, The Rockefeller University Press.
Paglini et al, Suppression of Radixin and Moesin Alters Growth Cone Morphology, Motility, and process Formation in Primary Cultured Neurons, The Journal of Cell Biology, 1998, 443-455, vol. 143, No. 2, The Rockefeller University Press.
Huang et al, Replacement of Threonine 558, a Critical Site of Phosphorylation of Moesin in Vivo, with Aspartate Activates F-actin Binding of Moesin, The Journal of Biological Chemistry, 1999, 12803-12810, vol. 274, No. 18, The American Society for Biochemistry and Molecular Biology, Inc.
Oshiro et al, Phosphorylation of Moesin by Rho-associated Kinase (Rho-kinase) Plays a Crucial Role in the Formation of Microvilli-like Structures, The Journal of Biological Chemistry, 1998, 34663-34666, vol. 273, No. 52, The American Society for Biochemistry and Molecular Biology, Inc.
McClatchey et al, Membraine organization and tumorigenesis—the NF2 tumor suppressor, Merlin, Genes & Development, 2005, 2265-2277, 19, Massachusetts General Hospital, Center for Cancer Research and Harvard Medical School, Department of Pathology, Charlestown.
West et al, Parkinson's disease-associated mutations in LRRK2 link enhanced GTP-bindind and kinase activities to neuronal toxicity, Human Molecular Genetics, 2007, 223-232, vol. 16, No. 2, Oxford University Press.

(Continued)

*Primary Examiner* — Maryam Monshipouri
(74) *Attorney, Agent, or Firm* — K&L Gates LLP; Louis C. Cullman; Michelle Glasky Bergman

(57) ABSTRACT

A method for identifying a compound expected to be useful in modulating a LRRK2 protein kinase activity, the method comprising the steps of (1) determining whether a test compound modulates the protein kinase activity of a LRRK2 polypeptide on a substrate Ezrin/Radixin/moesin (ERM) family polypeptide and (2) selecting a compound which modulates the LRRK2 polypeptide protein kinase activity. Such a compound may be useful in treating Parkinson's Disease or Parkinsonism. A catalytically active fragment of LRRK2 is identified, requiring the GTPase, COR and kinase domains as well as the WD_40-like motif and C-terminal tail.

8 Claims, 30 Drawing Sheets

OTHER PUBLICATIONS

Gloeckner et al, The Parkinson disease causing LRRK2 mutation I2020T is associated with increased kinase activity, Human Molecular Genetics, 2006, 223-232, vol. 15, No. 2, Oxford University Press.

Jaleel et al, LRRK2 phosphorylates moesin at threonine-558: characterization of how Parkinson's disease mutants affect kinase activity, Biochemical Journal, 2007, 307-317, 405, Biochemical Society.

Polesello et al, Small is beautiful: what flies tell us about ERM protein function in development, Trends in Cell Biology, 2004, vol. 14, No. 6, pp. 294-302, Centre de Biologie du Developpement, France.

Taylor et al, LRRK2: a common pathway for parkinsonism, pathogenesis and prevention?, Trends in Molecular Medicine, 2006, vol. 12, No. 2, pp. 76-82, Department of Neuroscience, Mayo Clinic College of Medicine, Jacksonville.

Mata et al, LRRK2 in Parkinson's disease: protein domains and functional insights, Trends in Neuroscience, 2006, vol. 29, No. 5, pp. 286-293, Department of Neuroscience, Mayo Clinic College of Medicine, Jacksonville.

Farrer et al, LRRK2 mutations in Parkinson disease, Neurology, 2005, 738-740, 65, AAN Enterprises, Inc.

Biskup et al, Localization of LRRK2 to Membranous and Vesicular Structures in Mammalian Brain, American Neurological Association, 2006, 557-569, 60.

Pearson et al, Structure of the ERM Protein Moesin Reveals the FERM Domain Fold Masked by an Extended Actin Binding Tail Domain, Cell, 2000, 259-270, vol. 101, Cell Press.

Bretscher et al, ERM Proteins and Merlin: Integrators at the Cell Cortex, Mol. Cell. Bio., 2002, 586-599, vol. 3, Nature Publishing Group.

Bosgraaf et al, Roc, a Ras/GTPase domain in complex proteins, Science Direct, 2003, 5-10, Elsevier.

MacLeod et al, The Familial Parkinsonism Gene LRRK2 Regulates Neurite Process Morphology, Neuron, 2006, 587-593, 52, Elsevier Inc.

Troiani et al, Searching for Biomarkers of Aurora-A Kinase Activity: Identification of in Vitro Substrates through a Modified KESTREL Approach, Journal of Proteome Research, 2005, 1296-1303, 4, American Chemical Society.

Campbell et al, Identification of Protein Phosphorylation Sites by a Combination of Mass Spectrometry and Solid Phase Edman Sequencing, Journal of Biomolecular Techniques, 2002, 121-132, vol. 13, Issue 3, MRC Protein Phosphorylation Unit, University of Dundee, Scotland.

Durocher et al, High-level and high-throughput recombinant protein production by transient transfection of suspension-growing human 293-EBNA1 cells, Nucleic Acids Research, 2002, e9, vol. 30, No. 2, Oxford University Press.

Manning et al, The Protein Kinase Complement of the Human Genome, Science, 2002, 1912-1934, vol. 298.

Zabetian et al, A clinic-based study of the LRRK2 gene in Parkinson disease yields new mutations, Neurology, 2005, 741-744, 65, AAN Enterprises, Inc.

Farrer et al, LRRK2 mutations in Parkinson disease, Neurology, 738-740, 65, AAN Enterprises, Inc., 2005.

Zimprich et al, Mutations in LRRK2 Cause Autosomal-Dominant Prkinsonism with Pleomorphic Pathology, Neuron, 2004, 601-607, vol. 44, Cell Press.

Paisan-Ruiz et al, Cloning of the Gene Containing Mutations that Cause PARK8-Linked Parkinson's Disease, Neuron, 2004, 595-600, vol. 44, Cell Press.

Boudeau et al, Emerging roles of pseudokinases, Trends in Cell Biology, vol. 16, No. 9, 443-452 MRC Protein Phosphorylation Unit, School of Life Sciences, University of Dundee, United Kingdom, 2006.

Katayama S et al. "Antisense transcription in the mammalian transcriptome" Science 309:1564-1566, 2005.

```
Moesin    1   ------------------MPKTISVRVTTMDAELEFAIQPNTTGKQLFDQVVKTIGLREVW
Ezrin     1   ------------------MPKPINVRVTTMDAELEFAIQPNTTGKQLFDQVVKTIGLREVW
Radixin   1   ------------------MPKPINVRVTTMDAELEFAIQPNTTGKQLFDQVVKTVGLREVW
Merlin    1   MAGAIASRMSFSSLKRKQPKTFTVRIVTMDAEMEENCEMKWKGKDLFDLVCRTLGLRETW Moesin    44  FFGLQYQDTKGFSTWLKLNKKVTAQDVRKESPLLFKFRAKFYPEDVSEELIQDITQRLFF
Ezrin     44  YFGLHYVDNKGFPTWLKLDKKVSAQEVRKENPLQFKFRAKFYPEDVAEELIQDITQKLFF
Radixin   44  FFGLQYVDSKGYSTWLKLNKKVTQQDVKKENPLQFKFRAKFFPEDVSEELIQEITQRLFF
Merlin    61  FFGLQYT-IKDTVAWLKMDKKVLDHDVSKEEPVTHHLAKFYPENAEEELVQEITQHLFF Moesin    104 LQVKEGILNDDIYCPPETAVLLASYAVQSKYGDFNKEVHKSGYLAGDKLLPQRVLEQHKL
Ezrin     104 LQVKEGILSDEIYCPPETAVLLGSYAVQAKFGDYNKEVHKSGYLSSERLIPQRVMDQHKL
Radixin   104 LQVKEAILNDEIYCPPETAVLLASYAVQAKYGDYNKEIHKPGYLANDRLLPQRVLEQHKL
Merlin    120 LQVKKQILDEKIYCPPEASVLLASYAVQAKYGDYDPSVHKRGFLAQEELLPKRVINLYQM Moesin    164 NKDQWEERIQVWHEEHRGMLREDAVLEYLKIAQDLEMYGVNYFSIKNKKGSELWLGVDAL
Ezrin     164 TRDQWEDRIQVWHAEHRGMLKDNAMLEYLKIAQDLEMYGINYFEIKNKKGTDLWLGVDAL
Radixin   164 TKEQWEERIQNWHEEHRGMLREDSMMEYLKIAQDLEMYGVNYFEIKNKKGTELWLGVDAL
Merlin    180 TPEMWEERITAWYAEHRGRARDEAEMEYLKIAQDLEMYGVNYFAIRNKKGTELLLGVDAL Moesin    224 GLNIYEQNDRLTPKIGFPWSEIRNISFNDKKFVIKPIDKKAPDFVFYAPRLRINKRILAL
Ezrin     224 GLNIYEKDDKLTPKIGFPWSEIRNISFNDKKFVIKPIDKKAPDFVFYAPRLRINKRILQL
Radixin   224 GLNIYEHDDKLTPKIGFPWSEIRNISFNDKKFVIKPIDKKAPDFVFYAPRLRINKRILAL
Merlin    240 GLHIYDPENRLTPKISFPWNEIRNISYSDKEFTIKPLDKKIDVFKFNSSKLRVNKLILQL Moesin    284 CMGNHELYMRRRKPDTIEVQQMKAQAREEKHQKQMERAMLENEKKKREMAEKEKEKIERE
Ezrin     284 CMGNHELYMRRRKPDTIEVQQMKAQAREEKHQKQLERQQLETEKKRRETVEREKEQMRE
Radixin   284 CMGNHELYMRRRKPDTIEVQQMKAQAREEKHQKQLERAQLENEKEKRETAEKEKERIERE
Merlin    300 CIGNHDLFMRRRKADSLEVQQMKAQAREEKARKQMERQRLAREKQMREEAERTRDELER- Moesin    344 KEELMERLKQIEEQTKKAQQELEEQTRRALELEQERKRAQSEAEKLAKERQEAEEAKEAL
Ezrin     344 KEELMLRLQDYEEKTKKAERELSEQIQRALQLEEERKRAQEEAERLEADRMAALRAKEEL
Radixin   344 KEELMERLKQIEEQTIKAQKELEEQTRKALELDQERKRAKEEAERLEKERRAAEEAKSAI
Merlin    359 ------RLLQMKEEATMANEALMRSEETADLLAEKAQITEEEAKLLAQKAAEAEQEMQRI Moesin    404 LQASRDQKKTQEQLALEMAELTARISQLEMARQKKESEAVEWQQKAQMVQEDLEKTRAEL
Ezrin     404 ERQAVDQIKSQEQLAAELAEYTAKIALLEEARRRKEDEVEEWQHRAKEAQDDLVKTKEEL
Radixin   404 AKQAADQMKNQEQLAAELAEFTAKIALLEEAKKKKEEEATEWQHKAFAAQEDLEKTKEEL
Merlin    413 KATAIRTEEEKRLMEQKVLEAEVLALKMAEESERRAKEADQLKQDLQEAREAERRAKQKL Moesin    464 KTAMSTP------HVAEPAENEQDEQDENGAEAS----ADIRADAMAKDRSEEERTTEAEK
Ezrin     464 HLVMTAPPPPPPPVYEPVSYHVQESLQDEGAEPTGYSAELSSEGIRDDRNEEKRITEAEK
Radixin   464 KTVMSAPPPPPPPPVIPPTENEHDEHDENNAEAS----AELSNEGVMNHRSEEERVTETQK
Merlin    473 LETATKPTYPPMNPIPAPLPPDIPSFNLIGDSLS-EDFKDTDMKRTSMEIEKEKVEYMEK Moesin    515 NERVQKHLKALTSELANARDESKKTANDMIHAEN-MRLGRDKYKTLRQIRQGNTKQRIDE
Ezrin     524 NERVQRQLVTLSSELSQARDENKRTHNDIIHNEN-MRQGRDKYKTLRQIRQGNTKQRIDE
Radixin   521 NERVKKQLQALSSELAQARDETKKTQNDVLHAEN-VKAGRDKYKTLRQIRQGNTKQRIDE
Merlin    532 SKHLQEQLNELKTEIEALKLKERETALDILHNENSDRGGSSKHNTIKKLTLQSAKSRVAF Moesin    574 FESM     SEQ ID NO:39
Ezrin     583 FEAL     SEQ ID NO:40
Radixin   580 FEAM     SEQ ID NO:41
Merlin    592 FEEL     SEQ ID NO:42
```

| | | SEQ ID NO. |
|---|---|---|
| Moesin | MRLGRDKYKTLRQIRQGNTKQRIDEFESM | 43 |
| Ezrin/Villin2 | MRQGRDKYKTLRQIRQGNTKQRIDEFEAL | 44 |
| Radixin | VKAGRDKYKTLRQIRQGNTKQRIDEFEAM | 45 |
| Merlin | DRGSSKHNTIKKLTLQSAKSRVAFFEEL | 46 |

B

32P Autoradiograph / Colloidal Coomassie

Moesin / Ezrin / Radixin / C' Moesin (− +, − +, − +, − +)

Heat, Auto-P LRRK2 G/S, P-ERM, C' Mo

Markers: 150, 100, 75, 50, 37, 25

Figure 15

RLGRDKYKTLRQIRQ (short LRRKtide)  SEQ ID NO.1
vs.
RLGRDKYKTLRQIRQGNTKQR (long  SEQ ID NO.2
LRRKtide)

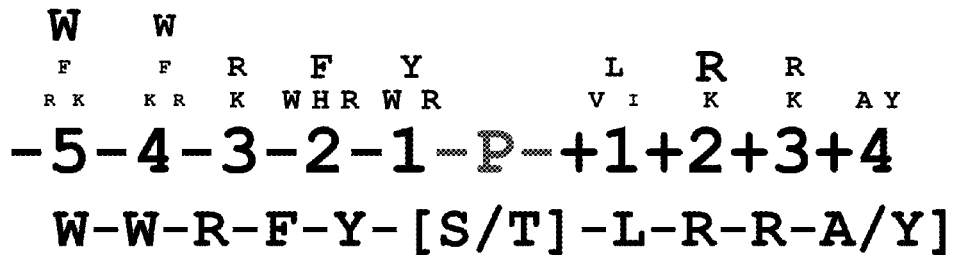
Figure 24A
| Nictide | RLGWWRFYTLRRARQGNTKQR | SEQ ID NO.51 |
| LongLRRKtide | RLGRDKYKTLRQIRQGNTKQR | SEQ ID NO.52 |
| LRRKtide | RLGRDKYKTLRQIRQ | SEQ ID NO.1 |
Figure 24B
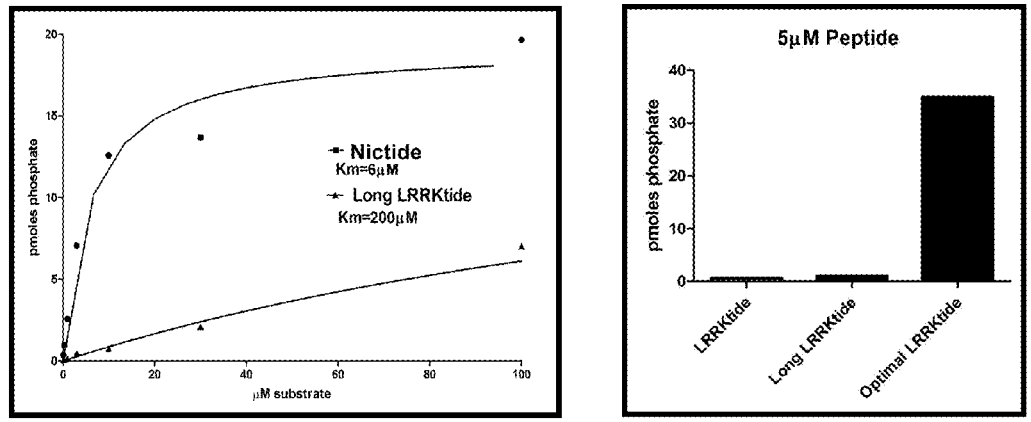
Figure 24C

GPLGSMGPQDVGNDWEVLGVHQLILKMLTVHNASVNLSVIGLK
TLDLLLTSGKITLLILDEESDIFMLIFDAMHSFPANDEVQKLG
CKALHVLFERVSEEQLTEFVENKDYMILLSALTNFKDEEEIVL
HVLHCLHSLAIPCNNVEVLMSGNVRCYNIVVEAMKAFPMSERI
QEVSCCLLHRLTLGNFFNILVLNEVHEFVVKAVQQYPENAALQ
ISALSCLALLTETIFLNQDLEEKNENQENDDEGEEDKLFWLEA
CYKALTWHRKNKHVQEAACWALNNLLMYQNSLHEKIGDEDGHF
PAHREVMLSMLMHSSSKEVFQASANALSTLLEQNVNFRKILLS
KGIHLNVLELMQKHIHSPEVAESGCKMLNHLFEGSNTSLDIMA
AVVPKILTVMKRHETSL        SEQ ID NO:66

Figure 30

METHODS

CROSS REFERENCE TO RELATED APPLICATIONS

The present application is a continuation-in-part of PCT/GB2008/001211 filed Apr. 7, 2008 which in turn claims priority to U.S. Provisional Patent Application No. 60/910,242 filed Apr. 5, 2007 and Great Britain Patent Application number 0706709.3 filed Apr. 5, 2007, the entire contents of all of which are incorporated by reference herein.

FIELD OF THE INVENTION

Disclosed herein are methods, compositions and assays related to the gene encoding for Leucine Rich Repeat protein Kinase-2 (LRRK2).

BACKGROUND OF THE INVENTION

There has been much interest raised by the recent discovery that different autosomal dominant point mutations within the gene encoding for the Leucine Rich Repeat protein Kinase-2 (LRRK2), predispose humans to develop late-onset Parkinson's disease (PD, OMIM accession number 609007), with a clinical appearance indistinguishable from idiopathic PD. The genetic analysis undertaken to date indicates that mutations in LRRK2 are relatively frequent, not only accounting for 5-10% of familial PD, but are also found in a significant proportion of sporadic PD cases. Little is known about how LRRK2 is regulated in cells, what are its physiological substrates and how mutations in LRRK2 cause or increase risk of PD. In mammals there are two isoforms of the LRRK protein kinase, LRRK1 (2038 residues) and LRRK2 (2527 residues). They belong to a protein family that has also been termed Roco. Thus far mutations in LRRK2, but not LRRK1 have been linked to PD.

The LRRK/Roco class of protein kinases was initially characterised in the slime mould *Dictyostelium discoideum*, as a protein termed GbpC (cGMP binding protein C), that comprised an unusual member of the Ras/GTPase superfamily, distinct from other small GTPase domains as it possesses other domains including a protein kinase. Subsequent studies suggested that GbpC regulates chemotaxis and cell polarity in *Dictyostelium*, but the physiological substrates for this enzyme have not been elucidated. The defining feature of the LRRK/Roco-proteins is that they possess Leucine Rich Repeat (LRR) motif, a Ras-like small GTPase, a region of high amino acid conservation that has been termed the C-terminal Of Ras of complex (COR) domain, and a protein kinase catalytic domain. The protein kinase domain of LRRK2 belongs to the tyrosine-like serine/threonine protein kinases and is most similar to the Rho-Interacting Protein kinases (RIPK), that play key roles in innate immunity signalling pathways. Other domains are also found on specific members of the LRRK kinases. For example, the GbpC possesses an additional DEP, cyclicGMP-binding and Ras-GEF domains that are not found in mammalian LRRK1 and LRRK2. Human LRRK1 possesses 3 ankyrin repeats at its N-terminus, whereas LRRK2 lacks these domains, but possesses a WD40 repeat located towards its C-terminus not found in LRRK1.

Human LRRK2 consists of leucine rich repeats (residues 1010-1287), a small GTPase domain (residues 1335-1504), a COR domain (residues 1517-1843), a serine/threonine protein kinase domain (residues 1875-2132) and a motif that has low resemblance to a WD40 repeat (2231-2276). To date approximately 20 single amino acid substitution mutations have been linked to autosomal-dominant PD, and these have been found within or in close proximity to conserved residues of the small GTPase, COR, protein kinase and WD40 domains.

The most prevalent mutant form of LRRK2 accounting for approximately 6% of familial PD and 3% of sporadic PD cases in Europe, comprises an amino acid substitution of Gly2019 located within the conserved DYG-Mg2+-binding motif, in subdomain-VII of the kinase domain, to a Ser residue. Recent reports suggest that this mutation moderately enhances, approximately 2-3-fold, the autophosphorylation of LRRK2, as well as its ability to phosphorylate myelin basic protein. These findings suggest that over-activation of LRRK2 predisposes humans to develop PD, implying that drugs which inhibited LRRK2, could be utilised to delay the onset or even treat some forms of PD. The study of LRRK2 has been hampered by the difficulty in expressing active recombinant enzyme and by the lack of a robust quantitative assay.

The listing or discussion of a prior-published document in this specification should not necessarily be taken as an acknowledgement that the document is part of the state of the art or is common general knowledge.

SUMMARY OF THE INVENTION

Compounds, and methods for identifying those compounds, are disclosed herein wherein the compounds are useful in the treatment of Parkinson's Disease.

In one embodiment, a method for identifying a compound expected to be useful in inhibiting LRRK2 protein kinase activity is provided, the method comprising the steps of: (1) determining whether a test compound inhibits the protein kinase activity of a LRRK2 polypeptide on a substrate polypeptide, and (2) selecting a compound which inhibits said LRRK2 polypeptide protein kinase activity, wherein the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52).

In another embodiment, a method for identifying a compound expected to be useful in inhibiting the phosphorylation of an ERM family polypeptide in a cell is provided, the method comprising the steps of: (1) determining whether a test compound inhibits the protein kinase activity of a LRRK2 polypeptide on a substrate polypeptide, and (2) selecting a compound which inhibits the LRRK2 polypeptide protein kinase activity, wherein the substrate polypeptide comprises the sequence (W/F/R/K)(W/F/R/K)(R/K)(F/W/H/R)(Y/W/R)(S/T)(L/V/I)(R/K)(R/K) (A/Y) (SEQ ID NO:52).

In yet another embodiment, a method for identifying a compound for treating or preventing Parkinson's Disease (PD) or Parkinsonism is provided, the method comprising the steps of: (1) determining whether a test compound inhibits the phosphorylation of a substrate polypeptide, and (2) selecting a compound which inhibits the phosphorylation of the substrate polypeptide, wherein the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52).

In one embodiment, the method comprises the steps of (1) determining whether a test compound inhibits phosphorylation of the substrate polypeptide by an LRRK2 polypeptide, and (2) selecting a compound which inhibits the phosphorylation of the substrate polypeptide by the LRRK2 polypeptide.

In another embodiment, the LRRK2 polypeptide is wild type human LRRK2 or a fragment thereof, or a fusion either thereof, such as wherein the fragment comprises at least residues 1326-2527 of wild type human LRRK2. In another embodiment, the LRRK2 polypeptide is human LRRK2 having a naturally occurring mutation of wild type human LRRK2; or a fragment thereof; or a fusion either thereof, such as wherein the fragment comprises at least residues 1326-2527 of wild type human LRRK2.

In yet another embodiment, the naturally occurring mutation of human LRRK2 is a mutation associated with Parkinson's Disease (PD), wherein the mutation, using the numbering of wild type human LRRK2, is selected from the group consisting of R1441C, R1441G, Y1699C, R1914H, I2012T, I2020T, T2356I, G2385R, K544E, P755L, R793M, Q930R, S973N, R1067Q, S1096C, I1122V, S1228T, I1371V, R1441H, A1442P, R1514Q, M1869T and G2019S.

In an embodiment, the LRRK2 polypeptide is a GST fusion polypeptide. In another embodiment, the LRRK2 polypeptide is GST-LRRK2[1326-2527, G2019S].

In another embodiment, the substrate polypeptide consists of or comprises the sequence selected from the group consisting of WWKFYTLRRA (SEQ ID NO:67), WWRFYTLRKA (SEQ ID NO:48), RLGWWKFYTLRRARQGNTKQR (SEQ ID NO:49), RLGWWRFYTLRKARQGNTKQR (SEQ ID NO:50) and RLGWWRFYTLRRARQGNTKQR (SEQ ID NO:51).

The method of any one of claims 1 to 3 wherein the substrate polypeptide is a polypeptide of 12 to 100 amino acids, wherein said substrate polypeptide comprises the amino acid sequence RLGRDKYK(T/S)LRQIRQ (SEQ ID NO:3) or RLGRDKYK(T/S)LRQIRQGNTKQR (SEQ ID NO:4), optionally including up to ten conservative or non-conservative amino acid substitutions at residues other than the T/S residue.

In another embodiment, the method comprises the step of assessing whether the compound modulates ERM family polypeptide phosphorylation in a whole cell, tissue or organism; or characteristics of Parkinsonism or Parkinson's Disease in an organism and a compound that modulates the activity or disease characteristics is selected. In another embodiment, the method further comprises the step of assessing whether the compound modulates the activity of an ERM family polypeptide in the whole cell, tissue or organism, and a compound that modulates the activity is selected.

In another embodiment, a polypeptide is provided comprising the sequence (W/F/R/K)(W/F/R/K)(R/K)(F/W/H/R)(Y/W/R)(S/T)(L/V/I)(R/K)(R/K)(A/Y) (SEQ ID NO:52). In another embodiment, the sequence is selected from the group consisting of WWKFYTLRRA (SEQ ID NO:67), WWRFYTLRKA (SEQ ID NO:48), RLGWWKFYTLRRARQGNTKQR (SEQ ID NO:49), RLGWWRFYTLRKARQGNTKQR (SEQ ID NO:50) and RLGWWRFYTLRRARQGNTKQR (SEQ ID NO:51). In another embodiment a polynucleotide is provided encoding a polypeptide comprising the sequence (W/F/R/K)(W/F/R/K)(R/K)(F/W/H/R)(Y/W/R)(S/T)(L/V/I)(R/K)(R/K)(A/Y) (SEQ ID NO:52).

In one embodiment, a method is provided for assessing LRRK2 activity in a sample, the method comprising the step of: assessing the ability of the sample to phosphorylate a substrate polypeptide as defined above.

In another embodiment, an antibody is provided capable of binding to a polypeptide consisting of residues 100 to 500 of LRRK2. In another embodiment, the antibody binds to residues 100-498 of LRRK2.

In yet another embodiment, the antibody is prepared by the process of: raising the antibody to, or selecting the antibody on the basis of binding to, a polypeptide consisting of residues 100 to 500 of LRRK2 or a fragment thereof or a fusion either thereof, wherein said fusion is not with an LRRK2-derived sequence.

In another embodiment, a method for identifying a compound expected to be useful in modulating LRRK2 protein kinase activity is provided, the method comprising the steps of (1) determining whether a test compound modulates the protein kinase activity of a LRRK2 polypeptide on a substrate Ezrin/Radixin/Moesin (ERM) family polypeptide and (2) selecting a compound which modulates the said LRRK2 polypeptide protein kinase activity.

In another embodiment, a method for identifying a compound expected to be useful in modulating, for example inhibiting, the phosphorylation of an ERM family polypeptide in a cell is provided, the method comprising the steps of (1) determining whether a test compound modulates, for example inhibits, the protein kinase activity of a LRRK2 polypeptide, and (2) selecting a compound which modulates, for example inhibits, the protein kinase activity of the LRRK2 polypeptide.

In another embodiment, a method for identifying a method for identifying a compound expected to be useful in treating or preventing Parkinson's Disease (PD) or Parkinsonism or other neurodegenerative condition is provided, the method comprising the steps of (1) determining whether a test compound modulates, for example inhibits, the phosphorylation of an ERM family (for example moesin) polypeptide, and (2) selecting a compound which modulates, for example inhibits, the phosphorylation of the ERM family (for example moesin) polypeptide.

In another embodiment, the methods comprises the steps of (1) determining whether a test compound modulates, for example inhibits, the phosphorylation of an ERM family (for example moesin) polypeptide by an LRRK2 polypeptide, and (2) selecting a compound which modulates, for example inhibits, the phosphorylation of the ERM family (for example moesin) polypeptide by the LRRK2 polypeptide.

In another embodiment, the LRRK2 polypeptide is wild type human LRRK2 or a fragment thereof, or a fusion either thereof. In yet another embodiment, the fragment comprises at least residues 1326-2527 of wild type human LRRK2. In still another embodiment, the LRRK2 polypeptide is human LRRK2 having a naturally occurring mutation of wild type human LRRK2; or a fragment thereof; or a fusion either thereof. In another embodiment, the naturally occurring mutation of human LRRK2 is a mutation associated with Parkinson's Disease (PD). In another embodiment, the mutation, using the numbering of wild type human LRRK2, is G2019S. In another embodiment, the mutation, using the numbering of wild type human LRRK2, is R1441C, R1441G, Y1699C, R1914H, I2012T, I2020T, T2356I, G2385R, K544E, P755L, R793M, Q930R, S973N, R1067Q, S1096C, I1122V, S1228T, I1371V, R1441H, A1442P, R1514Q, M1869T or G2019S. In another embodiment, the fragment corresponds to at least residues 1326-2527 of human LRRK2.

In another embodiment, the LRRK2 polypeptide is a GST fusion polypeptide. In yet another embodiment, the LRRK2 polypeptide is GST-LRRK2[1326-2527, G2019S].

In another embodiment, the LRRK2 polypeptide and/or ERM family polypeptide is recombinant.

In one embodiment, the ERM family polypeptide is a fragment derivable from an ERM family polypeptide, for example moesin, radixin or ezrin, which encompasses the residue corresponding to Thr558 residue of moesin and at least part of the surrounding sequence which includes this residue, for example at least the 2, 3, 4, 5, 6 or 7 residues C-terminal and N-terminal of this residue, for example the polypeptide RLGRDKYKTLRQIRQ (SEQ ID NO:1) or RLGRDKYKTLRQIRQGNTKQR (SEQ ID NO:3); or a polypeptide of less than 100, 80, 60, 50, 40, 30, 25, 20, 19, 18, 17 or 16 amino acids, comprising the amino acid sequence RLGRDKYK(T/S)LRQIRQ (SEQ ID NO:3) or RLGRD-KYK(T/S)LRQIRQGNTKQR (SEQ ID NO:4), each with no or up to one, two, three, four, five, six, seven, eight, nine or ten conservative or non-conservative substitutions of residues other than the T/S residue.

In another embodiment, a purified preparation or kit of parts comprising a LRRK2 polypeptide or polynucleotide and an ERM family polypeptide or polynucleotide is provided. In another embodiment, the kit comprises a recombinant LRRK2 polynucleotide. In yet another embodiment, the kit comprises a recombinant ERM family polynucleotide.

In one embodiment, a recombinant cell capable of expressing a LRRK2 polypeptide and an ERM family polypeptide is provided. In another embodiment, the recombinant cell comprises a recombinant LRRK2 polynucleotide and a recombinant ERM family polynucleotide. In another embodiment, the recombinant cells comprises a LRRK2 polypeptide and ERM family polypeptide.

In one embodiment, a method is provided for making a preparation according to any one of methods disclosed above comprising the step of purifying the preparation from a cell according to any one of methods disclosed above. In another embodiment, a preparation is provided obtainable by a method disclosed above.

In one embodiment, a truncated LRRK2 polypeptide of less than 2000 amino acids having protein kinase activity on a substrate ERM family polypeptide is provided, comprising at least the GTPase domain, COR domain, kinase domain, WD40-like motif and C-terminal tail residues of wild type human LRRK2 or a variant or naturally occurring mutant thereof. In another embodiment, the truncated LRRK2 polypeptide comprised at least residues 1326-2527 of wild type human LRRK2 or a variant or naturally occurring mutant thereof.

In another embodiment, polypetides comprises the LRRK2 polypeptide GST-LRRK2[1326-2527, G2019S] or GST-LRRK2[1326-2527] are provided.

In one embodiment, a substrate polypeptide is provided which is a fragment derivable from an ERM family polypeptide, for example moesin, radixin or ezrin, which encompasses the residue corresponding to Thr558 residue of moesin and at least part of the surrounding sequence which includes this residue, for example at least the 2, 3, 4, 5, 6 or 7 residues C-terminal and N-terminal of this residue, for example the polypeptide RLGRDKYKTLRQIRQ (SEQ ID NO:1) or RLGRDKYKTLRQIRQGNTKQR (SEQ ID NO:2); or a polypeptide of less than 100, 80, 60, 50, 40, 30, 25, 20, 19, 18, 17 or 16 amino acids, comprising the amino acid sequence RLGRDKYK(T/S)LRQIRQ (SEQ ID NO:3) or RLGRD-KYK(T/S)LRQIRQGNTKQR (SEQ ID NO:4) each with no or up to one, two, three, four, five, six, seven, eight, nine or ten conservative or non-conservative substitutions of residues other than the T/S residue.

In another embodiment, a truncated LRRK2 polypeptide is provided. In another embodiment, a polynucleotide encoding the truncated substrate polypeptide is provided.

In one embodiment, a method of phosphorylating an ERM family polypeptide wherein the ERM family polypeptide is phosphorylated by an LRRK2 polypeptide is provided.

In another embodiment, use of an LRRK2 polypeptide in a method of phosphorylating an ERM family polypeptide is provided. In another embodiment, the ERM family polypeptide is phosphorylated on the threonine residue corresponding to Thr558 of full length human moesin.

In one embodiment, a method is provided comprising the step of assessing whether the compound modulates ERM family polypeptide phosphorylation in a whole cell, tissue or organism; or characteristics of Parkinsonism or Parkinson's Disease in an organism and a compound that modulates the activity or disease characteristics is selected. In another embodiment, the method further comprises the step of assessing whether the compound modulates the activity of an ERM family polypeptide in the whole cell, tissue or organism, and a compound that modulates the activity is selected. In another embodiment, the method further comprises the step of synthesising, purifying and/or formulating the selected compound.

In one embodiment, a method is provided for preparing a compound which modulates the activity of a LRRK2 polypeptide or phosphorylation of an ERM family polypeptide, the method comprising 1) performing a method disclosed above and 2) synthesising, purifying and/or formulating the selected compound.

In another embodiment, a method is provided of characterising an LRKK2 mutant, for example an LRRK2 mutant found in a patient with Parkinson's Disease, the method comprising the step of assessing the ability of the LRKK2 mutant to phosphorylate a substrate ERM family polypeptide.

BRIEF DESCRIPTION OF THE DRAWINGS

FIG. 14 depicts the human ERM family polypeptide sequence alignment.

FIG. 15 depicts analysis of phosphorylation of moesin by LRRK2 (A) Sequence alignment of the C-terminal regions of Ezrin, Radixin and Merlin. The asterisks indicate the Thr residue equivalent to Thr555 on moesin. Black and grey shaded residues represent identical and homologous residues, respectively. (B) E. coli expressed full length GST-moesin, GST-Ezrin, GST-Radixin or the GST-moesin[500-577] C-terminal fragment (C' Moesin) was either left on ice (-) or incubated for 15 min at 70° C. (+), prior to phosphorylation with GST-LRRK2[1326-2527, G2019S]. Phosphorylation of the ERM proteins was determined following electrophoresis on a polyacrylamide gel and subsequent autoradiography (left panel) of the colloidal blue-stained bands corresponding to moesin (right panel).

FIG. 24A depicts LRRK2 residue preferences displayed semi-quantitatively by proportional representation of single letter amino acid symbols above the position relative to phosphorylation site. A derived consensus sequences is shown below the positions. FIG. 24B depicts an alignment of the peptide substrate sequences previously used for LRRK2, LRRKtide and LongLRRKtide, along with a new peptide in which the preferred LRRK2 residues are substituted, henceforth referred to as Nictide. The left panel of FIG. 24C shows concentration dependent phosphorylation of Nictide versus LongLRRKtide at 5 min reaction times. Calculated Km values are 6 µM for Nictide. The right panel of FIG. 24C shows a comparison of LRRKtide, LongLRRKtide and Nictide at 15 min at 5 µM peptide concentration.

FIG. 30 depicts the fusion of human LRRK2 residues 100-498 used in raising an antibody useful in binding to and in immunoprecipitating LRRK2.

DETAILED DESCRIPTION OF THE INVENTION

Figure 1:
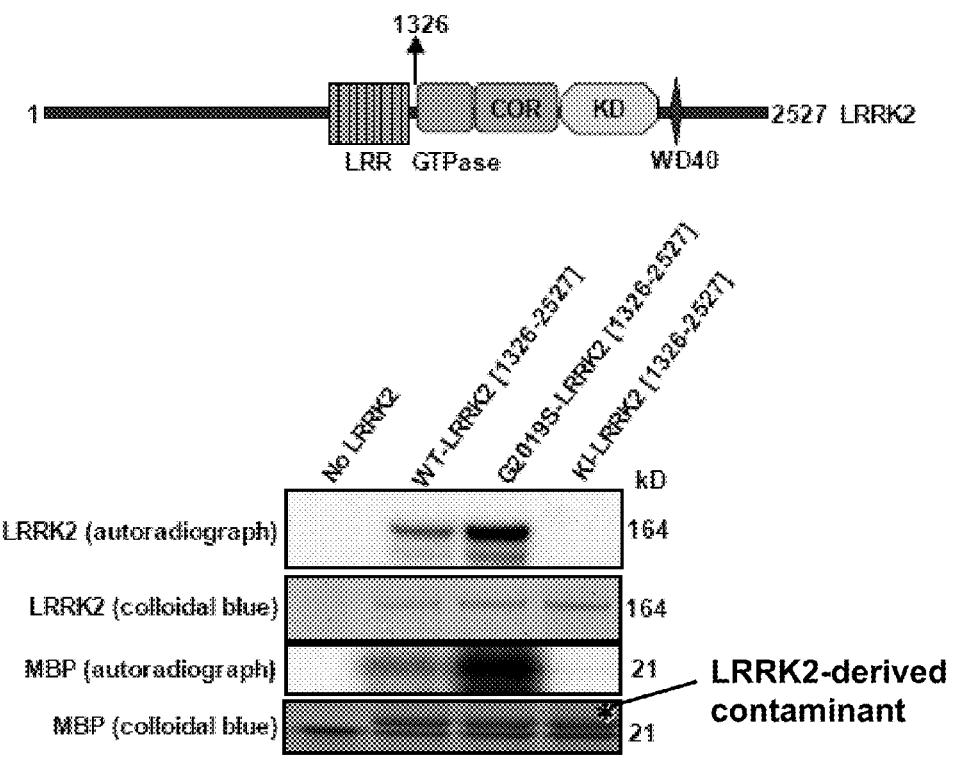
FIG. 1 depicts the generation of an active LRRK2 fragment for KESTREL screen. (Upper panel) Schematic representation of the domain structure of LRRK2 showing predicted functional domains, numbering of residues corresponds to human LRRK2 (accession number AAV63975). Abbreviations LRR (leucine-rich repeat), COR(C-terminal Of Ras conserved motif), KD (Serine/threonine protein kinase domain). 293 cells were transfected with constructs encoding the indicated forms of GST-LRRK2. Thirty-six hours post-transfection, LRRK2 kinases were affinity purified and analysed by electrophoresis on a polyacrylamide gel and stained with colloidal blue to quantify relative protein levels. GST-LRRK2 was assayed by measuring phosphorylation of MBP and autophosphorylation of LRRK2 following electrophoresis on a polyacrylamide gel and subsequent autoradiography of the colloidal blue-stained bands corresponding MBP or LRRK2. * indicates a protein that contaminates the GST-LRRK2 preparations. Similar results were obtained in three separate experiments.

A method was developed to express active recombinant LRRK2 and utilised in a KinasE Substrate TRacking and ELucidation (KESTREL) screen, that has recently been developed to assist in searching for physiological substrates of protein kinases. This led to the identification of moesin as a potential physiological substrate, that when denatured was efficiently phosphorylated by LRRK2 at Thr558, a previously characterised physiologically relevant phosphorylation site. These findings were utilized to develop a robust and quantitative assay for LRRK2. Using this methodology several LRRK2 mutations were identified in patients with PD, which either do not affect or actually inhibit, rather than activate LRRK2.

A first embodiment provides a method for identifying a compound expected to be useful in modulating LRRK2 protein kinase activity, the method comprising the steps of (1) determining whether a test compound modulates the protein kinase activity of a LRRK2 polypeptide on a substrate Ezrin/Radixin/Moesin (ERM) family polypeptide and (2) selecting a compound which modulates the said LRRK2 polypeptide protein kinase activity.

The protein kinase activity of the LRRK2 polypeptide that is modulated/assessed in the screening method is phosphorylation of an ERM family polypeptide. Phosphorylation of an ERM family polypeptide may be assessed by measuring phosphorylation or modulation of the ERM family polypeptide, as discussed further below and in the Examples. For example, antibodies specific for a phosphorylated (or unphosphorylated) phosphorylation site of, for example, moesin, may be used in assessing phosphorylation of that phosphorylation site, as well known to those skilled in the art. Further methods will be apparent to the skilled person on the basis of this teaching and the many known methods of assessing protein phosphorylation.

Phosphorylation of an ERM family polypeptide may also be assessed by assessing the ability of the ERM family polypeptide to bind actin or to bind to the cell membrane or membrane components, for example PtdIns-4,5P$_2$ or membrane-associated polypeptides such as L-selectins, ICAM 123 or CD44. The FERM domain of moesin, for example, has been reported to interact with several plasma membrane proteins as well as PtdIns-4,5P$_2$. The last 30 residues of moesin, for example, are considered to form an F-actin binding site. Methods of assessing such binding will be well known to those skilled in the art.

ERM family polypeptide phosphorylation or modulation may also be assessed in a cell, for example by assessing cytoskeletal parameters. In an example, a platelet-based assay as described in Nakamura et al (1995) *J Biol Chem* 270(52), 31377-31385 "Phosphorylation of Threonine 558 in the Carboxyl-terminal Actin-binding Domain of Moesin by Thrombin Activation of Human Platelets" may be used and is incorporate by reference herein for all it discloses regarding platelet-based assays. Platelets are reported to contain moesin but not other family members Radixin and Ezrin. A non-specific inhibitor of serine/threonine kinases (staurosporine) and inhibitors of phosphatases were found to have opposite effects on moesin phosphorylation, but both were found to cause the platelets to form extremely long filopodia and not to spread on glass. Phosphorylated moesin was found concentrated together with F-actin in the centre of the cell. Thus, either the behaviour of the cells (for example cell shape) or the location of moesin and/or actin may be used (with suitable controls, as will be apparent to those skilled in the art) in assessing (or further assessing) the effect of a test compound on LRRK2 polypeptide protein kinase activity.

A further embodiment provides a method for identifying a compound expected to be useful in modulating, for example inhibiting, the phosphorylation of an ERM family polypeptide in a cell, the method comprising the steps of (1) determining whether a test compound modulates, for example inhibits, the protein kinase activity of a LRRK2 polypeptide or the protein kinase activity of a LRRK2 polypeptide on a substrate polypeptide comprising the sequence (W/F/R/K)(W/F/R/K)(R/K)(F/W/H/R)(Y/W/R)(S/T)(L/V/I)(R/K)(R/K)(A/Y) (SEQ ID NO:52), and (2) selecting a compound which modulates, for example inhibits, the protein kinase activity of the LRRK2 polypeptide or the protein kinase activity of the LRRK2 polypeptide on the substrate polypeptide.

As used herein, the designation of an amino acid residue in the instant peptides as more than one amino acid (using the common one-letter amino acid code) in parenthesis with a slash between the amino acids, mean that any of the indicated amino acids, or mimetics thereof (unless specifically excluded), could occupy that residue. For example, (I/L/V)(T/S/A/V/C) means that the first residue can be any one of isoleucine, leucine, or valine, and the second residue can be any one of threonine, serine, alanine, valine, or cysteine, or mimetics.

A further embodiment provides a method for identifying a compound expected to be useful in treating or preventing Parkinson's Disease (PD) or Parkinsonism (or other neurodegenerative condition), the method comprising the steps of (1) determining whether a test compound modulates, for example inhibits, the phosphorylation of substrate polypeptide or an ERM family (for example moesin) polypeptide, and (2) selecting a compound which modulates, for example inhibits, the phosphorylation of the substrate or ERM family (for example moesin) polypeptide, wherein the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52). The method may comprise the steps of (1) determining whether a test compound modulates, for example inhibits, the phosphorylation of a substrate polypeptide or an ERM family (for example moesin) polypeptide by an LRRK2 polypeptide, and (2) selecting a compound which modulates, for example inhibits, the phosphorylation of the substrate or ERM family (for example moesin) polypeptide by the LRRK2 polypeptide. Examples of methods for assessing the phosphorylation of an ERM family polypeptide are discussed herein and in the Examples and include methods making use of phosphorylation-specific antibodies, as discussed herein.

The activity of the LRRK2 polypeptide may be measured by measuring the phosphorylation by the LRRK2 polypeptide, in the presence of a suitable phosphate donor, of s substrate polypeptide or an ERM family polypeptide, as discussed above. Examples of methods of assessing the phosphorylation of the substrate or ERM family polypeptide are indicated herein.

The protein kinase activity may be increased or reduced by an alteration in the $V_{max}$ or the $K_m$ (or both) of the LRRK2 polypeptide for a particular substrate. For example, activity may be increased by an increased $V_{max}$ or decreased $K_m$. It will be appreciated that it may not be necessary to determine the value of either $V_{max}$ or $K_m$ in order to determine whether the LRRK2 polypeptide has been activated or deactivated.

Activity may be measured as the amount of a substrate phosphorylated in a given time; a change of activity may therefore be detected as a change in the amount of substrate (for example, at a single concentration) that is phosphorylated in a given time. It is preferred that the activity is increased or decreased, as appropriate, by at least 2, preferably 5, 10, 15, 20, 25, 30 or 50-fold.

It will be appreciated that it may be necessary to determine the effect of the compound on the properties of the substrate, for example by measuring the properties of the substrate when exposed to the compound (1) after exposure of the substrate to the LRRK2 polypeptide, (2) before exposure of the substrate to the LRRK2 polypeptide and/or (3) without exposure to the LRRK2 polypeptide.

By modulation of the protein kinase activity is included inhibition or an increase in the protein kinase activity.

It will be appreciated that in the disclosed methods wherein phosphorylation of a polypeptide may occur that the presence of a suitable phosphate donor may be required, as described above. Suitable phosphate donors will be known to those skilled in the art and include ATP, for example as the magnesium salt (MgATP), as described in the Examples.

It may be useful to assess the effect of the test compound on the binding of the LRRK2 polypeptide and the substrate or ERM family polypeptide. Methods of assessing polypeptide:polypeptide interactions will be well known to those skilled in the art.

The LRRK2 and/or ERM family polypeptides may, for example, be purified from cells in which the LRRK2 and/or ERM family polypeptides are expressed naturally, but it may be more convenient for at least one of the LRRK2 and ERM family polypeptides to be recombinant. As described further below and in the Examples, an LRRK2 fragment has been identified that is useful in raising or selecting an antibody that is useful in, for example, preparing LRRK2 that retains protein kinase activity from cells in which the LRRk2 polypeptide is expressed naturally. Thus, the LRRK2 polypeptide may be an LRRK2 polypeptide prepared using such an antibody.

The term ERM family polypeptide will be well known to those skilled in the art, as indicated above. ERM family members include moesin, ezrin and radixin, as noted above. Merlin is another ERM family member. The ERM family polypeptide used in the assay may be recombinant or non-recombinant. The ERM family polypeptide may be, for example, a bacterially-expressed or mammalian cell-expressed ERM family polypeptide (for example as described in the Examples). The ERM family polypeptide may have the amino acid sequence of a naturally occurring ERM family member, for example the amino acid sequence of a naturally occurring moesin, ezrin, radixin or merlin polypeptide, or may be or comprise a fusion polypeptide (for example as described in Example 1), or may be a fragment or variant of a naturally occurring ERM family member that retains the ability to be phosphorylated or activated by a LRRK2 polypeptide, for example LRRK2[1326-2527] or LRRK2[1326-2527, G2019S], for example as described in Example 1. Thus, it is preferred that the ERM family polypeptide is an ERM family polypeptide that retains a threonine (or serine) residue at the position corresponding to Threonine-558 of full length wild-type human moesin. It is preferred that the ERM family polypeptide is not a mutant in which the residue corresponding to Thr558 is replaced by a residue other than threonine or serine, for example is replaced by alanine. The ERM family polypeptide may be a ERM family polypeptide that retains a threonine (or serine) residue at the position corresponding to Thr526 of full length wild-type human moesin. The ERM family polypeptide may be not a mutant in which Thr526 is replaced by a residue other than threonine or serine, for example is replaced by alanine. A fragment derivable from an ERM family polypeptide, for example moesin, radixin or ezrin, which encompasses the residue corresponding to Thr558 residue of moesin and at least part of the surrounding sequence which includes this residue, for example at least the 2, 3, 4, 5, 6 or 7 residues C-terminal and N-terminal of this residue, is a suitable substrate for use in the screening method. A fragment derivable from an ERM family polypeptide, for example moesin, radixin or ezrin, which encompasses the residue corresponding to Thr526 residue of moesin and at least part of the sequence which includes this residue, for example at least the 2, 3, 4, 5, 6 or 7 residues C-terminal and/or N-terminal of this residue, may be a suitable substrate for use in the screening method. The polypeptide may have, for example, at least 8 or 9 residues encompassing this residue, for example with 5 to 6 residues N-terminal of this residue and 2 or 3 residues C-terminal of this residue.

As shown in the Examples and Figures, LRRK2 phosphorylates the equivalent residues on ezrin, radixin, moesin and merlin and any one of these could be used as a substrate for LRRK2, for example in a screening assay. All are similarly phosphorylated and it is considered that there would not be significant differences depending on which was used.

A suitable substrate, derivable from moesin, radixin or ezrin and encompassing the residue corresponding to Thr558 of moesin is RLGRDKYKTLRQIRQ (SEQ ID NO:1) or RLGRDKYKTLRQIRQGNTKQR (SEQ ID NO:2). The residue corresponding to Thr558 of moesin is underlined.

The ERM family polypeptide can be a polypeptide of less than 100, 80, 60, 50, 40, 30, 25, 20, 19, 18, 17 or 16 amino acids, comprising the amino acid sequence RLGRDKYK(T/S)LRQIRQ (SEQ ID NO:3) or RLGRDKYK(T/S)LRQIRQGNTKQR (SEQ ID NO:4), each with no or up to one, two, three, four, five, six, seven, eight, nine or ten conservative or non-conservative substitutions of residues other than the T/S residue. The ERM family polypeptide can also be a polypeptide of less than 16 amino acids comprising at least 7, 8, 9 or 10 amino acids from this sequence encompassing the T/S residue with no or up to one, two, three, four, five, six, seven, eight, nine or ten conservative or non-conservative substitutions of residues other than the T/S residue. The substrate polypeptide (W/F/R/K)(W/F/R/K)(R/K)(F/W/H/R)(Y/W/R)(S/T)(L/V/I)(R/K)(R/K)(A/Y) (SEQ ID NO:52) is an example of such a polypeptide. The polypeptide sequence may typically be derived from the sequence of a naturally occurring ERM family polypeptide, for example moesin, radixin or ezrin, for example human moesin, radixin or ezrin, optionally with conservative or non-conservative substitutions of residues (for example of up to 10, 20, 30, 40, 50 or 60% of the residues).

Figure 19:
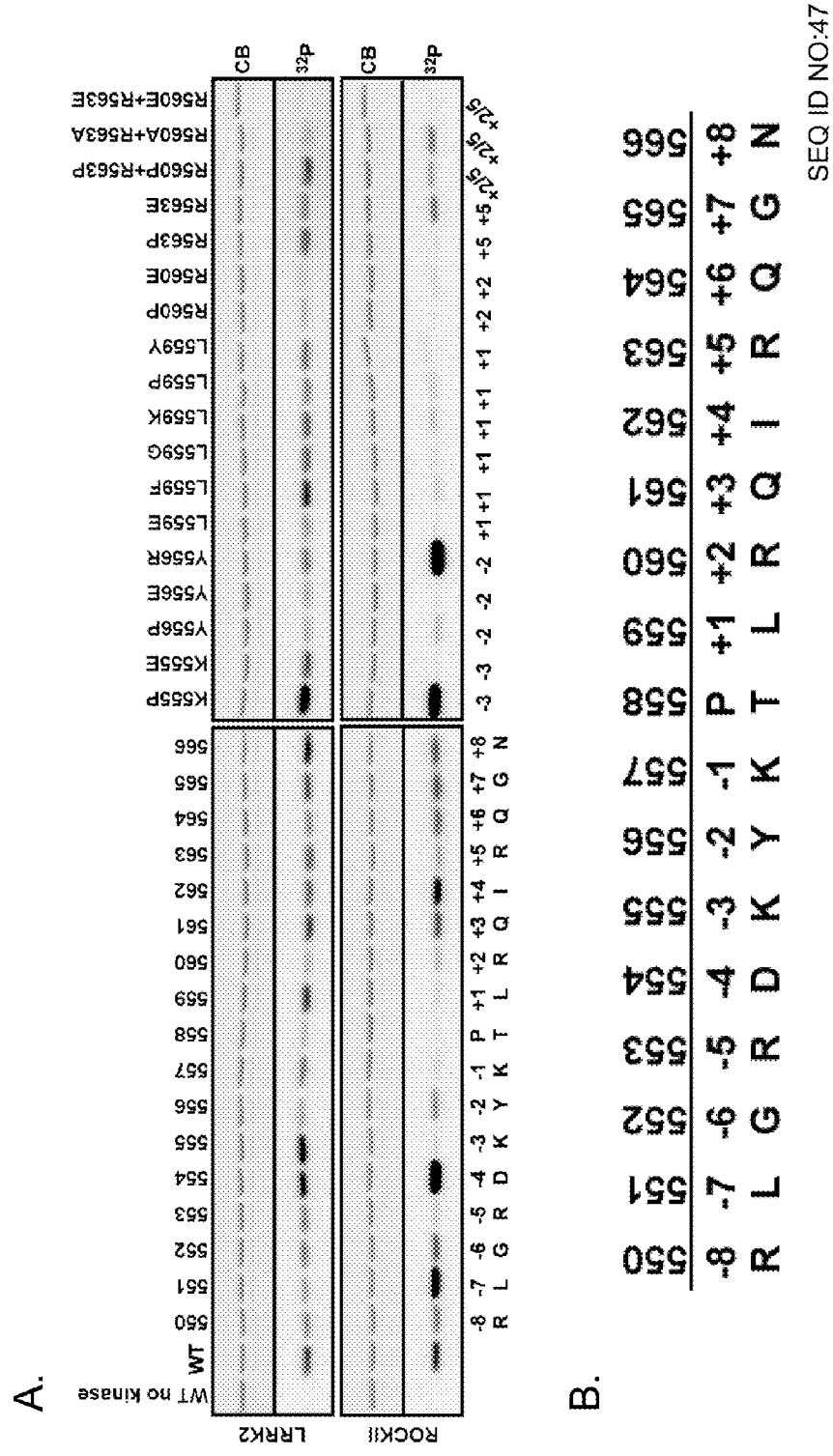
FIG. 19 depicts elucidation of LRRK2 phosphorylation site determinants in recombinant protein. A. Shown in the left panels, moesin 500-end T526A was subjected to site directed mutagenesis where the amino acids from the -8 to +8 position of the phosphorylation site were changed to Ala. In the right panels, moesin 500-end T526A was subjected to site directed mutagenesis where the indicated residues of moesin were replaced with the indicated residues. These proteins were subjected to in vitro kinase reactions with LRRK2 and Rock and reaction products were evaluated by SDS-PAGE and coomassie blue staining (CB) followed by autoradiography ($^{32}$P). B. The sequence of the residues surrounding the moesing T558 phosphorylation site is shown with numbering and residue position indicated.
Figures 20A, 20B:
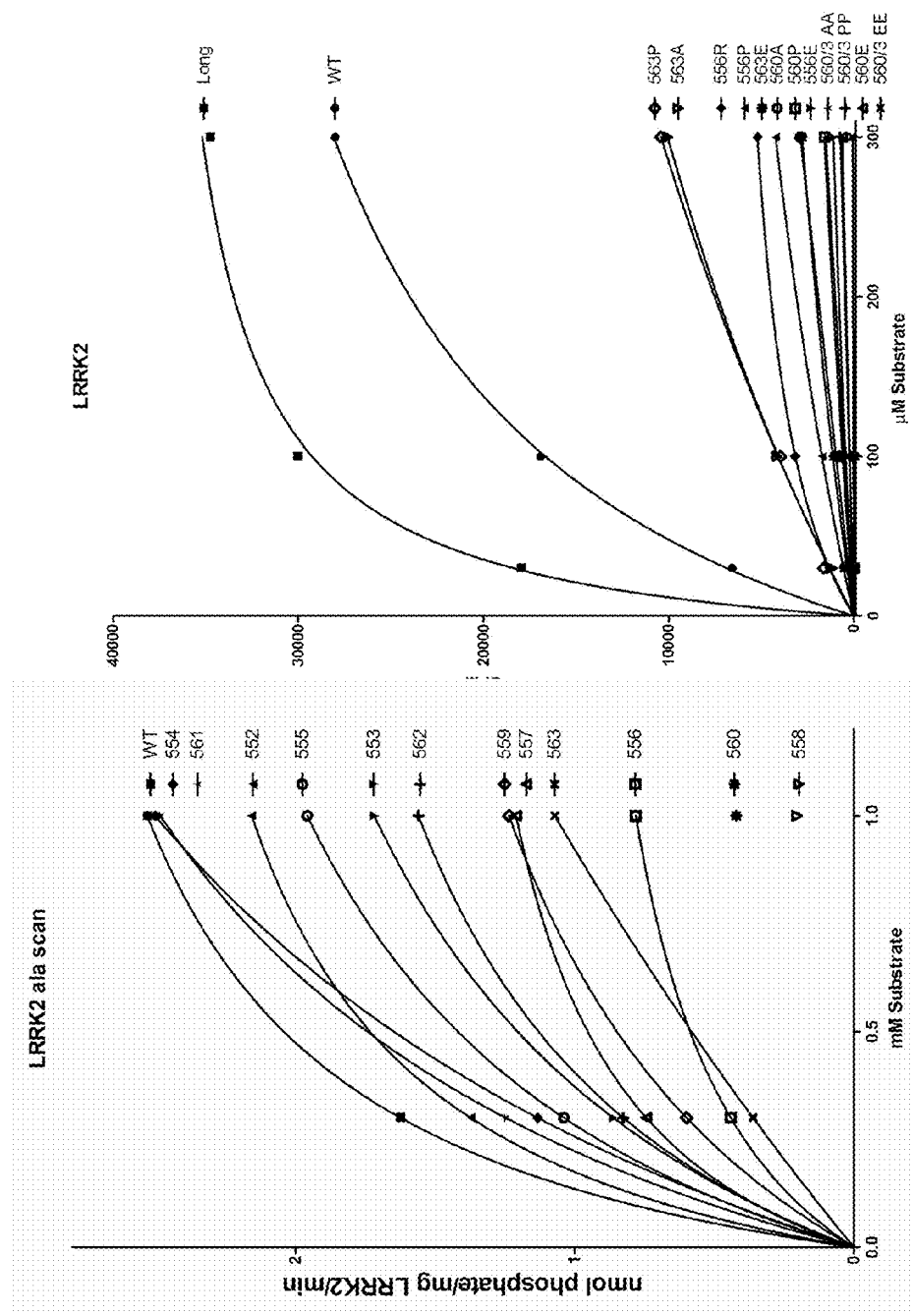
FIG. 20 depicts elucidation of LRRK2 phosphorylation site determinants in peptides. To further study the amino acid determinants that direct LRRK2 recognition of LRRKtide compared to Rock, individual peptides were synthesized where the residues -6 to +5 of LRRKtide were substituted with Ala, 3A and C. Additionally, peptides were synthesized where the residues were also altered to the indicated residues FIGS. 19B and D. A longer LRRKtide (Long), with the +7 to +12 residues of the Thr 558 site was compared to the LRRK-tide. Concentration dependent phosphorylation of peptides was monitored for both LRRK2 (A and B) and Rock (C and D).
Figures 20C, 20D:
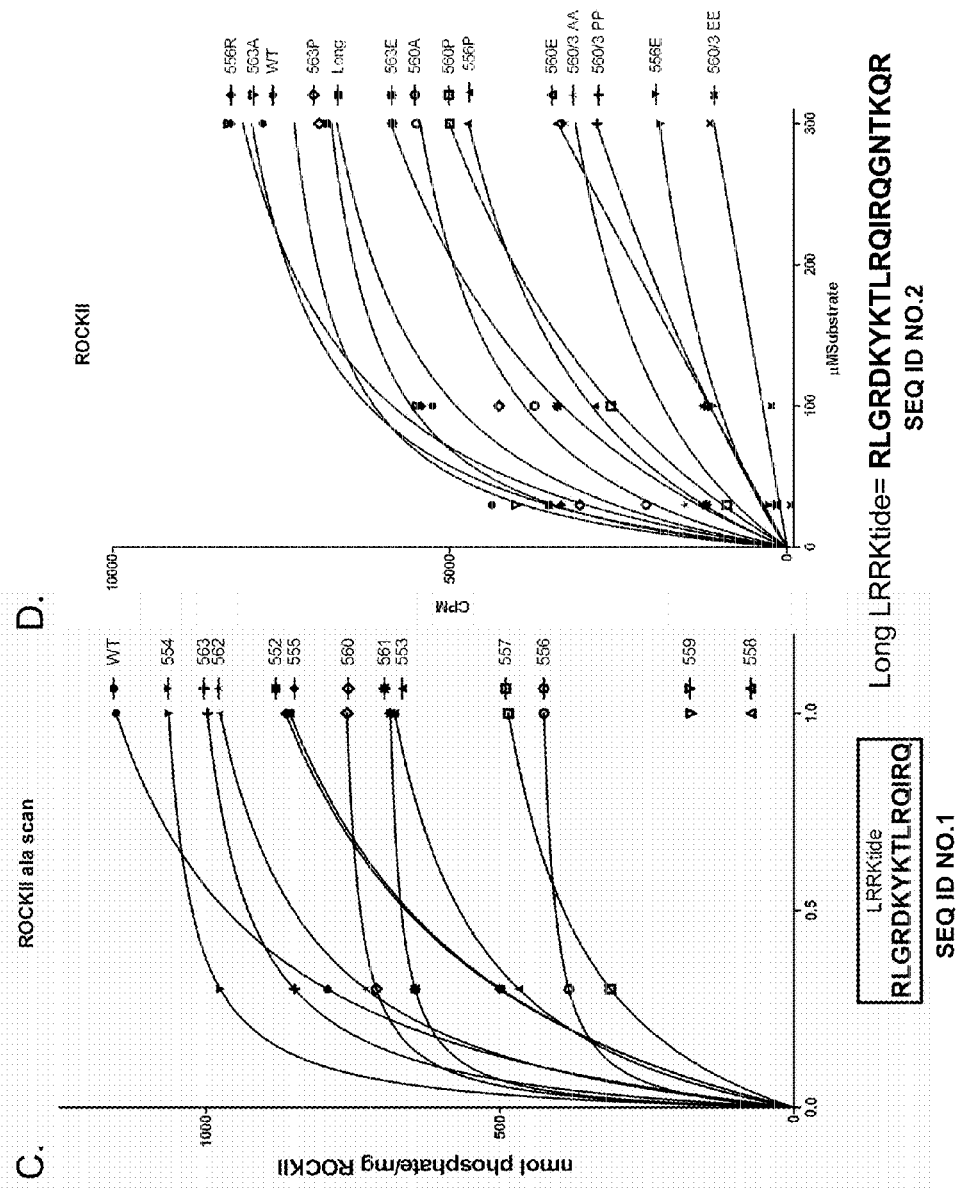
Figure 21:
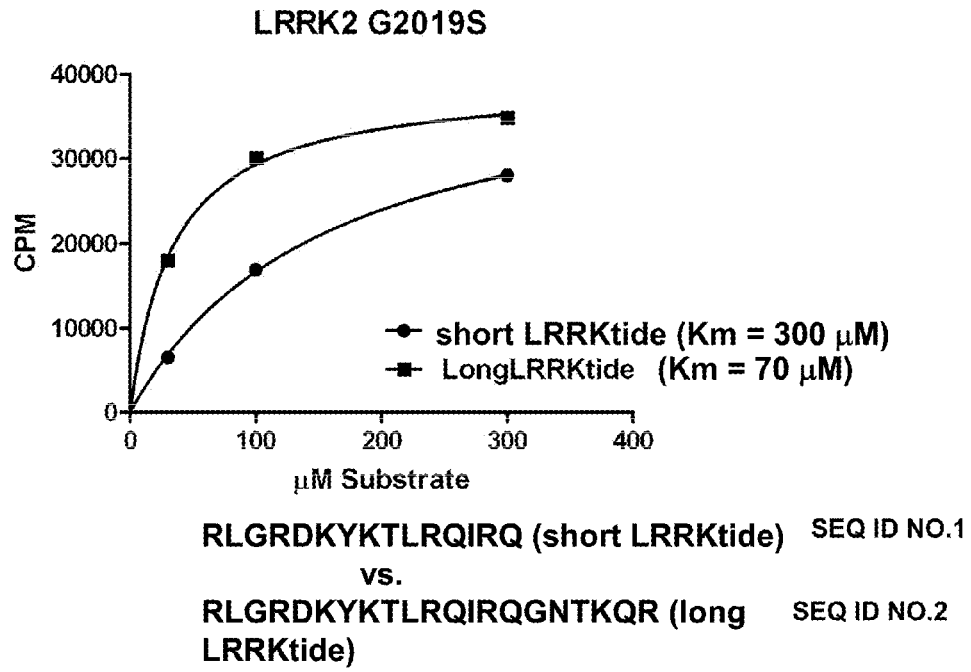
FIG. 21 depicts that LRRK2 exhibits higher affinity for a longer LRRKtide with a carboxy terminal extension. A longer LRRKtide, with the +7 to +12 residues of the Thr 558 site was compared to the LRRKtide by phosphorylation with LRRK2. Analysis of Ala substitutions at distal+position residues in recombinant moesin revealed slight differences in phosphorylation by LRRK2. The LRRK2 affinity for the longLRRK-tide is ten fold more than that of LRRKtide.

The data presented in FIGS. 19 and 20 also shows the relative importance of the individual residues surrounding the Thr residue equivalent to Thr558. The most important residue appear to be Tyr556 (−2 position) and a marked preference for a basic residue at the +2 position was also noted. Thus, in an embodiment the polypeptide has a tyrosine residue at position −2 relative to the T/S residue and/or a basic residue (for example arginine or lysine at position +2 relative to the T/S residue.

The longer sequence RLGRDKYK(T/S)LRQIRQGNTKQR (SEQ ID NO:4, termed Long-LRRKtide) is considered to allow the use 5-10-fold lower amounts of peptide relative to the shorter sequence RLGRDKYK(T/S)LRQIRQ (SEQ ID NO:3, short LRRKtide). However the core recognition motif in the short and long peptide sequences is identical.

It may be necessary to denature an ERM polypeptide (for example if it comprises both a FERM domain (for example residues 1 to 298 of human moesin) and the C-terminal tail region (C-ERMAD domain, for example residues 489 to 575 of human moesin)) in order for it to be phosphorylated in vitro by an LRRK2 polypeptide, as discussed in Example 1. Accordingly, it may be desirable for the ERM polypeptide not to comprise a functional FERM domain.

Examples of Accession numbers for ERM family polypeptides in the NCBI database include:
AAB02864, M86450 (pig moesin)
AAA39728, M86390.1, NP_034963, NM_010833.2 (house mouse moesin)
NP_002435, NM_002444.2 (human moesin)
NP_110490, NM_030863.1 (Norway rat moesin)
NP_001039942, NM_001046477.1 (bovine moesin)
NP_062230, NM_019357.1 (Norway rat ezrin)
CAA43086, X60671.1 (house mouse ezrin)
P15311 (human ezrin)
NP_002897, NM_002906.3 (human radixin)
NP_033067, NM_009041 (house mouse radixin)
NP_001005889, NM_001005889.2 (Norway rat radixin)
NP_001009576, NM_001009576.1 (pig radixin)
P35240 (human merlin)
P46662 (house mouse merlin)
Q63648 (Norway rat merlin)

Numerous further examples of mammalian and non-mammalian ERM family polypeptide sequences can be accessed in the sequence databases accessible from the NCBI Medline™ service, as will be well known to the person skilled in the art.

The term LRRK2 will be well known to those skilled in the art, as indicated above. The LRRK2 or substrate polypeptides used in the assay may be recombinant or non-recombinant. The LRRK2 or substrate polypeptides may be, for example, a bacterially-expressed or mammalian cell-expressed LRRK2 or substrate polypeptides (for example as described in the Examples). It may be appropriate to express the LRRK2 polypeptide alongside the substrate polypeptide, e.g., a ERM family polypeptide. The LRRK2 polypeptide may have the amino acid sequence of a naturally occurring LRRK2, or may be or comprise a fusion polypeptide (for example as described in Example 1), or may be a fragment or variant of a naturally occurring LRRK2 that retains the ability to phosphorylate an ERM family polypeptide or myelin basic protein, for example as described in Example 1, for example that retains the ability to phosphorylate (denatured, as discussed in Example 1) moesin or a fragment thereof on the residue corresponding to Thr558 (or Thr526) of full length human moesin. Thus, the LRRK2 polypeptide is an LRRK2 polypeptide that retains an active kinase domain. It is also considered that in order to be catalytically active, the LRRK2 polypeptide retains regions corresponding to the GTPase domain, COR domain, WD40-like motif and C-terminal tail, as discussed in Example 1. The LRRK2 polypeptide may not comprise the Leucine Rich Repeat (LRR) motif present in full length LRRK2. The LRRK2 polypeptide may comprise or consist of residues 1326-2527 of wild-type human LRRK2, or a GST fusion of such a fragment, as described in Example 1. A fragment of a LRRK2 which contains the intact kinase domain and other domains indicated above but not other regions of LRRK2 (for example the Leucine Rich Repeat (LRR) motif) may be useful; this region of LRRK2 is sufficient to retain protein kinase activity but is shorter than full length LRRK2 and easier to express in an active form. The LRRK2 polypeptide used in the assay is not a kinase-dead mutant such as is described in the Examples (for example LRRK2 in which the residue equivalent to residue D2017 of full length human LRRK2 is mutated, for example to Alanine).

Thus, the LRRK2 polypeptide can be wild type human LRRK2 or a fragment thereof, or a fusion either thereof. The fragment may comprise at least residues 1326-2527 of wild type human LRRK2. It is considered that truncation at the C-terminus may adversely effect the protein kinase activity of the truncated LRRK2 polypeptide, whilst truncation at the N-terminus of the fragment may be better tolerated. Thus, the N-terminus of the truncated LRRK2 polypeptide may alternatively lie after residue 1326, for example between residue 1326 and about residue 1336.

The substrate polypeptide may be or comprise a fusion polypeptide (for example as described in the Examples that retains the ability to be phosphorylated by a LRRK2 polypeptide, for example by LRRK2[1326-2527] or LRRK2[1326-2527, G2019S], for example as described in the Examples. The fusion may typically be with a tag, for example a GST tag, as will be well known to those skilled in the art. Alternatively or in addition, it may be with all or part of an ERM polypeptide. In an example the wild-type phosphorylation site of the ERM polypeptide may be replaced by the substrate polypeptide sequence of the invention.

Figure 25:
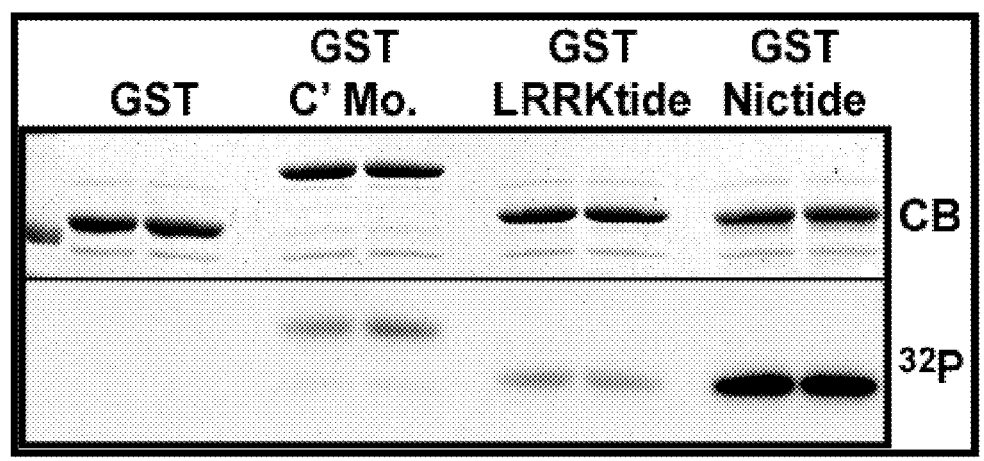
FIG. 25 depicts the modification of Nictide diplayed as a fusion to a recombinant protein. GST or fusion proteins of GST with the carboxy terminus of moesin (amino acids 500-End), the sequence of LRRKtide or Nictide were prepared from bacteria. These recombinant proteins were presented as substrates for GST tagged LRRK2 1326-End G2019S for 10 min in the presence of [γ-$^{32}$P]-ATP. Reaction products were resolved on 12% SDS-polyacrylamide gels and visualized by coomassie blue staining (CB) and autoradiography ($^{32}$P).
Figure 26:
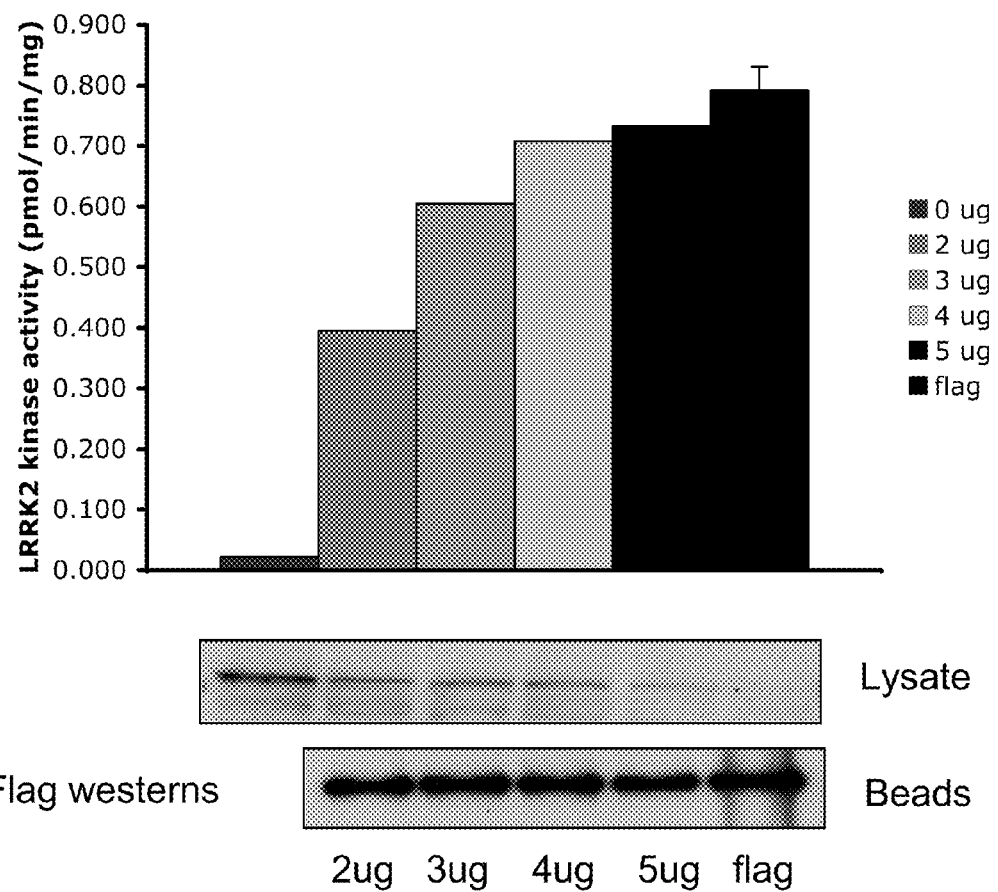
FIG. 26 depicts an antibody raised in sheep against the amino terminal 500 amino acids of LRRK2 using recombinant protein as an immunogen (see FIG. 30). Specific antibodies were isolated by positive selection with recombinant protein. One milligram of lysates of HEK293 cells stably expressing full length Flag tagged LRRK2 G2019S were subjected to immunoprecipition with increasing amounts of antibody conjugated to 10 µl of protein G sepharose and anti-FLAG M2 agarose as control. Immunocomplexes were used in kinase assay with LongLRRKtide. Immunodepletion of LRRK2 from the lysates is shown as well as immunoblot analysis of the immunoprecipitates using anti-flag.
Figure 27A:
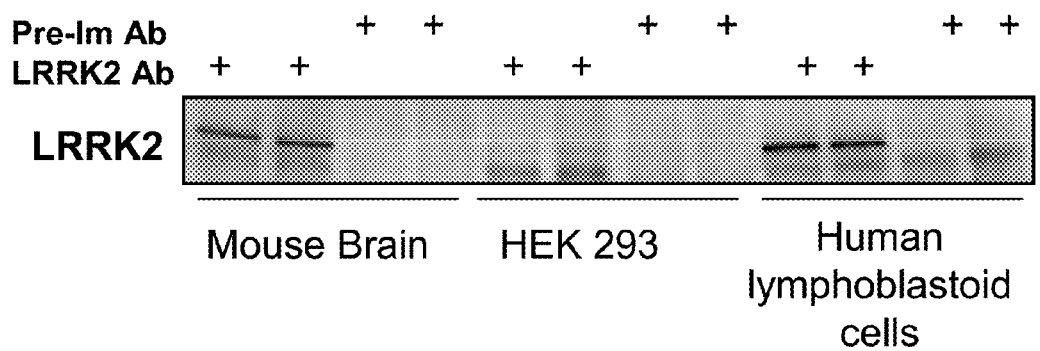
FIG. 27 depicts the anti-LRRK2 1-500 antibody immunoprecipitates endogenous protein from mouse brain lysate, and human lymphoblastoid lystates (FIG. 27A). The LRRK2 antibody was used in an immunoprecipitation of 13 mg of NIH3T3 lysate. The immunoprecipitates were eluted with sample buffer and resolved on a 4-12% Novex gel and stained with colloidal blue (FIG. 27B). Bands 1 and 2 were excised and subjected to analysis by mass spectrometry. Band contained 16 peptide matches for LRRK2, while band 2 contained no peptides matching LRRK2.
Figure 27B:
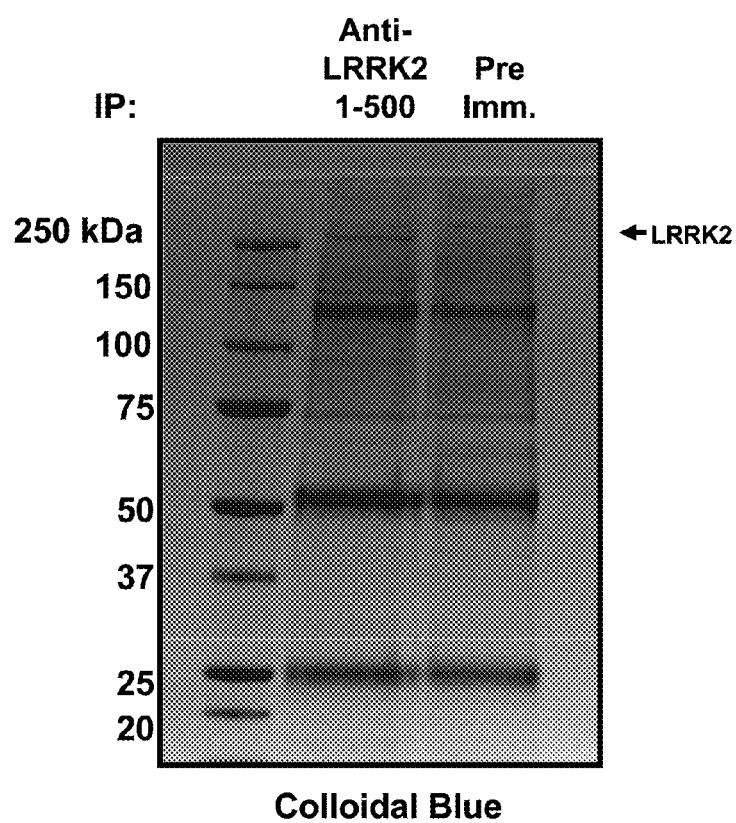
Figure 28:
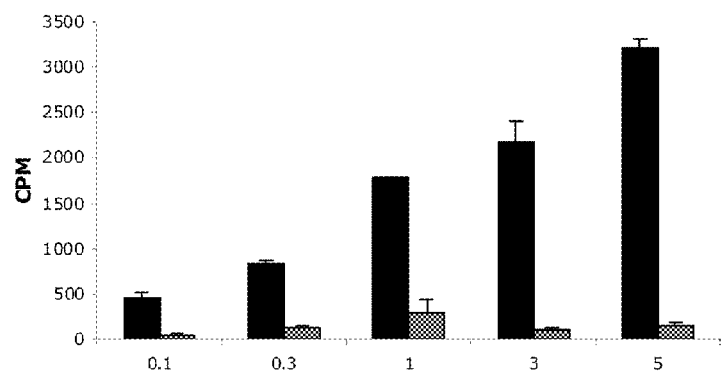
FIG. 28 depicts increasing amounts of NIH3T3 lysate used to immunoprecipitate LRRK2 and assayed for activity against Nictide. Anti-LRRK2 reactions are represented in black bars and pre-immune reactions are represented by grey bars.

As indicated above, the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52) (optionally with up to three substitutions, as discussed above). For example, the substrate polypeptide may comprise the sequence WWRFYTLRRA (SEQ ID NO:65). Alternatively, the substrate polypeptide may comprise the sequence WWKFYTLRRA (SEQ ID NO:67) or WWRFYTLRKA (SEQ ID NO:48). An example of a suitable substrate polypeptide is RLGWWRFYTLRRARQGNTKQR (SEQ ID NO:51). The residue phosphorylated by LRRK2 is underlined. This substrate polypeptide is termed "Nictide" in the Examples and Figures. The following are further examples of suitable substrate peptides: RLGWWKFYTLRRARQGNTKQR (SEQ ID NO:49) and RLGWWRFYTLRKARQGNTKQR (SEQ ID NO:50). FIGS. 24 and 25 also indicate peptide sequences that are considered to be compatible with the ability of the peptide to act as a substrate for LRRK2, reflected in the consensus.

As noted above, the substrate polypeptide may comprise a tag sequence, as will be well known to those skilled in the art, for example a Glutathione S-Transferase (GST) or a Myc tag. Thus, a further example of a suitable substrate polypeptide is a fusion of RLGWWRFYTLRRARQGNTKQR (SEQ ID NO:51) and a tag sequence, for example a GST tag, for example as described in the Examples.

The substrate polypeptide can be a polypeptide of less than 100, 80, 60, 50, 40, 30, 25, 20, 19, 18, 17 or 16 amino acids, comprising the amino acid sequence (W/F/R/K)(W/F/R/K)(R/K)(F/W/H/R)(Y/W/R)(S/T)(L/V/I)(R/K)(R/K)(A/Y) (SEQ ID NO:52). The substrate polypeptide sequence may typically comprise one or more amino acid sequences of at least five amino acids in length derived from the sequence of a naturally occurring ERM family polypeptide, for example moesin, radixin or ezrin, for example human moesin, radixin or ezrin, optionally with conservative or non-conservative substitutions of residues (for example of up to 10, 20, 30, 40, 50 or 60% of the residues). The amino acid sequence derived from the sequence of a naturally occurring ERM family polypeptide typically does not include the residue(s) of the ERM family polypeptide that are phosphorylated by LRRK2, for example the residue corresponding to Thr558 (or Thr526) of moesin.

The substrate polypeptides shown above include a sequence (GNTKQR) that is present in the previously identified substrate sequence RLGRDKYK(T/S)LRQIRQGNTKQR (SEQ ID NO:4; termed Long-LRRKtide) but not in the previously identified shorter sequence RLGRDKYK(T/S)LRQIRQ (SEQ ID NO:3; short LRRKtide). Long LRRKtide is considered to allow the use 5-10-fold lower amounts of peptide relative to short LRRKtide. The sequence GNTKQR is a sequence found in moesin, ezrin, or radixin.

It may be necessary to denature the substrate polypeptide (for example if it comprises both a FERM domain (for example residues 1 to 298 of human moesin) and the C-terminal tail region (C-ERMAD domain, for example residues 489 to 575 of human moesin)) in order for it to be phosphorylated in vitro by an LRRK2 polypeptide, as discussed in Jaleel et al (2007) supra and in PCT/GB2008/001211, filed on 7 Apr. 2008. Accordingly, it may be desirable for the substrate polypeptide not to comprise a functional FERM domain.

The LRRK2 polypeptide can be human LRRK2 having a naturally occurring mutation of wild type human LRRK2; or a fragment thereof; or a fusion either thereof. The fragment may comprise at least residues 1326-2527 of human LRRK2 having a naturally occurring mutation.

The naturally occurring mutation of human LRRK2 may be a mutation associated with Parkinson's Disease (PD). The mutation, using the numbering of wild type human LRRK2, may be G2019S. This mutation is considered to enhance the protein kinase activity of LRRK2, as discussed further in Example 1.

Figure 17:
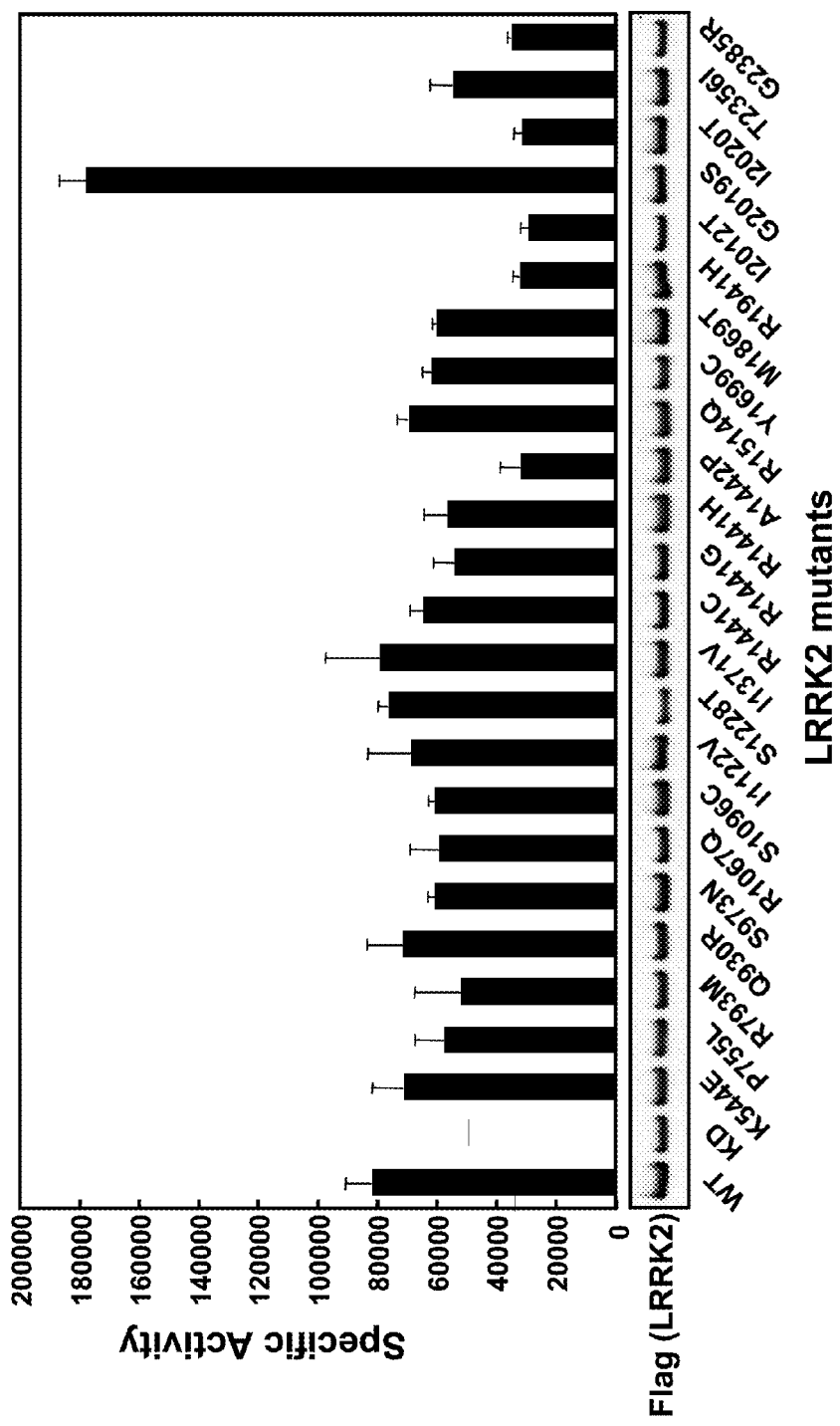
FIG. 17 depicts the analysis of PD associated mutations on the kinase activity of LRRK2. Flag epitope tagged, full length wild-type (WT), kinase dead (KD) and mutant cDNA alleles of LRRK2 were expressed in 292 cells and purified by immunoaffinity chromatography using monoclonal M2 anti-FLAG agarose resin. Immune complexes were assayed against LRRKtide in the presence of [γ-$^{32}$P] ATP. Specific activity is cpm of $^{32}$P incorporated into LRRKtide corrected for amount of LRRK2, which was determined by immunoblot quantitation by LICOR. The G2019S mutation results in an approximate 2 fold increase in activity, while A1442P, R1941H, I2012T, I2020T and G2385R result in a decrease in activity.

The mutation, using the numbering of wild type human LRRK2, may alternatively be R1441C, R1441G, Y1699C, R1914H, I2012T, I2020T, or G2385R. LRRK2 with mutations R1441C, R1441G, Y1699C or T2356I is considered to have similar protein kinase activity to wild-type LRRK2. LRRK2 with mutation R1914H or I2012T is considered to be nearly inactive. LRRK2 with mutation I2020T is considered to have activity intermediate between wild-type LRRK2 and LRRK2 with mutation R1914H or I2012T. LRRK2 with mutation G2385R is also considered to be nearly inactive. The activities of further mutants are shown in FIG. 17.

It may be helpful to test compounds against more than one LRRK2 polypeptide; for example against more than one mutant LRRK2 polypeptide. This may assist in deciding on further compounds to design and test.

The LRRK2 polypeptide may be a GST fusion polypeptide, as discussed in Example 1 and in Jaleel et al. (Biochem. J. 405:207-317, 2007) or PCT/GB2008/001211, both of which are incorporated by reference herein in their entirety. For example, the LRRK2 polypeptide may be GST-LRRK2 [1326-2527, G2019S]. Alternative fusion moieties may also be used, as will be well known to those skilled in the art.

It is particularly preferred, although not essential, that the LRRK2 polypeptide has at least 30% of the enzyme activity of full-length human LRRK2 with respect to the phosphorylation of full-length human moesin on residue Thr558 or Thr526; or the phosphorylation of a peptide substrate encompassing such a residue (for example as discussed above; for example RLGRDKYKTLRQIRQ (SEQ ID NO:1) or RLGRDKYKTLRQIRQGNTKQR (SEQ ID NO:2)) or of the substrate polypeptide, as defined above, for example RLGWWRFYTLRRARQGNTKQR (SEQ ID NO:51). It is more preferred if the LRRK2 polypeptide has at least 50%, preferably at least 70% and more preferably at least 90% of the enzyme activity of full-length human LRRK2 with respect to the phosphorylation of full-length human moesin on residue Thr558 or Thr526; or the phosphorylation of a peptide substrate encompassing such a residue, as discussed above, or of the substrate polypeptide, for example RLGW-WRFYTLRRARQGNTKQR (SEQ ID NO:51).

Accession numbers for mammalian LRRK2 sequences in the NCBI database include:
AAV63975.1 human
XP_001168494.1 *Pan troglodytes* (chimpanzee)
XP_615760.3 *Bos taurus* (domestic cow)
XP_543734.2 *Canis familiaris* (dog)
NP_080006.2 *Mus musculus* (mouse)
XP_235581.4 *Rattus norvegicus* (rat)

Numerous further examples of mammalian and non-mammalian LRRK2 polypeptide sequences can be accessed in the sequence databases accessible from the NCBI Medline™ service, as will be well known to the person skilled in the art.

The term "variants" of a polypeptide includes insertions, deletions and substitutions, either conservative or non-conservative. In particular, the term includes variants of the polypeptide where such changes do not substantially alter the protein kinase activity or ability to be phosphorylated, as appropriate. The skilled person will readily be able to design and test appropriate variants, based on, for example, comparison of sequences of examples of each polypeptide, for example from different species. The skilled person will readily be able to determine where insertions or deletions can be made; or which residues can appropriately be left unchanged; replaced by a conservative substitution; or replaced by a non-conservative substitution. The variant polypeptides can readily be tested, for example as described in the Examples.

By "conservative substitutions" is intended combinations such as Gly, Ala; Val, Ile, Leu; Asp, Glu; Asn, Gln; Ser, Thr; Lys, Arg; and Phe, Tyr.

The three-letter or one letter amino acid code of the IUPAC-IUB Biochemical Nomenclature Commission is used herein. It is preferred that at least the amino acids corresponding to the consensus sequences defined herein are L-amino acids.

It is particularly preferred if the polypeptide variant has an amino acid sequence which has at least 65% identity with the amino acid sequence of the relevant human polypeptide, more preferably at least 70%, 71%, 72%, 73% or 74%, still more preferably at least 75%, yet still more preferably at least 80%, in further preference at least 85%, in still further preference at least 90% and most preferably at least 95% or 97% identity with the amino acid sequence of the relevant human polypeptide.

It is still further preferred if a protein kinase variant has an amino acid sequence which has at least 65% identity with the amino acid sequence of the catalytic domain of the human polypeptide, more preferably at least 70%, 71%, 72%, 73% or 74%, still more preferably at least 75%, yet still more preferably at least 80%, in further preference at least 83 or 85%, in still further preference at least 90% and most preferably at least 95% or 97% identity with the relevant human amino acid sequence.

It will be appreciated that the catalytic domain of a protein kinase-related polypeptide may be readily identified by a person skilled in the art, for example using sequence comparisons as described below. Protein kinases show a conserved catalytic core. This core folds into a small N-terminal lobe largely comprising anti-parallel β-sheet, and a large C-terminal lobe which is mostly α-helical.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., 1994). The parameters used may be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

The alignment may alternatively be carried out using the programs T-Coffee, or EMBOSS, as discussed in the Examples.

The residue corresponding (equivalent) to, for example, Thr558 of full-length human moesin may be identified by alignment of the sequence of the polypeptide with that of full-length human moesin in such a way as to maximise the match between the sequences. The alignment may be carried out by visual inspection and/or by the use of suitable computer programs, for example the GAP program of the University of Wisconsin Genetic Computing Group, which will also allow the percent identity of the polypeptides to be calculated. Thus, residues identified in this manner are also "corresponding residues".

It will be appreciated that in the case of truncated forms of (for example) moesin or in forms where simple replacements of amino acids have occurred it is facile to identify the "corresponding residue".

It is preferred that the polypeptides used in the screen are mammalian, preferably human (or a species useful in agriculture or as a domesticated or companion animal, for example dog, cat, horse, cow), including naturally occurring allelic variants (including splice variants). The polypeptides used in the screen may comprise a GST (glutathione S-transferase) portion or may be biotinylated or otherwise tagged, for example with a 6His, HA, myc or other epitope tag, as known to those skilled in the art, or as described in the Examples. This may be useful in purifying and/or detecting the polypeptide(s).

The effect of the compound may be determined by comparing the rate or degree of phosphorylation of the substrate polypeptide by the LRRK2 polypeptide in the presence of different concentrations of the compound, for example in the absence and in the presence of the compound, for example at a concentration of about 100 μM, 30 μM, 10 μM, 3 μM, 1 μM, 0.1 μM, 0.01 μM and/or 0.001 μM.

It is considered that a compound identified by a method of the invention modulates the ability of the LRRK2 polypeptide to phosphorylate different substrates, for example moesin, radixin or ezrin or the peptide substrate RLGRDKYKTLR-QIRQ (SEQ ID NO:1) or RLGRDKYKTLRQIRQGNTKQR (SEQ ID NO:2). The extent of modulation may be different for different substrates. Thus, it may be desirable, but not essential, to test the effect of a compound identified by a method of the invention on the ability of the LRRK2 polypeptide to phosphorylate a polypeptide of interest, for example an endogenous polypeptide, for example moesin, radixin or ezrin.

The method is useful in identifying compounds that modulate, for example inhibit, the protein kinase activity of LRRK2 or the phosphorylation of an ERM family polypeptide by LRRK2. A compound that modulates, for example inhibits, the protein kinase activity of LRRK2 or the phosphorylation of an ERM family polypeptide by LRRK2 may be useful in the treatment of Parkinson's Disease (for example idiopathic Parkinson's Disease or late-onset Parkinson's Disease) or Parkinsonism.

A further substrate for LRRK2, has been developed and utilised in developing a robust and quantitative assay for LRRK2, useful for, for example, assessing the effect of test compounds on LRRK2 activity.

Disclosed herein is a method for identifying a compound expected to be useful in modulating, for example inhibiting, LRRK2 protein kinase activity, the method comprising the steps of (1) determining whether a test compound modulates, for example inhibits, the protein kinase activity of a LRRK2 polypeptide on a substrate polypeptide and (2) selecting a compound which modulates, for example inhibits, the said LRRK2 polypeptide protein kinase activity, wherein the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52).

As an alternative to the sequence (W/F/R/K)(W/F/R/K)(R/K)(F/W/H/R)(Y/W/R)(S/T) (L/V/I)(R/K)(R/K)(A/Y) (SEQ ID NO:52), in all aspects of the invention, the substrate polypeptide may comprise the sequence (W/F/R/K)(W/F/R/K)(R/K)(F/W/H/R)(Y/W/R)(S/T)(L/V/I)(R/K) (R/K)(A/Y) (SEQ ID NO:52) with one, two or three conservative or non-conservative substitutions of residues other than the T/S residue. Thus, up to three residues may differ from the indicated sequences in all aspects of the invention.

The protein kinase activity of the LRRK2 polypeptide that is modulated/assessed in the screening method is phosphorylation of a substrate polypeptide as defined above. Phosphorylation of the substrate polypeptide may be assessed by techniques including those discussed further below and in the Examples. For example, antibodies specific for a phosphorylated (or unphosphorylated) phosphorylation site of the substrate polypeptide may be used in assessing phosphorylation of that phosphorylation site, as well known to those skilled in the art. Further methods will be apparent to the skilled person on the basis of this teaching and the many known methods of assessing protein phosphorylation.

Substrate polypeptide phosphorylation may be assessed in vitro or in a cell, for example by assessing phosphorylation of the substrate polypeptide following immunoprecipitation of the substrate polypeptide from the cellular material, for example following incubation of the cell with $^{32}$P- or $^{33}$P-γ-labelled ATP.

A compound that modulates, for example inhibits, the protein kinase activity of LRRK2 or the phosphorylation of an ERM family polypeptide, for example moesin, may also be useful in other neurodegenerative conditions.

The compound may be one which binds to or near a region of contact between a LRRK2 polypeptide and a substrate or ERM family polypeptide, or may be one which binds to another region and, for example, induces a conformational or allosteric change which stabilises (or destabilises) the complex; or promotes (or inhibits) its formation. The compound may bind to the LRRK2 polypeptide or to the substrate or ERM polypeptide so as to increase the LRRK2 polypeptide protein kinase activity by an allosteric effect. This allosteric effect may be an allosteric effect that is involved in the natural regulation of the LRRK2 polypeptide's activity.

The compounds identified in the methods may themselves be useful as a drug or they may represent lead compounds for the design and synthesis of more efficacious compounds.

The compound may be a drug-like compound or lead compound for the development of a drug-like compound for each of the above methods of identifying a compound. It will be appreciated that the said methods may be useful as screening assays in the development of pharmaceutical compounds or drugs, as well known to those skilled in the art.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons. A drug-like compound may additionally exhibit features of selective interaction with a particular protein or proteins and be bioavailable and/or able to penetrate cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, difficult to synthesise or has poor bioavailability) may provide a starting-point for the design of other compounds that may have more desirable characteristics.

It will be understood that it will be desirable to identify compounds that may modulate the activity of the protein kinase in vivo. Thus it will be understood that reagents and conditions used in the method may be chosen such that the interactions between, for example, the LRRK2 polypeptide and the substrate or ERM family polypeptide, for example moesin, radixin or ezrin polypeptide, are substantially the same as between the human LRRK2 and human substrate or ERM family polypeptide, for example moesin, radixin or ezrin polypeptide. It will be appreciated that the compound may bind to the LRRK2 polypeptide, or may bind to the substrate or ERM family polypeptide.

The compounds that are tested in the screening methods of the assay or in other assays in which the ability of a compound to modulate the protein kinase activity of a protein kinase, for example an LRRK2 polypeptide, may be measured, may be (but do not have to be) compounds that have been selected and/or designed (including modified) using molecular modelling techniques, for example using computer techniques. The selected or designed compound may be synthesised (if not already synthesised) and tested for its effect on the LRRK2 polypeptide, for example its effect on the protein kinase activity. The compound may be tested in a screening method of the invention.

The compounds that are tested may be compounds that are already considered likely to be able to modulate the activity of a protein kinase; or may be compounds that have not been selected on the basis of being likely to modulate the activity of a protein kinase. Thus, the compounds tested may be compounds forming at least part of a general, unselected compound bank; or may alternatively be compounds forming at least part of a pre-selected compound bank, for example a bank of compounds pre-selected on the basis of being considered likely to modulate the activity of a protein kinase.

It will be appreciated that screening assays which are capable of high throughput operation will be particularly preferred. For example, assays using a substrate peptide based on one of the moesin phosphorylation sites, for example using an antibody binding to the phosphorylated form of the peptide but not the unphosphorylated form (or vice versa) may be suitable. Examples may include cell based assays and protein-protein binding assays. A further example is an SPA-based (Scintillation Proximity Assay; Amersham International) system as well known to those skilled in the art. For example, beads comprising scintillant and a substrate polypeptide, for example substrate polypeptide or an ERM family peptide substrate such as RLGWWRFYTLRRAR-QGNTKQR (SEQ ID NO:51) as discussed above may be prepared. The beads may be mixed with a sample comprising $^{32}$P- or $^{33}$P-γ-labelled ATP, a LRRK2 polypeptide and with the test compound. Conveniently this is done in a 96-well format. The plate is then counted using a suitable scintillation counter, using known parameters for $^{32}$P or $^{33}$P SPA assays. Only $^{32}$P or $^{33}$P that is in proximity to the scintillant, i.e. only that bound to the substrate that is bound to the beads, is detected. Variants of such an assay, for example in which the substrate polypeptide is immobilised on the scintillant beads via binding to an antibody or antibody fragment, may also be used. High throughput protein kinase activity assays are well known to those skilled in the art and can be readily adapted in view of the information provided herein on the phosphorylation of substrate or ERM polypeptides by LRRK2 polypeptides.

The screening method may further comprise the step of assessing whether the compound modulates ERM family polypeptide, for example moesin, phosphorylation (or other parameter, for example actin binding or membrane component binding or cell characteristics, as discussed in Jaleel et al (2007) or PCT/GB2008/001211) in a whole cell, tissue or organism; and selecting a compound that modulates the phosphorylation (or other parameter). The compounds may be tested in whole cells, tissue or organisms that have an LRRK2 mutation linked to Parkinson's Disease, as discussed above; or that otherwise over-express LRRK2. The compounds may be tested, for example, in a neuronal cell line. Thus, the effect of the compound on phosphorylation of an ERM family polypeptide, for example moesin, may be assessed in a neuronal cell line.

Figure 22:
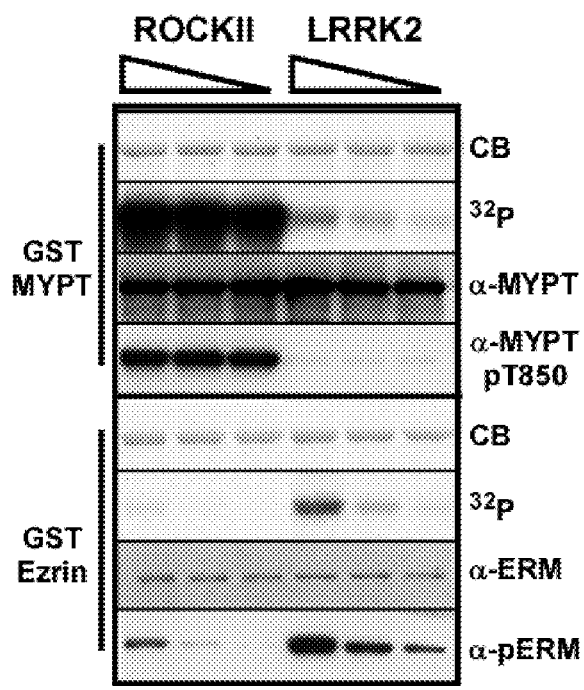
FIG. 22 depicts that LRRK2 does not phosphorylate MYPT (130-kDa regulatory myosin-binding subunit). Recombinant GST-MYPT and heat denatured, GST-full length ezrin were subjected to in vitro kinase reactions with increasing amounts of Rock or LRRK2 in the presence of [γ-$^{32}$P] ATP. Reaction products were analyzed by SDS-PAGE followed by coomassie blue staining and autoradiography or immunoblot with total MYPT and phospho-MYPT Thr850 for MYPT kinase reactions or total ERM and phospho-ERM for ezrin kinase reactions. The known MYPT Rock phosphorylation site contains an Arg at the -2 position and a Gly at the +2 position (Table 1). If LRRK2 prefers a hydrophobic residue at the −2 and a basic reside at the +2, then MYPT should serve as a poor substrate for LRRK2. MYPT is a much better substrate for Rock than for LRRK2, supporting the mutagenesis data.
Figures 23A, 23B:
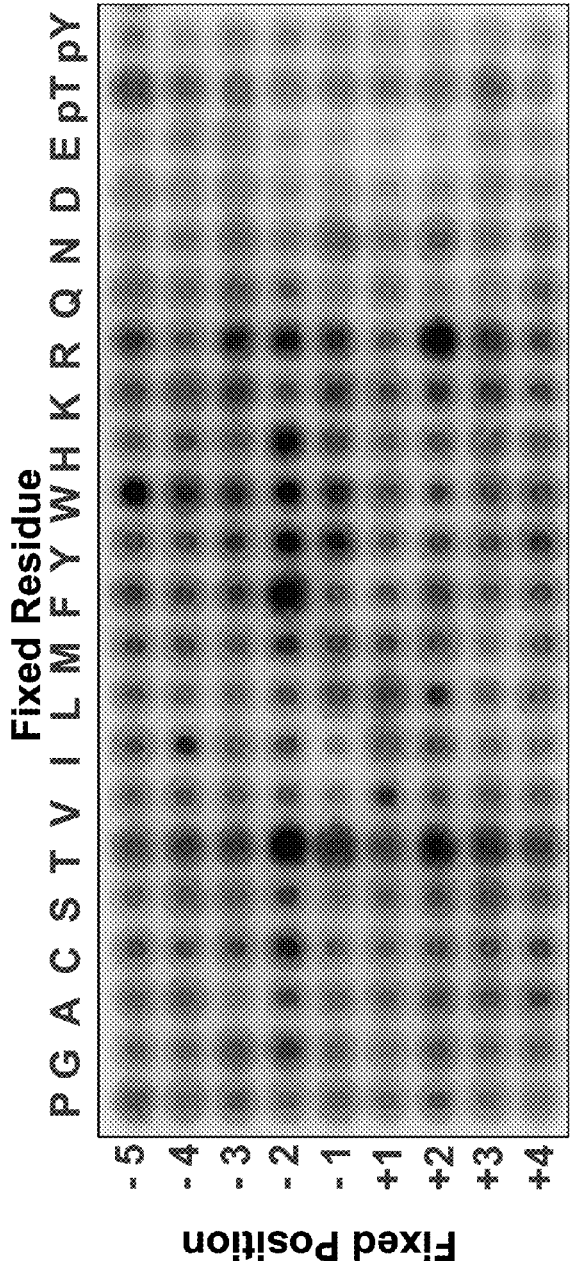
FIG. 23A depicts GST tagged, 1326-End recombinant LRRK2 G2019S purified from transfected HEK293 cells as described in Jaleel et al., Biochemistry 2007. This enzyme was used to determine the peptide substrate preference as described in Hutti et al., Nat. Methods. 2004. Residue preferences were derived from digital quantitation of reaction products and values are shown in FIG. 23B. Control reactions were performed with a kinase dead preparation (FIG. 23C).
Figure 23C:
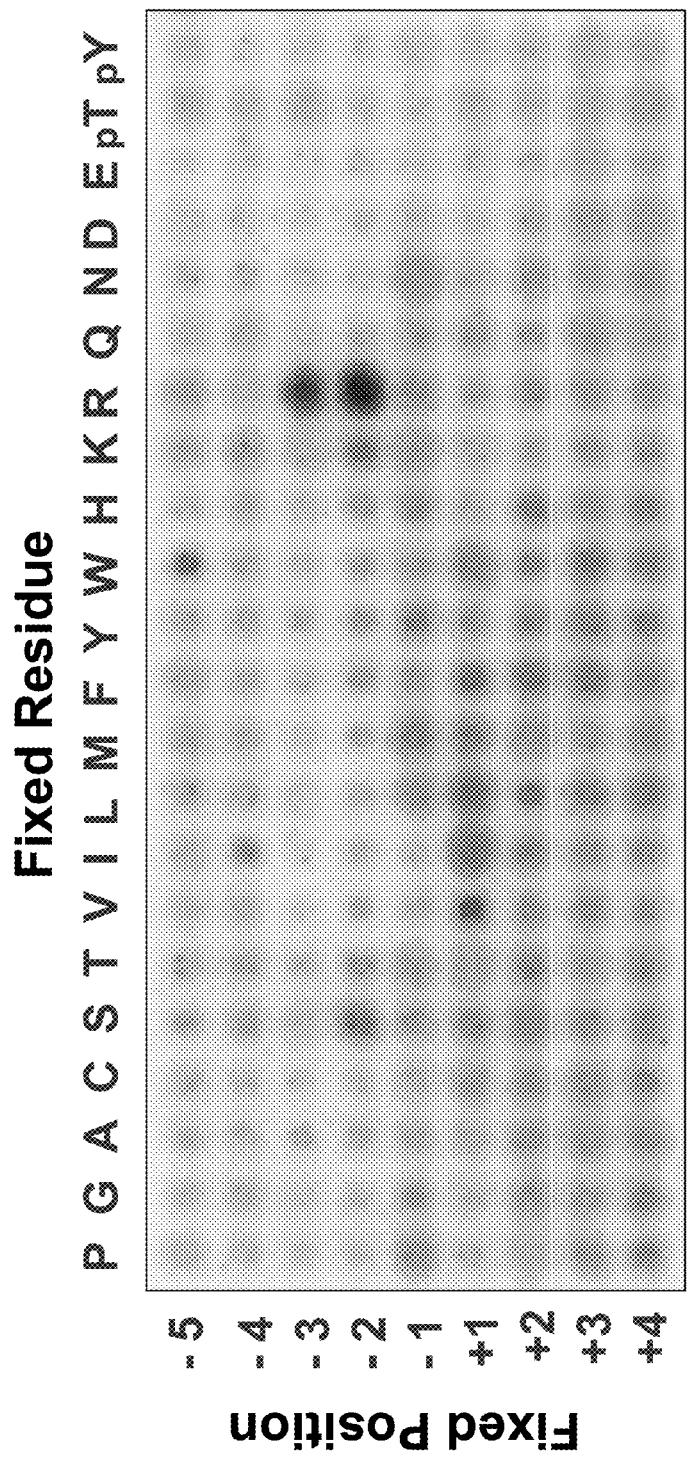

As will be apparent to those skilled in the art, it may be desirable to assess what effect the compound has on other protein kinases. For example, it may be desirable to assess the effect of the compound on phosphorylation of substrates of other protein kinases, for example substrates of RockII, in order to distinguish between LRRK2 and ROCK inhibitors. For example, as shown in, for example, FIGS. 20 and 22 the substrate preferences of LRRK2 and Rock-II are different. As an example, LRRK2 does not phosphorylate MYPT, while RockII does phosphorylate MYPT.

The screening method may still further comprise the step of assessing whether the compound modulates the activity of LRRK2, in the whole cell, tissue or organism, and selecting a compound that modulates the activity selected.

Information on PD models, biomarkers and assessment techniques, in/against which it may be appropriate further to test compounds identified using the screening methods described herein, can be found at, for example, the following links, which are representative of information available to those skilled in the art.

http://www.ninds.nih.gov/about_ninds/plans/nihparkinsons_agenda.htm#Models
http://www.sciencedaily.com/releases/2006/07/060729134653.htm (mouse model with mitochondrial disturbance)
http://www.sciencedaily.com/releases/2004/10/041005074846.htm (embryonic stem cell model)
http//en.wikipedia.org/wiki/Parkinson's_disease PD animal models include the 6-hydroxydopamine treated rodent and the MPTP (1-methyl-4-phenyl-1,2,3,6-tetrahydropyridine)-treated primate. Both are based on toxic destruction of dopaminergic brain cells (and some other types), and usually employ young, otherwise healthy animals. Because these models reproduce some key features of Parkinson's disease, they are considered useful to test emerging new therapies.

Compounds may also be subjected to other tests, for example toxicology or metabolism tests, as is well known to those skilled in the art.

The screening method of the invention may comprise the step of synthesising, purifying and/or formulating the selected compound.

TABLE 1

Known substrates of rho associated kinase (Rock).

| Protein | Phosph. site | N'−6 | −5 | −4 | −3 | −2 | −1 | PHOS | .+1 | .+2 | .+3 | .+4 | .+5 | .+6 |
|---|---|---|---|---|---|---|---|---|---|---|---|---|---|---|
| Calponin | Thr-170 | I | G | L | Q | M | G | T | N | K | F | A | S | Q |
| Calponin | Thr184 | Q | M | T | A | Y | G | T | R | R | H | L | Y | D |
| LIMK | Thr 508 | D | R | K | K | R | Y | T | V | V | Q | N | P | Y |
| Adducin | Thr 445 | K | Q | Q | R | E | K | T | R | W | L | N | S | G |
| Int. Filaments | | | | | | | | | | | | | | | |
| Vimentin | Ser 71 | S | A | V | R | L | R | S | S | V | P | G | V | P |
| Neurofilament-1 | Ser 57 | S | V | R | R | S | Y | S | S | S | S | G | S | L |
| GFAP | Thr 7 | M | E | R | R | R | I | T | S | A | A | R | R | S |
| GFAP | Ser13 | T | S | A | A | R | R | S | Y | V | S | S | G | E |
| GFAP | Ser 34 | G | P | G | T | R | L | S | L | A | R | M | P | P |
| CRMP-2 | Thr 555 | N | I | P | R | R | T | T | Q | R | I | V | A | P |
| Tau | Thr 245 | A | K | S | R | L | Q | T | A | P | V | P | M | P |
| Tau | Thr 377 | I | E | T | H | K | L | T | F | R | E | N | A | R |
| Tau | Ser 409 | T | S | P | R | H | L | S | N | V | S | S | S | G |
| MAP2 | Ser 1796 | A | S | P | R | R | L | S | N | V | S | S | S | G |
| Ezrin/Radixin/Moesin | Thr567/564/558 | G | R | D | K | Y | K | T | L | R | Q | I | R | Q |
| MYPT (MBS) | Ser 850 | P | R | E | K | R | R | S | T | G | V | S | F | W |

TABLE 1-continued

Known substrates of rho associated kinase (Rock).

| Protein | Phosph. site | N'-6 | -5 | -4 | -3 | -2 | -1 | PHOS | .+1 | .+2 | .+3 | .+4 | .+5 | .+6 |
|---------|--------------|------|----|----|----|----|----|------|-----|-----|-----|-----|-----|-----|
| MLC | Ser 19 | R | P | Q | R | A | T | S | N | V | F | A | M | F |
| MARKS | Ser 159 | K | K | K | K | R | F | S | F | K | K | S | F | K |
| Merlin T567 | | G | S | S | K | H | N | T | I | K | K | L | Y | L |

Table, adapted from Kang et al. (Biochimie 89. p. 39-47 2007), showing the known Rock substrate phosphorylation sites. Merlin is an ezrin, radixin, moesin (ERM) related protein with an analogous, but degenerate, site to the T558 of moesin.

The disclosure also provides a method for preparing a compound which modulates the activity of LRRK2 or the phosphorylation of an ERM polypeptide, the method comprising 1) performing an appropriate screening method of the invention 2) synthesising, purifying and/or formulating the selected compound.

The compound may be formulated for pharmaceutical use, for example for use in in vivo trials in animals or humans.

A further embodiment is a compound identified or identifiable by a screening method disclosed herein.

A still further embodiment is a compound of the invention for use in medicine. A still further embodiment is a compound for treating Parkinson's Disease (for example idiopathic Parkinson's Disease or late-onset Parkinson's Disease) or Parkinsonism.

The compound may be administered in any suitable way, usually parenterally, for example intravenously, intraperitoneally, subcutaneous or intramuscular or intravesically, in standard sterile, non-pyrogenic formulations of diluents and carriers. The compound may also be administered topically. The compound may also be administered in a localised manner, for example by injection. The treatment may consist of a single dose or a plurality of doses over a period of time. The compound may be useful in treating patients with or at risk of Parkinson's Disease or Parkinsonism.

Whilst it is possible for a compound disclosed herein to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

Thus, also provided are pharmaceutical compositions comprising a compound identified or identifiable by the screening methods disclosed herein and a pharmaceutically acceptable carrier and optionally other therapeutic agents.

The composition may also comprise or be administered with a further compound useful in treating Parkinson's Disease or Parkinsonism or other neurodegenerative condition, as appropriate.

A further embodiment provides a purified preparation or kit of parts comprising an LRRK2 polypeptide (for example as discussed above) or polynucleotide (i.e., a polynucleotide encoding an LRRK2 polypeptide) and an ERM family polypeptide (for example as discussed above) or polynucleotide (i.e., a polynucleotide encoding an ERM family polypeptide). A further aspect of the invention provides a purified preparation or kit of parts comprising an LRRK2 polypeptide or polynucleotide (i.e., a polynucleotide encoding an LRRK2 polypeptide) or antibody useful in preparing LRRK2, for example as discussed briefly herein; and a substrate polypeptide as defined above (or a polynucleotide encoding a substrate polypeptide). The preparation or kit may, for example, comprise a recombinant LRRK2 polynucleotide or polypeptide and a recombinant or chemically synthesised substrate polypeptide. The kit may further comprise an ERM family polypeptide or a fragment derivable from an ERM family polypeptide, for example moesin, radixin or ezrin, which encompasses the residue corresponding to Thr558 residue of moesin and at least part of the surrounding sequence which includes this residue, for example at least the 2, 3, 4, 5, 6 or 7 residues C-terminal and N-terminal of this residue; for example the polypeptide RLGRDKYKTLRQIRQ (SEQ ID NO:1) or RLGRDKYK-TLRQIRQGNTKQR (SEQ ID NO:2); or a polypeptide of less than 100, 80, 60, 50, 40, 30, 25, 20, 19, 18, 17 or 16 amino acids, comprising the amino acid sequence RLGRDKYK(T/S)LRQIRQ (SEQ ID NO:3) or RLGRDKYK(T/S)LR-QIRQGNTKQR (SEQ ID NO:4), each with no or up to one, two, three, four, five, six, seven, eight, nine or ten conservative or non-conservative substitutions of residues other than the T/S residue, as discussed above.

The preparation or kit may be useful in an assay as disclosed herein.

Figure 29:
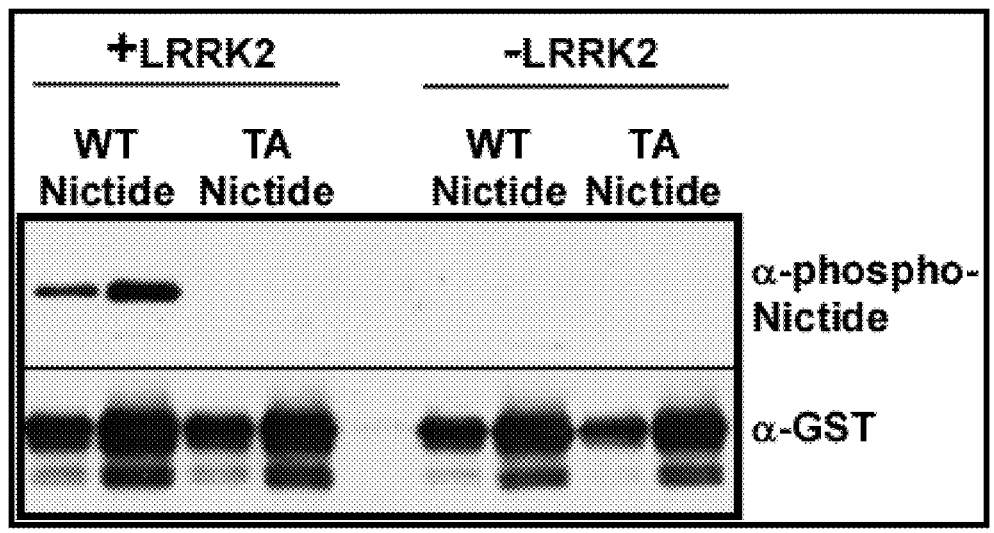
FIG. 29 depicts phosphorylation of Nictide assessed using an antibody raised against a phospho-Nictide antigen. GST fusion proteins with either the wild-type Nictide sequence or the phosphorylation site mutated to alanine were produced in bacteria (GST-RLGWWRFYTLRRARQGNTKQR (SEQ ID NO:51) or GST-RLGWWRFYALRRARQGNTKQR (SEQ ID NO:53)). These proteins were subjected to kinase reactions containing LRRK2 (293 cell expressed GST tagged 1326-END G2019S) or buffer. A titration of these reactions containing 66 or 330 ng of the GST fusion was probed with an antibody raised against a phospho-Nictide antigen. Immunoblots were performed in the presence of 10 ug/ml dephospho Nictide.

The kit may further comprise a specific binding partner, typically an antibody, that binds in a phosphorylation state-sensitive manner to an epitope encompassing the phosphorylable residue of the substrate polypeptide, for example Thr558 or Thr526 of moesin (for example human moesin) or corresponding portion of another ERM polypeptide, for example radixin or ezrin. By "binding in a phosphorylation state-sensitive manner" is included the meaning that the specific binding partner is capable of binding to the epitope (or substrate polypeptide comprising the epitope) when phosphorylated on the phosphorylatable portion, but is not capable of binding to the epitope (or substrate polypeptide comprising the epitope) when it is not phosphorylated on the phosphorylatable portion of that epitope. Thus, it is preferred that the specific binding partner has at least a 5-fold, preferably 10, 20, 50, 100, 200, 500, 1000, 2000 or 5000-fold difference in affinity for the phosphorylated and non-phosphorylated ERM family polypeptide. In practice, a specific binding partner prepared and purified/selected using methods known in the art (see, for example, WO 03/087400; for example affinity purified using a phosphorylated peptide affinity column and a nonphosphorylated peptide affinity column; WO 03/087400 in incorporated by reference herein for all it discloses regarding purification methods) is expected to have the required affinity and specificity of binding. An example of such an antibody prepared using these techniques is described/used in FIG. 29.

By the term "antibody" is included synthetic antibodies and fragments and variants (for example as discussed above) of whole antibodies which retain the antigen binding site. The antibody may be a monoclonal antibody, but may also be a polyclonal antibody preparation, a part or parts thereof (for example an Fab fragment or F(ab')$_2$) or a synthetic antibody or part thereof. Fab, Fv, ScFv and dAb antibody fragments can all be expressed in and secreted from E. coli, thus allowing the facile production of large amounts of the said fragments. By "ScFv molecules" is meant molecules wherein the $V_H$ and $V_L$ partner domains are linked via a flexible oligopeptide. IgG class antibodies are preferred.

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: techniques and Applications", JGR Hurrell (CRC Press, 1982) both of which are incorporated by reference herein for all they disclose regarding monoclonal antibodies, modified as indicated above. Bispecific antibodies may be prepared by cell fusion, by reassociation of monovalent fragments or by chemical cross-linking of whole antibodies. Methods for preparing bispecific antibodies are disclosed in Corvalen et al, (1987) *Cancer Immunol. Immunother.* 24, 127-132 and 133-137 and 138-143, which is incorporated by reference herein for all it discloses regarding bispecific antibodies.

A general review of the techniques involved in the synthesis of antibody fragments which retain their specific binding sites is to be found in Winter & Milstein (1991) *Nature* 349, 293-299, which is incorporated by reference herein for all it discloses regarding antibody fragments.

By "purifed" is meant that the preparation has been at least partially separated from other components in the presence of which it has been formed, for example other components of a recombinant cell. Examples of methods of purification that may be used are described in the Examples or in Jaleel et al. (2007) or PCT/GB2008/001211.

The preparation may be substantially pure. By "substantially pure" it is meant that the said polypeptide(s) are substantially free of other proteins. Thus, included herein is any composition that includes at least 2, 3, 4, 5, 10, 15, 20 or 30% of the protein content by weight as the said polypeptides, preferably at least 50%, more preferably at least 70%, still more preferably at least 90% and most preferably at least 95% of the protein content is the said polypeptides.

Thus, also included are compositions comprising the said polypeptides and a contaminant wherein the contaminant comprises less than 96, 95, 94, 90, 85, 80 or 70% of the composition by weight, preferably less than 50% of the composition, more preferably less than 30% of the composition, still more preferably less than 10% of the composition and most preferably less than 5% of the composition by weight.

Also included are the substantially pure said polypeptides when combined with other components ex vivo, said other components not being all of the components found in the cell in which said polypeptides are found.

A further embodiment provides a recombinant cell capable of expressing a LRRK2 polypeptide and a substrate or ERM family polypeptide. The cell may comprise a recombinant LRRK2 polynucleotide and a recombinant substrate or ERM family polynucleotide. The substrate polypeptide may comprise a tag or a further portion considered to bind to or co-localise with LRRK2, for example an ERM family polypeptide or fragment, as discussed above. The cell may be capable of overexpressing the LRRK2 polypeptide and/or substrate or ERM family polypeptide from the endogenous sequence encoding the said polypeptide, for example using techniques of sequence-specific targeting of transcription activators. Thus the cell may be modified in a way intended to lead to increased expression of at least one of the LRRK2 polypeptide and substrate or ERM family polypeptide relative to a cell which has not been so modified. The cell may be a prokaryotic or eukaryotic cell. For example it may be a eukaryotic cell, for example an insect, yeast or mammalian cell, for example a human cell. Examples of suitable cells are described, for example, in the Examples or in Jaleel et al. (2007) or PCT/GB2008/001211.

The recombinant nucleic acid is preferably suitable for expressing the encoded polypeptide. The recombinant nucleic acid may be in the form of an expression vector. Recombinant polynucleotides suitable for expressing a given polypeptide are well known to those skilled in the art, and examples are described in the Examples or in Jaleel et al. (2007) or PCT/GB2008/001211.

A further embodiment provides a recombinant cell comprising a LRRK2 polypeptide and a substrate or ERM family polypeptide. The cell may comprise a recombinant LRRK2 polypeptide and a recombinant substrate or ERM family polypeptide. The cell may be a cell according to the preceding disclosure. The cell may comprise at least 1.1, 1.2, 1.5, 2, 3, 5, 10 or 20-fold more LRRK2 polypeptide (and/or substrate or ERM family polypeptide) than an equivalent cell which has not been modified in order to overexpress the LRRK2 polypeptide or to express the recombinant LRRK2 polypeptide.

By "suitable for expressing" is meant that the polynucleotide is a polynucleotide that may be translated to form the polypeptide, for example RNA, or that the polynucleotide (which is preferably DNA) encoding the polypeptide of the invention is inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

Characteristics of vectors suitable for replication in mammalian/eukaryotic cells are well known to those skilled in the art, and examples are given below. It will be appreciated that a vector may be suitable for replication in both prokaryotic and eukaryotic cells.

A variety of methods have been developed to operably link polynucleotides, especially DNA, to vectors for example via complementary cohesive termini. Suitable methods are described in Sambrook et al (1989) *Molecular Cloning, A Laboratory Manual*, Cold Spring Harbor Laboratory, Cold Spring Harbor, N.Y., incorporated by reference herein for all it discloses regarding recombinant DNA methods.

A desirable way to modify the DNA encoding a polypeptide is to use the polymerase chain reaction (PCR). This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued 3 Apr. 1984 to Rutter et al, 4,530,901 issued 23 Jul. 1985 to Weissman, 4,582,800 issued 15 Apr. 1986 to Crowl, 4,677,063 issued 30 Jun. 1987 to Mark et al, 4,678,751 issued 7 Jul. 1987 to Goeddel, 4,704,362 issued 3 Nov. 1987 to Itakura et al, 4,710,463 issued 1 Dec. 1987 to Murray, 4,757,006 issued 12 Jul. 1988 to Toole, Jr. et al, 4,766,075 issued 23 Aug. 1988 to Goeddel et al and 4,810,648 issued 7 Mar. 1989 to Stalker, all of which are incorporated herein by reference.

The DNA (or in the case of retroviral vectors, RNA) encoding the polypeptide may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by recombinant DNA are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL, available from Pharmacia. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic cell line. Yeast host cells include YPH499, YPH500 and YPH501 which are generally available from Stratagene Cloning Systems. Preferred mammalian host cells include human embryonic kidney 293 cells (see Example 1), Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Transformation of appropriate cell hosts with a DNA construct is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y., both incorporated by reference herein for all they disclose regarding transformation of prokaryotic host cells. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. Both of these references are incorporated by reference herein for all they disclose regarding transformation of yeast cells With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells.

For example, many bacterial species may be transformed by the methods described in Luchansky et al (1988) *Mol. Microbiol.* 2, 637-646 incorporated herein by reference for all it discloses regarding transformation of bacterial cells. The greatest number of transformants is consistently recovered following electroporation of the DNA-cell mixture suspended in 2.5×PEB using 6250V per cm at 25:FD.

Methods for transformation of yeast by electroporation are disclosed in Becker & Guarente (1990) *Methods Enzymol.* 194, 182 incorporated by reference herein for all it discloses regarding transformation of yeast cells Successfully transformed cells, i.e. cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using well-known methods.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present disclosure also contemplates a culture of those cells, preferably a monoclonal (clonally homogeneous) culture, or a culture derived from a monoclonal culture, in a nutrient medium.

A further embodiment provides a method for making a preparation comprising the step of purifying the preparation from a cell. Methods of cultivating host cells and isolating recombinant proteins are well known in the art. Examples of suitable purification techniques are described in the Examples. For example, one or more component of the preparation may be tagged so as to aid purification using affinity reagents, as will be well known to those skilled in the art and as described in the Examples. Chromatographic techniques may also be used, for example as described in the Examples. A further embodiment provides a preparation obtained or obtainable by this method. The preparation may comprise, for example, a tagged LRRK2 polypeptide and an ERM family polypeptide.

The methods disclosed herein may be performed with the LRRK2 polypeptide and substrate or ERM family polypeptide in the form of a preparation or a preparation or complex obtained or obtainable by the method as indicated above; or in a cell.

The above polypeptides may be made by methods well known in the art and as described below and in the Examples, for example using molecular biology methods or automated chemical peptide synthesis methods.

It will be appreciated that peptidomimetic compounds may also be useful. Thus, by "polypeptide" or "peptide" are included not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) *J. Immunol.* 159, 3230-3237, incorporated herein by reference. This approach involves making pseudopeptides containing changes involving the backbone, and not the orientation of side chains. Meziere et al show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the CI atoms of the amino acid residues is used; it is particularly preferred if the linker moiety has substantially the same charge distribution and substantially the same planarity as a peptide bond.

It will be appreciated that the peptide may conveniently be blocked at its N- or C-terminus so as to help reduce susceptibility to exoproteolytic digestion.

Thus, it will be appreciated that the LRRK2 or, more preferably, the substrate or ERM family polypeptide may be a peptidomimetic compound.

A kit comprising a recombinant polynucleotide encoding a LRRK2 polypeptide and a recombinant polynucleotide encoding a substrate or an ERM family polypeptide may be useful in forming a preparation or complex which may be useful in, for example a screening method disclosed herein. The recombinant polynucleotide(s) may be in an expression vector (for example as discussed above) or (less desirably) useful for in vitro expression. The ERM family polypeptide may be a peptide encompassing human moesin residue Thr558, as discussed above.

A further aspect of the invention provides a polypeptide comprising the sequence (W/F/R/K)(W/F/R/K)(R/K)(F/W/H/R)(Y/W/R)(S/T)(L/V/I)(R/K)(R/K)(A/Y) (SEQ ID NO:52) (or alternatively comprising the sequence (W/F/R/K) (W/F/R/K)(R/K)(F/W/H/R)(Y/W/R)(S/T)(L/V/I) (R/K)(R/K)(A/Y) (SEQ ID NO:52) with one, two or three conservative or non-conservative substitutions of residues other than the T/S residue). Such a polypeptide is considered to be a substrate for LRRK2, as discussed above. Preferences for the substrate polypeptide are as indicated above.

A further embodiment provides a truncated LRRK2 polypeptide of less than 2000 amino acids having protein kinase activity on a substrate ERM family polypeptide (for example the peptide encompassing human moesin residue Thr558 as discussed above), comprising at least the GTPase domain, COR domain, kinase domain, WD40-like motif and C-terminal tail residues of wild type human LRRK2 or a variant or naturally occurring mutant thereof. The truncated LRRK2 polypeptide may not comprise the Leucine Rich Repeat (LRR) motif. The truncated LRRK2 polypeptide may comprise, or consist of, at least residues 1326-2527 of wild type human LRRK2 or a variant or naturally occurring mutant thereof. As noted above, it is considered that truncation at the C-terminus may adversely effect the protein kinase activity of the truncated LRRK2 polypeptide, whilst truncation at the N-terminus of the fragment may be better tolerated. Thus, the N-terminus of the truncated LRRK2 polypeptide may alternatively lie after residue 1326, for example between residue 1326 and about residue 1336.

Thus, examples of polypeptides include, but are not limited to, LRRK2 polypeptide GST-LRRK2[1326-2527, G2019S] and GST-LRRK2[1326-2527].

A further embodiment provides a substrate polypeptide which is a fragment derivable from an ERM family polypeptide, for example moesin, radixin or ezrin, which encompasses the residue corresponding to Thr558 residue of moesin and at least part of the surrounding sequence which includes this residue, for example at least the 2, 3, 4, 5, 6 or 7 residues C-terminal and N-terminal of this residue; for example the polypeptide RLGRDKYKTLRQIRQ (SEQ ID NO:1) or RLGRDKYKTLRQIRQGNTKQR (SEQ ID NO:2); or a polypeptide of less than 100, 80, 60, 50, 40, 30, 25, 20, 19, 18, 17 or 16 amino acids, comprising the amino acid sequence RLGRDKYK(T/S)LRQIRQ (SEQ ID NO:3) or RLGRD-KYK(T/S)LRQIRQGNTKQR (SEQ ID NO:4), each with no or up to one, two, three, four, five, six, seven, eight, nine or ten conservative or non-conservative substitutions of residues other than the T/S residue, as discussed above.

The substrate polypeptide may consist of the amino acid sequence RLGRDKYK(T/S)LRQIRQ (SEQ ID NO:3) or RLGRDKYK(T/S)LRQIRQGNTKQR (SEQ ID NO:4), each with no or up to one, two, three, four, five, six, seven, eight, nine or ten conservative or non-conservative substitutions of residues other than the T/S residue.

A further embodiment provides a polynucleotide encoding a truncated LRRK2 polypeptide or a polypeptide or peptide disclosed herein. A further embodiment provides a polynucleotide encoding the substrate polypeptide.

The polynucleotide may be a vector suitable for replication and/or expression of the polypeptide in a mammalian/eukaryotic cell. A still further embodiment is a recombinant polynucleotide suitable for expressing a polypeptide disclosed herein. Typically the recombinant polynucleotide comprises a polynucleotide encoding a polypeptide disclosed herein.

The polynucleotide or recombinant polynucleotide may be DNA or RNA, preferably DNA. The polynucleotide may or may not contain introns in the coding sequence; preferably the polynucleotide is or comprises a cDNA.

A further embodiment provides a method of phosphorylating a substrate or ERM family polypeptide wherein the substrate peptide, such as an ERM family polypeptide, is phosphorylated by an LRRK2 polypeptide. The substrate or ERM family polypeptide that is phosphorylated by the method may be partially or fully dephosphorylated substrate or ERM family polypeptide.

A further embodiment provides the use of an LRRK2 polypeptide in a method of phosphorylating a substrate or an ERM family polypeptide. The substrate or ERM family polypeptide may preferably be phosphorylated on the underlined threonine or serine residue.

It will be appreciated that if the substrate or ERM family polypeptide is already phosphorylated, further phosphorylation may not be possible. It will further be appreciated that a substrate or ERM family polypeptide isolated from cells (either as an endogenous or recombinant polypeptide) may be heterogeneous with regard to its phosphorylation state. For example, fully phosphorylated, fully dephosphorylated and/or partially phosphorylated molecules of the substrate or ERM family polypeptides may be present in a single cell or group/culture of cells.

A further embodiment provides a method of characterising an LRKK2 mutant, for example an LRRK2 mutant found in a patient with Parkinson's Disease, the method comprising the step of assessing the ability of the LRKK2 mutant to phosphorylate a substrate ERM family polypeptide. The method may comprise the step of determining the $K_m$ and/or the $V_{max}$ of the LRRK2 mutant for the substrate or ERM family polypeptide. Such characterisation may be useful in investigating mechanisms underlying Parkinson's Disease or Parkinsonism.

A further embodiment provides a method for assessing LRRK2 activity in a sample, the method comprising the step of assessing the ability of the sample to phosphorylate a substrate polypeptide of the invention. The method may comprise the step of determining the $K_m$ and/or the $V_{max}$ of the sample for the substrate polypeptide of the invention. The sample may be, for example, a sample obtained from a patient or may be a sample from a cell culture or a sample taken during an LRRK2 purification protocol, as will be well known to those skilled in the art. The sample may be an immunoprecipitate prepared using an antibody to LRRK2 that allows LRRK2 to retain protein kinase activity, for example as described herein, for example from material obtained from a patient, a cell culture or during a purification protocol.

Examples of methods for assessing the phosphorylation of the substrate polypeptide are discussed above and in the Examples and include methods making use of phosphorylation-specific antibodies, as discussed above.

A further embodiment provides the use of a polypeptide consisting of residues 100 to 498 (or 500) of LRRK2 or a fragment thereof or a fusion either thereof (for example as shown in FIG. 30, for example a fusion with a sequence of less than about 10 amino acids), other than with an LRRK2-derived sequence, in the preparation of an antibody. The antibody typically is able to bind to LRRK2, for example to immunoprecipitate LRRK2 from cellular material, and allows the LRRK2 to retain protein kinase activity. Thus, LRRK2 immunoprecipitated using the antibody typically retains protein kinase activity. As will be apparent to those skilled in the art, in embodiments the polypeptide may be used as an immunogen or may be used in selection or refinement of the antibody. Terminology and examples of methodology relating to antibodies are discussed above. Example 6 indicates fragments of LRRK2 that were tested as immunogens. Only antibodies raised to LRRK2(100-500) as shown in FIG. 30 were found to be useful in immunoprecipitating LRRK2 that retained protein kinase activity.

A further embodiment provides a method of preparing an antibody capable of binding to LRRK2 comprising the step of raising the antibody to, or selecting the antibody on the basis of binding to, a polypeptide consisting of residues 100 to 498 (or 500) of LRRK2 or a fragment thereof or a fusion either thereof (for example as shown in FIG. 30 or as discussed above) other than with an LRRK2-derived sequence. It is considered that such an antibody is capable of immunoprecipitating LRRK2; and that the LRRK2 retains protein kinase activity.

A further embodiment provides an antibody obtained or obtainable by the disclosed methods. A further embodiment provides an antibody binding to a polypeptide consisting of residues 100 to 498 (or 500) of LRRK2 or a fragment thereof or a fusion either thereof (for example as shown in FIG. 30 or as discussed above), other than with an LRRK2-derived sequence.

For these embodiments it may be preferred that the said fragment is not residues 100-190 of LRRK2.

A further embodiment provides the use of an antibody in a method of preparing, assaying or detecting LRRK2. Examples of such uses are mentioned above and in the Examples.

All documents referred to herein are hereby incorporated by reference.

The claimed invention is now described in more detail by reference to the non-limiting Figures and Examples.

Example 1

LRRK2 Phosphorylates Moesin at Thr558; Characterisation of how Parkinson's Disease Mutants Affect Kinase Activity Abbreviations: GST, glutathione S-transferase; KESTREL, KinasE Substrate TRacking and Elucidation; LRRK2, Leucine Repeat Rich Kinase 2; LDS, Lithium dodecyl sulfate; MBP, Myelin basic protein; CRMP2, Collapsin response mediator protein 2; COR, C-terminal Of Ras of complex; PD, Parkinson's disease; GbpC, cGMP binding protein C; RIPK, Rho-Interacting Protein kinase; and ROCK-II, Rho associated kinase-2.

Autosomal dominant mutations in the human Leucine Rich Repeat Kinase-2 (LRRK2) gene cause late-onset Parkinson's disease (PD). LRRK2 is a large ~280 kDa enzyme that, beside a protein kinase domain, contains Leucine Rich Repeats, a GTPase domain, a COR domain and a WD40 motif. Mutations within each of these domains are linked with PD. Little is known about how LRRK2 is regulated, what its physiological substrates are or how mutations affect LRRK2 function. Thus far LRRK2 activity has only been assessed by autophosphorylation and phosphorylation of myelin basic protein (MBP), which is catalysed rather slowly. A KESTREL screen was undertaken in rat brain extracts to identify proteins that were phosphorylated by an activated PD mutant of LRRK2 (G2019S). This led to the finding that a protein termed moesin, that anchors the actin-cytoskeleton to the plasma membrane is efficiently phosphorylated by LRRK2, at Thr558, a previously identified in vivo phosphorylation site that regulates the ability of moesin to bind actin. LRRK2 also phosphorylated a peptide termed LRRKtide, that encompassed Thr558. These findings were used to determine how nine previously reported PD mutations of LRRK2 affected kinase activity. Only one of the mutations analysed, namely G2019S, stimulated kinase activity. Four mutations inhibited LRRK2 kinase activity (R1941H, I2012T, I2020T and G2385R), whereas the remainder (R1441C, R1441G, Y1699C and T2356I), did not influence activity. The minimum catalytically active fragment of LRRK2, requires an intact GTPase, COR and kinase domain as well as WD40 motif and C-terminal tail (comprises residues 1326-2527). The findings presented herein will be useful for the quantitative measurement of LRRK2 kinase activity and for screening for drugs that inhibit LRRK2 for the treatment of PD.

Materials and Methods

Protease-inhibitor cocktail tablets were obtained from Roche; P81 phosphocellulose paper was from Whatman; [$\gamma^{32}$P]-ATP and all protein chromatography media were purchased from Amersham Biosciences. Myelin basic protein (MBP) was from Invitrogen, Precast SDS polyacrylamide Bis-Tris gels were from Invitrogen; tissue culture reagents were from Life Technologies; Millipore Immobilon-P was from Fisher Scientific. Active rat ROCKII [residues 2-543] was expressed in baculovirus by the Division of Signal Transduction Therapy Unit (University of Dundee). The LRRKtide peptide (RLGRDKYKTLRQIRQ; SEQ ID NO:1) was synthesised by Dr Graham Bloomberg at the University of Bristol.

Antibodies. The anti-GST was raised in sheep against the glutathione S-transferase protein. The secondary antibodies coupled to horseradish peroxidase used for immunoblotting were obtained from Pierce.

General methods. Tissue culture, transfection, immunoblotting, restriction enzyme digests, DNA ligations, and other recombinant DNA procedures were performed using standard protocols. All mutagenesis was carried out using the Quick-Change site-directed mutagenesis method (Stratagene). DNA constructs used for transfection were purified from E. coli DH5α using Qiagen plasmid Mega or Maxi kit according to the manufacturer's protocol. All DNA constructs were verified by DNA sequencing, which was performed by The Sequencing Service, School of Life Sciences, University of Dundee, Scotland, UK, using DYEnamic ET terminator chemistry (Amersham Biosciences) on Applied Biosystems automated DNA sequencers.

Buffers. Lysis Buffer contained 50 mM Tris/HCl pH 7.5, 1 mM EGTA, 1 mM EDTA, 1% (w/v) Triton-X100, 1 mM sodium orthovanadate, 10 mM sodium-β-glycerophosphate, 50 mM sodium fluoride, 5 mM sodium pyrophosphate, 0.27 M sucrose, 0.1% (v/v) 2-mercaptoethanol and complete proteinase inhibitor cocktail (one tablet/50 ml, Boehringer). Buffer A contained 50 mM Tris/HCl pH 7.5, 0.1 mM EGTA and 0.1% (v/v) 2-mercaptoethanol. Extraction Buffer contained 50 mM Tris/HCl pH 7.5, 5% (v/v) glycerol, 10 mM 2-mercaptoethanol, 1 mM EDTA, 1 mM EGTA, 0.03% (v/v) Brij-35, complete proteinase inhibitor cocktail (one tablet/50 ml). Sample Buffer was 1× NuPAGE® LDS sample buffer (Invitrogen) containing 1% (by vol) 2-mercaptoethanol.

Plasmids. A full-length cDNA clone encoding LRRK2 corresponded to NCBI Acc. AAV63975. The full length and the fragments of LRRK2 gene were amplified from the LRRK2 cDNA fragment, according to standard PCR methods, using KOD polymerase (Novagen). The resulting PCR products were subcloned into mammalian pEBG2T and pCMV5 expression vectors as Bamh1-Not1 fragments. A cDNA encoding full-length as well as C-terminal fragments of human moesin (NCBI Acc. NP_002435) were amplified by PCR from an EST ordered from Geneservice (IMAGE clone 4908580). The PCR product was ligated into different expression vectors as Not1-Not1 fragments.

Expression and purification of GST-LRRK2. Typically 10 to 100 ten-cm diameter dishes of HEK 293 cells, were cultured and each dish transfected with 5 µg of the pEBG-2T construct encoding wild type or different mutant forms of LRRK2 using the polyethylenimine method. The cells were cultured for a further 36 h and lysed in 0.5 ml of ice-cold lysis buffer, the lysates pooled and centrifuged at 4° C. for 10 min at 26,000×g. The GST-fusion proteins were purified by affinity chromatography on glutathione-Sepharose (10 µl per dish of 293 cells) and were eluted in Buffer A containing 20 mM glutathione and 0.27 M sucrose. The enzyme was snap frozen in small aliquots and stored at −80° C.

LRRK2 KESTREL screen. Brains derived from 50 rats were minced and homogenized with four volumes of Extraction Buffer. Insoluble material was sedimented by centrifugation for 20 min at 28,000×g at 4° C., and the protein in the supernatant precipitated for 2 h by stirring with 60% (w/v) ammonium sulphate. The precipitated protein was collected by centrifugation for 20 min at 28,000×g, resuspended in Extraction Buffer, desalted by chromatography on Sephadex-G25 fine into 30 mM MOPS pH 6.9, 10% (v/v) glycerol, 10 mM 2-mercaptoethanol, 0.03% (v/v) Brij-35 and chromatographed in the latter buffer on heparin-Sepharose. The flow-through of the heparin column was titrated with 1 M NaOH to pH 7.5 and applied onto a 8 ml Source 15 Q column, which was developed in 30 mM Tris/HCl pH 7.5, 10% (v/v) glycerol, 10 mM 2-mercaptoethanol, 0.03% (v/v) Brij-35 with a 136 ml gradient to 1 M NaCl. Aliquots of all fractions were diluted 10-fold in 50 mM Tris/HCl pH 7.5, 10 mM 2-mercaptoethanol, 10 µg/ml leupeptin, 1 mM Pefabloc, incubated at 65° C. for 15 min prior to incubation for 5 min with 3 mM MnCl$_2$, 1 MBq/ml [$\gamma^{32}$P]-ATP in the absence or presence of 2 µg GST-LRRK2[1326-2527, G2019S] (purity of LRRK2 enzyme estimated at 2-5% of total protein). The reactions were terminated by addition of SDS-Sample Buffer, subjected to polyacrylamide gel electrophoresis and electrotransferred to Immobilon P. The membranes were dried and autoradiographed. All fractions and test aliquots were frozen at −80° C. Substrate containing Q-fractions 5 and 6 were diluted five times in 30 mM Tris/HCl pH 8.2, 10% (v/v) glycerol, 10 mM 2-mercaptoethanol, 0.03% (v/v) Brij-35 and applied to a 1 ml Source 15 Q column. This column was developed in 30 mM Tris/HCl pH 7.5, 10% (v/v) glycerol, 10 mM 2-mercaptoethanol, 0.03% (v/v) Brij-35 with a 10 ml gradient to 1 M NaCl and 0.5 ml fractions were collected and aliquots were screened with LRRK2 as before. Substrate containing Q-fractions 6 and 7 were applied to a 120 ml Superdex-200 column and 1.2 ml aliquots were collected and screened. Substrate containing Superdex-fractions 12-15 were pooled, concentrated and desalted by filtration in a 2 ml VivaScience system. Four microgram aliquots were denatured or left native and tested for the presence of the substrate by phosphorylation in the presence or absence of LRRK2. The samples were electrophoresed on a polyacrylamide gel, stained with colloidal blue and analysed by autoradiography. The protein band corresponding to the substrate signal was excised, digested with trypsin and subjected to protein identification by Mass-Spectrometry Fingerprinting.

Expression and purification of human moesin in E. coli. The pGEX expression constructs encoding wild type and mutant forms of human moesin were transformed into E. coli BL21 cells and 1-liter cultures were grown at 37° C. in Luria Broth containing 100 μg/ml ampicillin until the absorbance at 600 nm was 0.8. Induction of protein expression was carried out by adding 100 μM isopropyl-β-D-galactoside and the cells were cultured for a further 16 hr at 26° C. Cells were isolated by centrifugation, resuspended in 15 ml of ice-cold Lysis Buffer and lysed in one round of freeze/thawing, followed by sonication to fragment DNA. The lysates were centrifuged at 4° C. for 30 min at 26,000×g, and the recombinant proteins were affinity purified on 0.2 ml of glutathione-Sepharose and were eluted in 0.4 ml of Buffer A containing 20 mM glutathione and 0.27 M sucrose.

Mapping the sites on moesin phosphorylated by the G2019S LRRK2. Moesin (4 μg) was treated at 65° C. for 15 min and then incubated at 30° C. with 1.5 μg of GST-LRRK2 [1326-2527, G2019S] in Buffer A containing 10 mM $MgCl_2$ and 100 μM $[\gamma^{32}P]$-ATP (10000 cpm/pmol) in a total reaction volume of 50 μl. The reaction was terminated after 40 min by adding Sample Buffer to a final concentration of 1% (w/v) LDS-10 mM dithiothreitol (DTT) and the samples heated at 100° C. for 1 min and cooled on ice. 4-vinylpyridine was added to a concentration of 50 mM, and the sample was left on a shaking platform for 30 min at room temperature to alkylate cysteine residues. The samples were subjected to electrophoresis on a BisTris 4-12% polyacrylamide gel, which was stained with colloidal blue and then autoradiographed. The phosphorylated moesin band was excised, cut into smaller pieces, washed sequentially for 15 min on a vibrating platform with 1 ml of the following: water, a 1:1 mixture of water and acetonitrile, 0.1 M ammonium bicarbonate, a 1:1 mixture of 0.2 M ammonium bicarbonate and acetonitrile and finally acetonitrile. The gel pieces were dried by speedi-vac and incubated in 0.1 ml of 50 mM ammonium bicarbonate, 0.1% (w/v) n-octyl-glucoside containing 1 μg of mass spectroscopy grade trypsin (Promega). After 16 h, 0.1 ml of acetonitrile was added and the mixture incubated on a shaking platform for 10 min. The supernatant was removed and the gel pieces were further washed for 10 min in 0.3 ml of 50 mM ammonium bicarbonate, and 0.1% v/v trifluoroacetic acid. The combined supernatants, containing >90% of the $^{32}P$-radioactivity, were chromatographed on a Vydac 218TP5215 C18 column (Separations Group, Hesperia, Calif.) equilibrated in 0.1% v/v trifluoroacetic acid in water. The column was developed with a linear acetonitrile gradient (diagonal line) at a flow rate of 0.2 ml/min and fractions of 0.1 ml were collected. Phosphopeptides were further purified by Immobilised Metal-chelate Affinity Chromatography (IMAC) on Phospho-Select resin (Sigma).

Phosphopeptide sequence analysis. Isolated phosphopeptides were analysed on an Applied Biosystems 4700 Proteomics Analyser (MALDI-ToF-ToF) using 5 μg/ml alpha cyannocinnamic acid as the matrix. Spectra were acquired in both reflectron and linear modes and the sequence of phosphopeptides were confirmed by performing MALDI-MS/MS on selected masses. The characteristic loss of phosphoric acid (M-98 Da) from the parent phosphopeptide as well as the neutral loss of dehydroalanine (M-69 kDa) for phosphoserine or dehydroaminobutyric acid (–83) for phosphothreonine was used to assign the position of the phosphorylation site(s). The site of phosphorylation of all the $^{32}P$-labelled peptides was determined by solid-phase Edman degradation on an Applied Biosystems 494C sequenator of the peptide coupled to Sequelon-AA membrane (Milligen).

Assay of LRRK2 using moesin or MBP as substrates. Assays were set up in a total volume of 25 μl of Buffer A containing 0.5-0.7 μg of either wild type or mutant forms of LRRK2, 1 μM moesin (full length or indicated mutants, that had been left on ice or incubated at 65° C. for 15 min prior to assay) or 1 μM myelin basic protein, 10 mM $MgCl_2$ and 0.1 mM $[\gamma^{32}P]$-ATP (300 cpm/pmol). After incubation for 30 min at 30° C., the reactions were stopped by the addition of LDS-Sample Buffer. The incorporation of phosphate into moesin or MBP substrates as well as LRRK2 autophosphorylation was determined after electrophoresis of samples on a 4-12%-polyacrylamide gels and autoradiography of the dried Coomassie Blue-stained gels. The phosphorylated substrates were also excised from the gel and $^{32}P$-incorporation quantified by Cherenkov counting.

Assay of LRRK2 using LRRKtide as substrate. Assays were set up in a total volume of 50 μl of Buffer A containing 0.5-0.7 μg of either wild type or mutant forms LRRK2, 10 mM $MgCl_2$ and 0.1 mM $[\gamma^{32}P]$-ATP (300 cpm/pmol) in the presence of 300 μM or the indicated concentration of LRRKtide (RLGRDKYKTLRQIRQ; SEQ ID NO:1) peptide substrate. After incubation for 30 min at 30° C., reactions were terminated by applying 40 μl of the reaction mixture onto P81 phosphocellulose paper and phosphorylation of LRRKtide was quantified following washing the P81 phosphocellulose in 50 mM phosphoric acid and Cherenkov counting. One Unit (U) of LRRK2 activity was defined as the amount of enzyme that catalysed the incorporation of 1 nmol of $^{32}P$ into LRRKtide. $K_m$ and $V_{max}$ parameters were determined by performing the assay described above using varying concentration of LRRKtide. The $K_m$ and $V_{max}$ parameters were calculated using the Graph-Pad prism programme.

Immunoblotting. Samples were heated at 70° C. for 5 min in Sample Buffer, subjected to polyacrylamide gel electrophoresis and transferred to a nitrocellulose membrane. Membranes were blocked for 30 min in 50 mM Tris/HCl pH 7.5, 0.15 M NaCl, 0.2% (v/v) Tween (TBST Buffer) containing 10% (w/v) skimmed milk. The membranes were probed with 1 μg/ml of anti-GST antibody for 16 h at 4° C. in TBST Buffer containing 5% (w/v) skimmed milk. Detection was performed using horseradish peroxidase conjugated secondary antibodies and the enhanced chemiluminescence reagent.

Identification of LRRK2 autophosphorylation sites. Ten micrograms of the indicated forms of purified GST-LRRK2 [1326-2527] was incubated in a total volume of 50 μl of Buffer A containing 10 mM $MgCl_2$ and 0.1 mM ATP for 60 min. The reactions were terminated by the addition of Sample Buffer and subjected to electrophoresis on a 4-12% polyacrylamide gel, which was stained with colloidal blue coomassie. The GST-LRRK2 bands were excised from the gel and washed with 0.1 M $NH_4HCO_3$ and 50% acetonitrile/50 mM $NH_4HCO_3$. Proteins were then reduced with 10 mM DTT in 0.1 M $NH_4HCO_3$ for 45 min at 65° C. and alkylated by the addition of 50 mM iodoacetamide for 30 min at room temperature. Gel pieces were washed in 0.1 M $NH_4HCO_3$ and 50% (v/v) acetonitrile/50 mM $NH_4HCO_3$, dried, and incubated with 25 mM triethylammonium bicarbonate containing 5 μg/ml of trypsin for 16 h at 30° C. For the identification of phosphorylation sites, peptides were analysed by LC-MS on an Applied Biosystems 4000 Q-TRAP. Several databases including the Celera Discovery System (Applied Biosystems) human database were searched using the Mascot search algorithm (www.matrixscience.com).

Results

Figure 9:
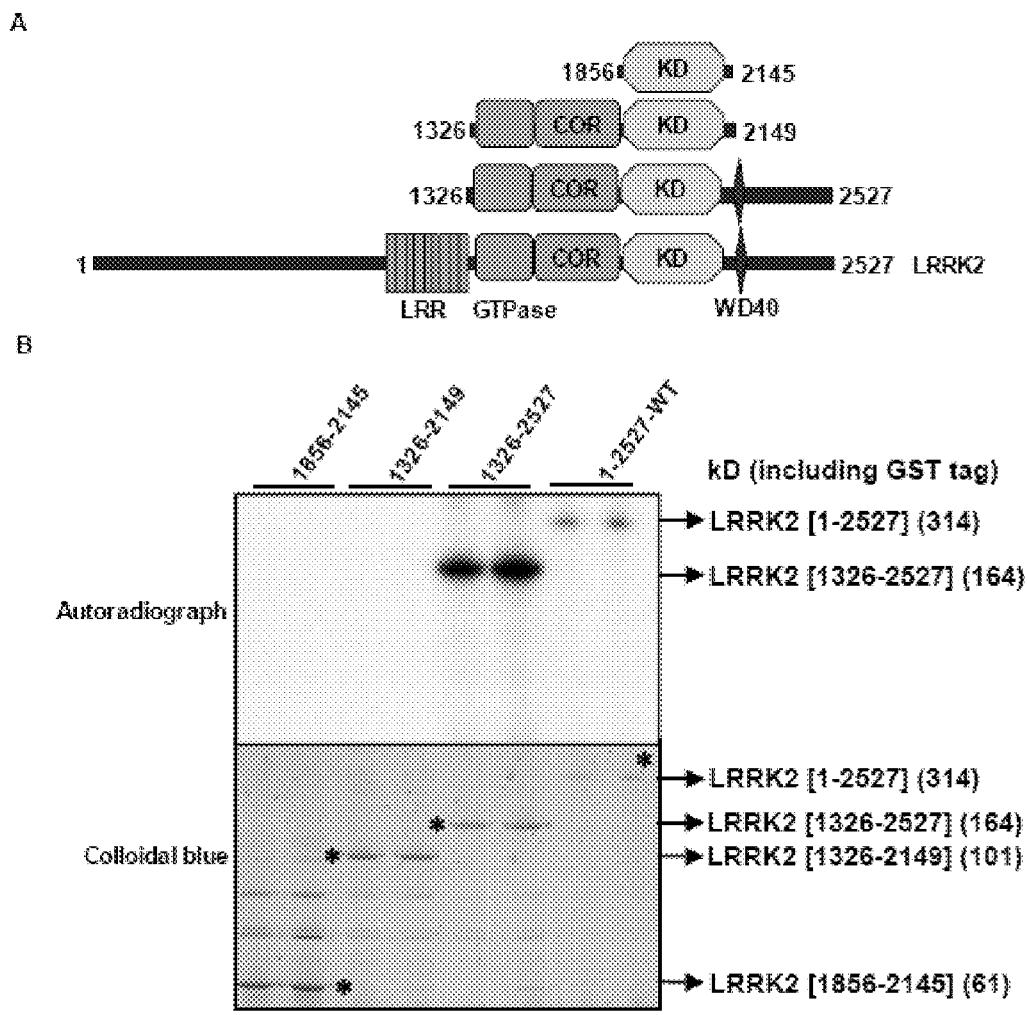
FIG. 9A-B depict the expression of forms of GST LRRK2 in 293 cells. (Upper panel) Schematic representation of the domain structure of LRRK2 showing predicted functional domains and numbering of residues corresponds to human LRRK2 residue (accession number AAV63975). Abbreviations LRR (leucine-rich repeat), COR(C-terminal Of Ras conserved motif), KD (Serine/threonine protein kinase domain). 293 cells were transfected with constructs encoding the indicated forms of GST-LRRK2. Thirty-six hours post-transfection, LRRK2 kinases were affinity purified and analysed by electrophoresis on a polyacrylamide gel and stained with colloidal blue to quantify relative protein levels. GST-LRRK2 was assayed by measuring autophosphorylation of LRRK2 following electrophoresis on a polyacrylamide gel.

Expression of an active fragment of LRRK2 for use in KESTREL. As a source of protein kinase for the KESTREL screen, GST-fusions of LRRK2 in 293 cells were expressed. Following affinity purification on glutathione-Sepharose, the expression level of full-length LRRK2 was low, but an LRRK2 fragment encompassing residues 1326-2527, lacking the Leu Rich Repeats, but still containing the GTPase, COR, kinase, WD40 and C-terminal tail was significantly higher (FIG. 9). The LRRK2[1326-2527] fragment autophosphorylated when incubated with magnesium and [γ$^{32}$P]-ATP and phosphorylated myelin basic protein (MBP), albeit weakly (FIG. 1). A catalytically inactive mutant of LRRK2[1326-2527, D2017A] in which the Mg$_2^+$-binding Asp residue was mutated, failed to autophosphorylate or phosphorylate MBP in a parallel reaction (FIG. 1). Also found was that the common PD mutant LRRK2[1326-2527 G2019S] displayed an approximate 3-fold higher level of autophosphorylation and MBP phosphorylation compared with non-mutated LRRK2 [1326-2527], consistent with previous work indicating that this mutation stimulated LRRK2 activity.

Figure 2:
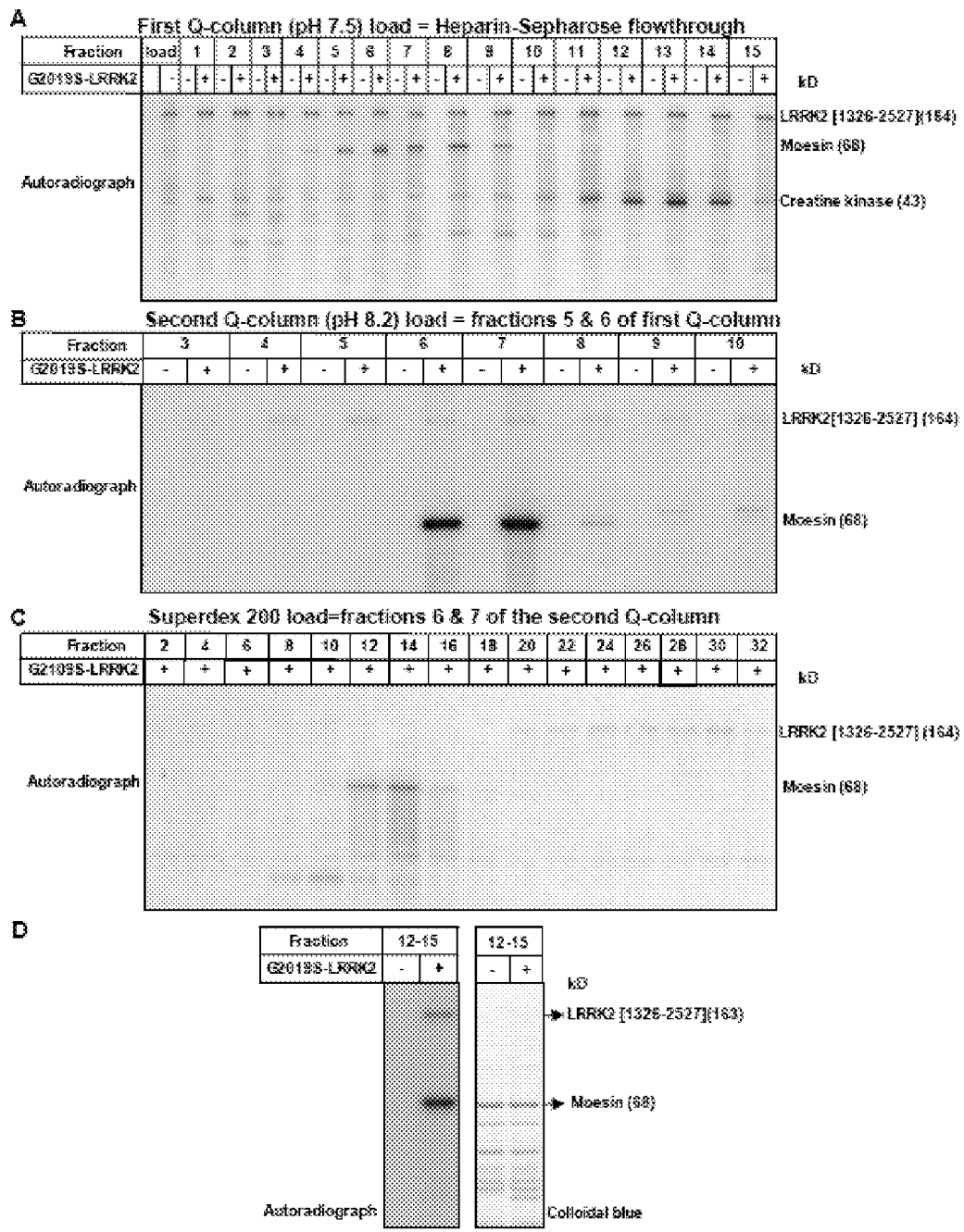
FIG. 2 depicts the LRRK2-[G2019S] KESTREL screen. (A to D) Proteins extracted from rat brain that did not bind to Heparin-Sepharose (FIG. 9), were sequentially chromatographed on the indicated columns. The specified fractions were phosphorylated in the presence (+) or absence (−) of GST-LRRK2[1326-2527, G2019S] and [$\gamma^{32}$P]-ATP. Phosphorylation of substrates was analysed following the polyacrylamide electrophoresis of the samples and autoradiography. The identity of the moesin and creatine kinase as the phosphorylated substrates is established in FIG. 3.
Figure 3:
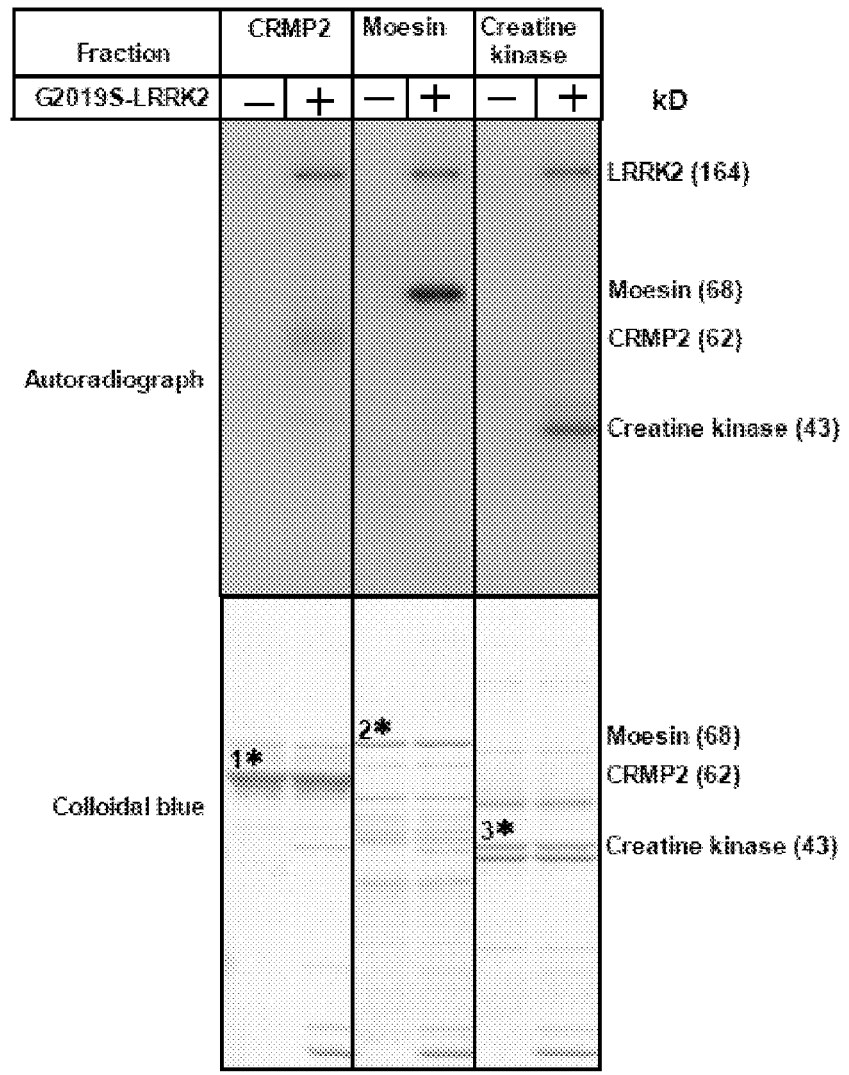
FIG. 3 depicts the identification of moesin as an LRRK2 substrate. Fractions 10-15 of a Superdex 200 column containing the 62 kDa substrate (CRMP2) that interacted with Heparin-Sepharose (FIG. 10) that was further purified in Source-Q prior to Superdex, fractions 12-15 of a Superdex 200 column containing a 68 kDa substrate (Moesin) (FIG. 2) and fraction 11 of a Q-column containing a 43 kDa substrate (creatine kinase) were concentrated using VivaScience spin filter. The samples were phosphorylated in the absence (−) or presence (+) of GST-LRRK2[1326-2527, G2019S] and [γ$^{32}$P]-ATP. Phosphorylation of substrates was analysed following the polyacrylamide electrophoresis of the samples and autoradiography. All samples were run on the same gel, but the bands shown were cut and pasted together to simplify the data. The black lines indicate where the gel was cut. The colloidal blue stained bands that were phosphorylated by LRRK2 (marked with *), were excised from the gel, digested in-gel with trypsin, and their identities were determined by tryptic peptide mass-spectral fingerprint. Mascot score is where a value >63 is considered significant (P<0.05).
Figure 10:
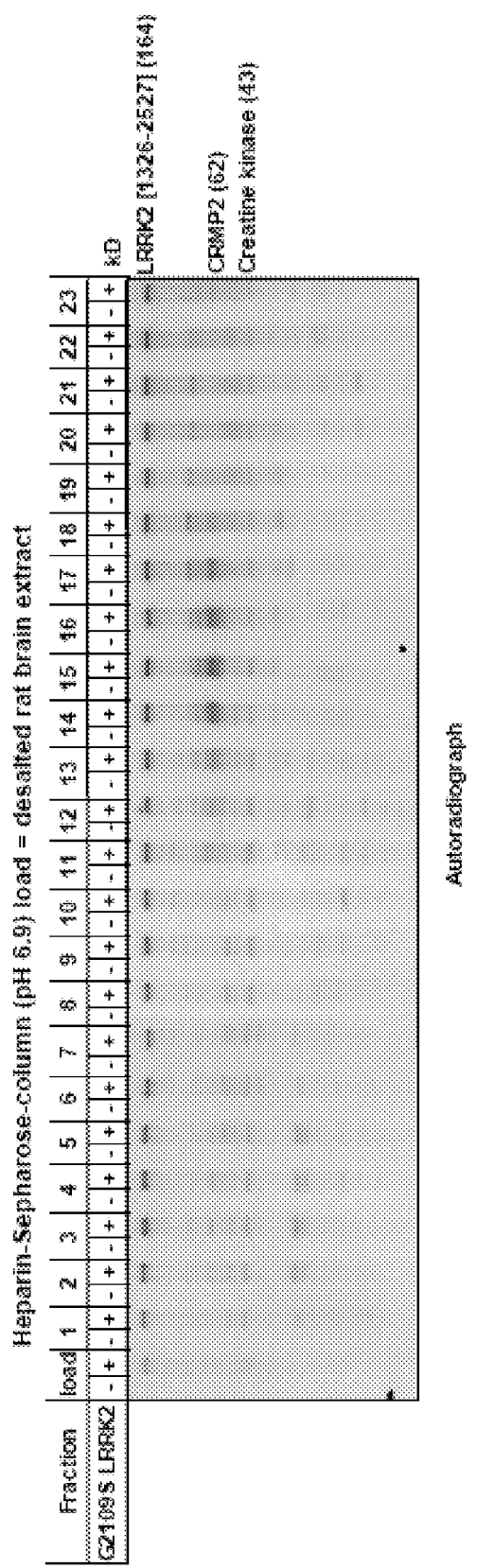
FIG. 10 depicts the LRRK2[G2019S] KESTREL screen. Proteins extracted from rat brain were precipitated with 60% ammonium sulphate, desalted and chromatographed on a Heparin-Sepharose column. Aliquots of the indicated fractions were denatured and then phosphorylated in the presence (+) or absence (−) of GST-LRRK2[1326-2527, G2019S] and Mn-[γ$^{32}$P]-ATP. Phosphorylation of substrates was analysed following the polyacrylamide electrophoresis of the samples and autoradiography. The identity of the CRMP2 and creatine kinase as the phosphorylated substrates is established in FIG. 3.

LRRK2 KESTREL screen. To search for proteins in brain that are phosphorylated by LRRK2, an extract derived from 50 rats brains was precipitated with 60% (w/v) ammonium sulphate, desalted, chromatographed on heparin-Sepharose (FIG. 10), followed by Source-Q at pH 7.5 (FIG. 2A) and Source-Q at pH 8.2 (FIG. 2B) and finally on Superdex 200 gel filtration (FIG. 2C). Aliquots of each column fraction were diluted in a reaction buffer and incubated for 15 min at 65° C. in order to inactivate endogenous protein kinases that might phosphorylate proteins and hence reduce background levels of phosphorylation that can otherwise interfere with the KESTREL analysis. Each fraction was then incubated in the presence or absence of GST-LRRK2[1326-2527] or GST-LRRK2[1326-2527, G2019S] and [γ$^{32}$P]-ATP as described in the Materials and Methods. Utilising purified non-mutated GST-LRRK2[1326-2527], no significant phosphorylation of any rat brain protein was detected (data not shown). Deploying the more active GST-LRRK2[1326-2527, G2019S] mutant, three proteins were observed to be phosphorylated (FIG. 2 and FIG. 10). These proteins were purified, subjected to electrophoresis on a polyacrylamide gel and the identity of the Coomassie blue-stained band phosphorylated by LRRK2 in each preparation was established by tryptic peptide mass-spectral fingerprinting procedures (FIG. 3). This revealed that the proteins phosphorylated by LRRK2 were collapsin response mediator protein-2 (CRMP2), creatine kinase and moesin. CRMP2 and creatine kinase were observed to be 50-100-fold more abundant in brain extracts than moesin. To examine the relative phosphorylation of these proteins by LRRK2, similar amounts of purified, CRMP2, creatine kinase and moesin proteins were phosphorylated with GST-LRRK2[1326-2527, G2019S] and under these conditions, moesin was phosphorylated to a markedly greater extent than CRMP2 or creatine kinase (FIG. 3).

Figure 4:
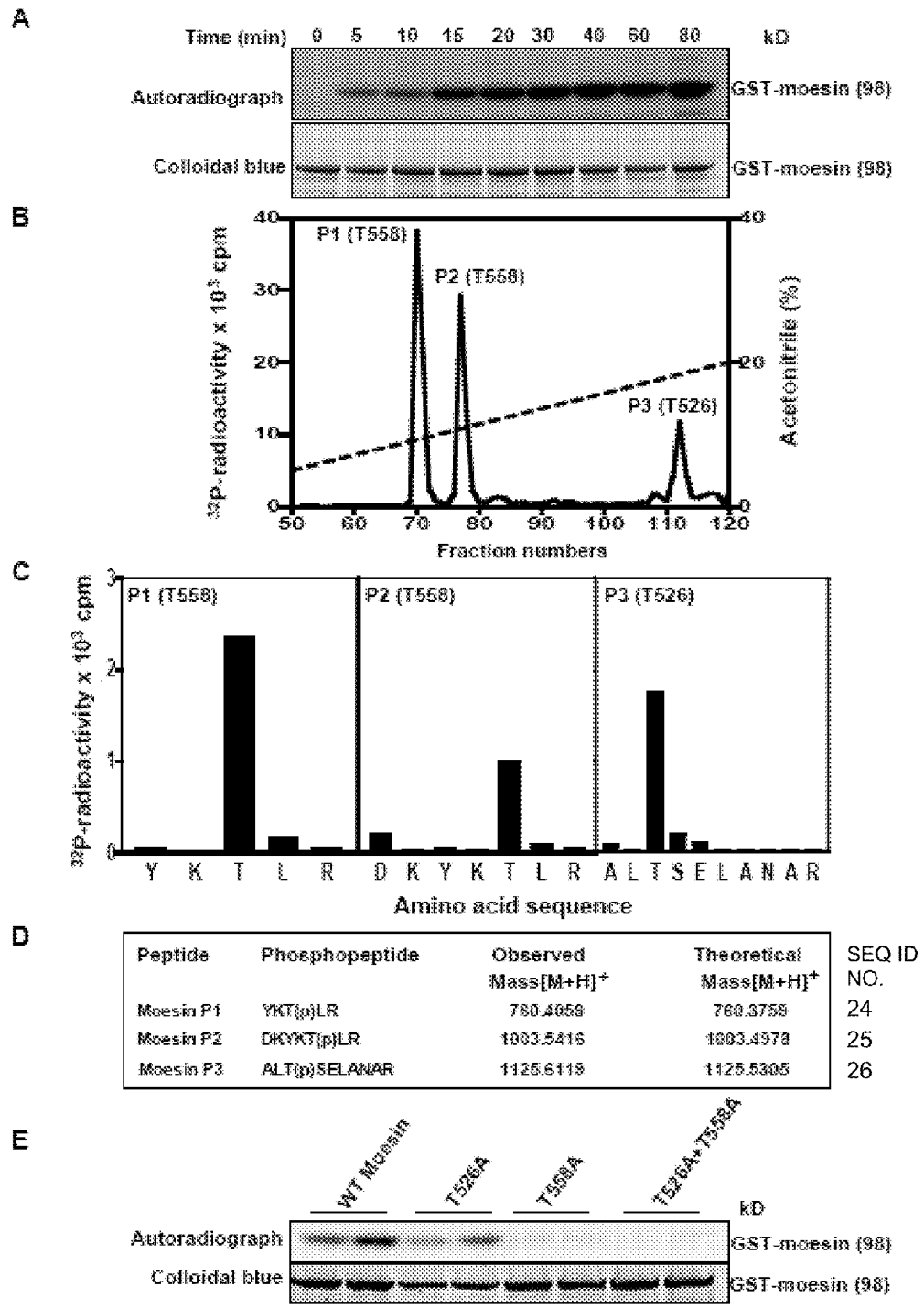
FIG. 4 depicts the identification of residues on moesin that are phosphorylated by LRRK2. (A) *E. coli* expressed moesin was incubated at 65° C. for 15 min, prior to phosphorylation with GST-LRRK2[1326-2527, G2019S] and [γ$^{32}$P]-ATP for the indicated times. Phosphorylation of the moesin protein was determined following electrophoresis on a polyacrylamide gel and subsequent autoradiography of the colloidal blue-stained bands corresponding to moesin. Similar results were obtained in three separate experiments. (B) $^{32}$P-labelled moesin after phosphorylation with the GST-LRRK2 [1326-2527, G2019S] for 40 min, was digested with trypsin and chromatographed on a C18 column. Fractions containing the major $^{32}$P-labelled tryptic peptide (P1), peptide (P2) and peptide (P3) are shown and no other major $^{32}$P-labelled peptides were observed in other fractions of the chromatography. (C) The indicated peptides were subjected to solid-phase sequencing and the $^{32}$P-radioactivity released after each cycle of Edman degradation was measured. (D) Peptides were also analysed by MALDI-ToF-ToF mass spectrometry and the inferred amino acid sequence and the site of phosphorylation denoted by (p) is indicated, together with the observed and theoretical mass of each peptide. (E) As in (A) except the indicated wild type and mutant forms of moesin were phosphorylated with GST-LRRK2[1326-2527, G2019S] for 30 min. Similar results were obtained in two separate experiments.

Mapping phosphorylated residues in moesin phosphorylated by LRRK2. Recombinant human GST-moesin expressed in E. coli that had been incubated at 65° C. for 15 min as performed in the KESTREL screen was phosphorylated by LRRK2 in a time dependent manner to a maximum stoichiometry of approximately 0.1 moles of phosphate per mole of moesin (FIG. 4A). Moesin was unable to be phosphorylated to a higher stoichiometry, indicating that a significant proportion of the recombinant enzymes may be in a conformation that cannot be phosphorylated. $^{32}$P-moesin phosphorylated with LRRK2 was digested with trypsin and chromatographed on a C18 column to isolate $^{32}$P-labelled phosphopeptides. This revealed two major peaks (P1 & P2) and one minor peak (P3) (FIG. 4B). Solid phase Edman sequencing (FIG. 4C) and mass spectrometry (FIG. 4D) of P1 and P2, established their identity as peptides phosphorylated at Thr558 and P3 as a peptide phosphorylated at Thr526. Next assessed was how mutation of Thr526 and Thr558 in moesin affected phosphorylation by GST-LRRK2[1326-2527, G2019S]. Mutation of Thr526 moderately decreased phosphorylation of moesin by LRRK2, whereas mutation of Thr558 virtually abolished moesin phosphorylation (FIG. 4E), indicating that this was the major site of phosphorylation. No phosphorylation of moesin was observed when both Thr526 and Thr558 residues were mutated.

Further analysis of the phosphorylation of moesin by LRRK2. Moesin is a member of the Ezrin/Radixin/Moesin (ERM) family of proteins that functions to anchor the actin cytoskeleton to the plasma membrane, and plays an important role in regulating membrane structure and organization. Moesin consists of a band Four-point-one/Ezrin/Radixin/Moesin (FERM) domain (residues 1 to 298) that interacts with several plasma membrane proteins, as well as phosphoinositide 4,5 bisphosphate (Ptdlns-4,5P2). The FERM domain on moesin is followed by an α-helical domain (residues 298 to 460), a flexible linker region (residues 460 to 489) and a conserved C-terminal tail (also termed C-ERMAD domain, residues 489 to 575). The last 30 amino acids of moesin encompassing Thr558, forms an F-actin binding site. Moesin and the other ERM proteins exist in at least two conformational states, namely an active "open" form capable of binding to membranes and F-actin and an inactive or dormant "closed" form, incapable of linking actin cytoskeleton to the plasma membrane, as the actin-binding site is masked. The structure of the closed state of moesin reveals that the FERM domain and C-terminal tail of moesin interact with each other, whilst in the open form the FERM and C-terminal domains are dissociated. Phosphorylation of moesin at Thr558, in conjunction to the FERM domain binding membrane proteins and perhaps to Ptdlns(4,5)P$_2$, promotes the dissociation of the C-terminal tail from the FERM domain enabling moesin to bind to F-actin. The kinases that phosphorylate moesin at Thr558 have not been firmly established, although some candidates include the Rho associated kinase (ROCK) that phosphorylates the C-terminal tail of ERM proteins in vitro and when overexpressed in cells.

Figure 5:
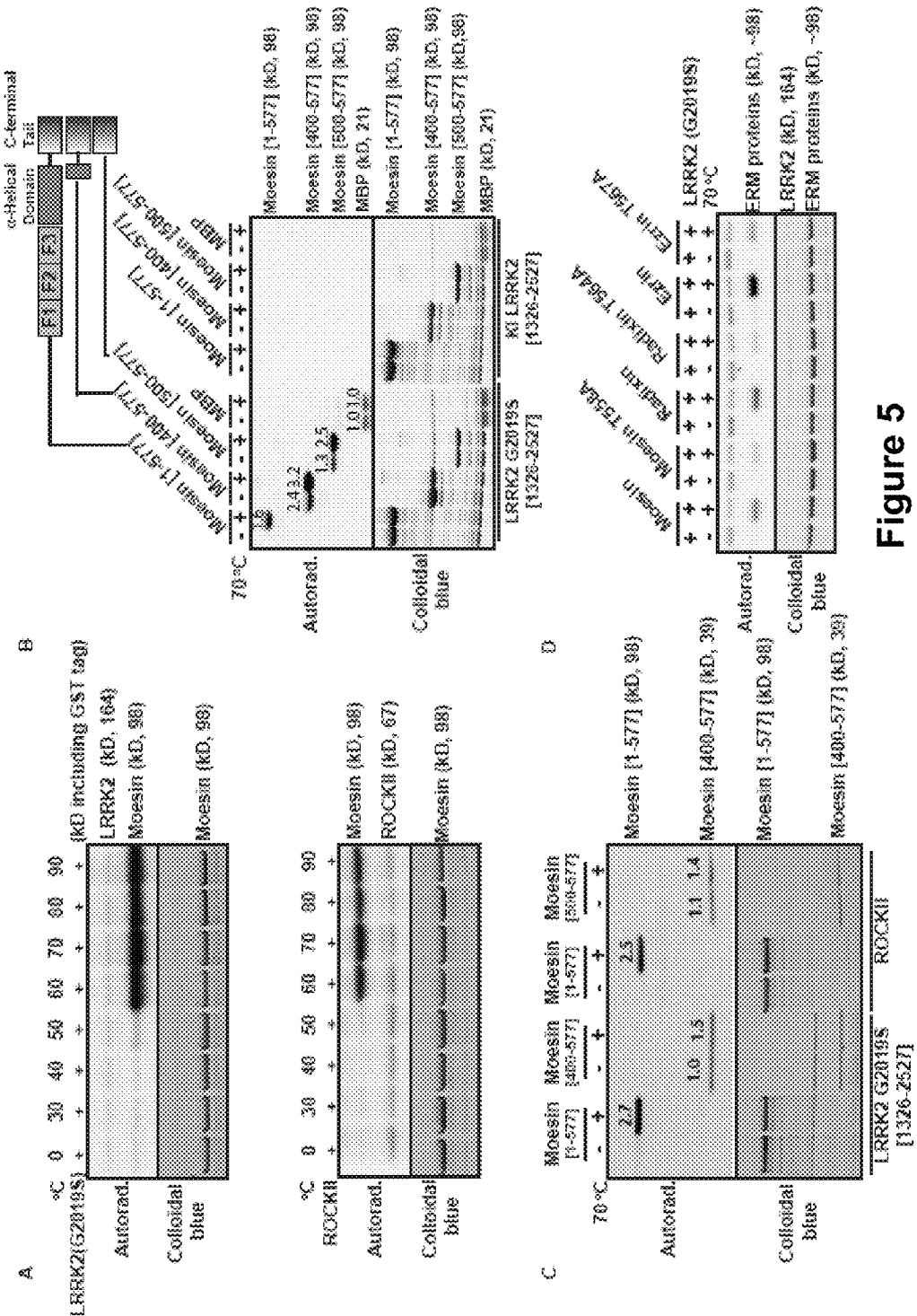
FIG. 5 depicts the analysis of phosphorylation of moesin by LRRK2 (A) *E. coli* expressed GST-moesin (1 µM) was incubated at the indicated temperatures for 15 min, prior to phosphorylation with GST-LRRK2[1326-2527, G2019S] (upper panel) or ROCK-II (lower panel) at 30° C. Phosphorylation of the moesin protein was determined following electrophoresis on a polyacrylamide gel and subsequent autoradiography of the colloidal blue-stained bands corresponding to moesin. (B & C) As in (A) except the indicated wild type and truncated forms of moesin (all at a concentration of 1 µM) were "heat denatured" by incubating at 70° C. for 15 min prior to phosphorylation with either active GST-LRRK2 [1326-2527, G2019S] or kinase-inactive (KI) GST-LRRK2 [1326-2527, D2017A] or ROCKII. Similar results were obtained in two separate experiments. Numbers above the Gel bands indicate the relative phosphorylation compared to MBP (B) or moesin[500-577] (C) not heat denatured. (D) As above, except that phosphorylation of full length wild type and indicated mutants of *E. coli* expressed GST-Ezrin and GST-Radixin by GST-LRRK2[1326-2527, G2019S] was analysed.

Previous reports found that the bacterially expressed C-terminal tail of moesin was phosphorylated by ROCK to a much greater extent than the full length moesin protein. This is presumably because when moesin is expressed in E. coli it will be in the closed conformation in which Thr558 is inaccessible for phosphorylation. In the KESTREL screen, incubating moesin at 65° C. prior to phosphorylation may have induced a conformational change that exposed Thr558. To investigate this, the effect of heating moesin expressed in E. coli affected its phosphorylation by LRRK2 (FIG. 5A) as well as ROCK-II (FIG. 5B) in parallel reactions was studied. Strikingly, neither LRRK2 nor ROCK-II were capable of phosphorylating moesin that had not been pre-incubated at temperature of at least 60° C. (FIG. 5A). In contrast, fragments of moesin lacking the FERM domain, could be phosphorylated by LRRK2 (FIG. 5C) or ROCK-II (FIG. 5D) in the absence of heat treatment prior to phosphorylation. Under the conditions employed, the moesin[400-577] C-terminal fragment was phosphorylated to approximately 2-fold greater extent than full length GST-moesin (FIG. 5B).

Identification of a peptide-based substrate assay for LRRK2. Next investigated was whether LRRK2 could phosphorylate a short peptide substrate that encompassed Thr558 of moesin (RLGRDKYKTLRQIRQ), in which the underlined Thr residue is equivalent to Thr558. GST-LRRK2 [1326-2527, G2019S] phosphorylated this peptide at approximately 3-fold higher initial rate than non-mutated GST-LRRK2[1326-2527], under conditions in which a kinase inactive GST-LRRK2[1326-2527, D2017A] failed to phosphorylate the peptide (FIG. 6A). The peptide was termed LRRKtide and was phosphorylated by both non-mutated GST-LRRK2[1326-2527] and GST-LRRK2[1326-2527, G2019S] with a similar $K_m$ of approximately 200 μM (FIG. 6B). The $V_{max}$ of phosphorylation of LRRKtide by GST-LRRK2[1326-2527, G2019S] was ~2.5-fold higher than that by non-mutated GST-LRRK2[1326-2527] (FIG. 6B). The GST-LRRK2[1326-2527, G2019S] had a $V_{max}$ of 10 U/mg and the purity of the enzyme in this preparation was estimated at approximately 5%, suggesting that a pure preparation of the LRRK2[G2019S] enzyme would phosphorylate LRRKtide with specific activity of 200 U/mg, a respectable rate for a relatively active kinase phosphorylating a favourable substrate.

Side by side assay of PD mutant forms of LRRK2. Utilising the assays elaborated supra, the activity of nine mutant forms of LRRK2 that have been reported in humans suffering from PD was compared. The mutations studied were found in the GTPase domain (R1441C, R1441G), COR region (Y1699C), kinase domain (R1914H, I2012T, G2019S, I2020T) and in a region of the C-terminal tail that lies beyond the WD40 repeat (T2356I, G2385R) (FIG. 7A). Only the commonly observed G2019S mutation significantly stimulated LRRK2 autophosphorylation as well as phosphorylation of moesin, LRRKtide and MBP (FIG. 7B). Four mutants (R1441C, R1441G, Y1699C and T2356I), possessed similar activity as non-mutated LRRK2 in all assays (FIG. 7B). Two out of the four mutations in the kinase domain (R1914H, I2012T) were nearly inactive, displaying only marginally greater activity than the kinase-inactive LRRK2[D2017A] used as a control. A third kinase domain mutant (I2020T), possessed significantly less activity than non-mutated LRRK2, but higher activity that the R1914H and I2012T mutants. Intriguingly, one of the two C-terminal tail LRRK2 mutations (G2385R), also possessed very low catalytic activity in all assays (FIG. 7B).

Defining the minimum fragment of LRRK2 that retains protein kinase activity. The activity of full length and mutant forms of LRRK2 lacking specific domains were compared. Wild type full length LRRK2 possessed similar activity towards the moesin, LRRKtide and MBP substrates, as the did the LRRK2[1326-2527] fragment utilised in the rest of this study. A mutant lacking either the GTPase domain (LRRK2[1541-2527]) or both the GTPase and COR domains (LRRK2[1856-2527]) displayed no autophosphorylation and did not phosphorylate any substrate. Moreover, LRRK2 mutants lacking either the C-terminal WD40 domain (LRRK2[1326-2149]) or just the seven C-terminal amino acids ([LRRK2[1326-2520]), were also inactive. Consistent with the notion that the GTPase, COR, WD40 and C-terminal region of LRRK2 are required for its activity, a fragment of LRRK2 encompassing only the kinase domain (LRRK2 [1856-2145]) was devoid of any kinase activity (FIG. 8).

Figure 6:
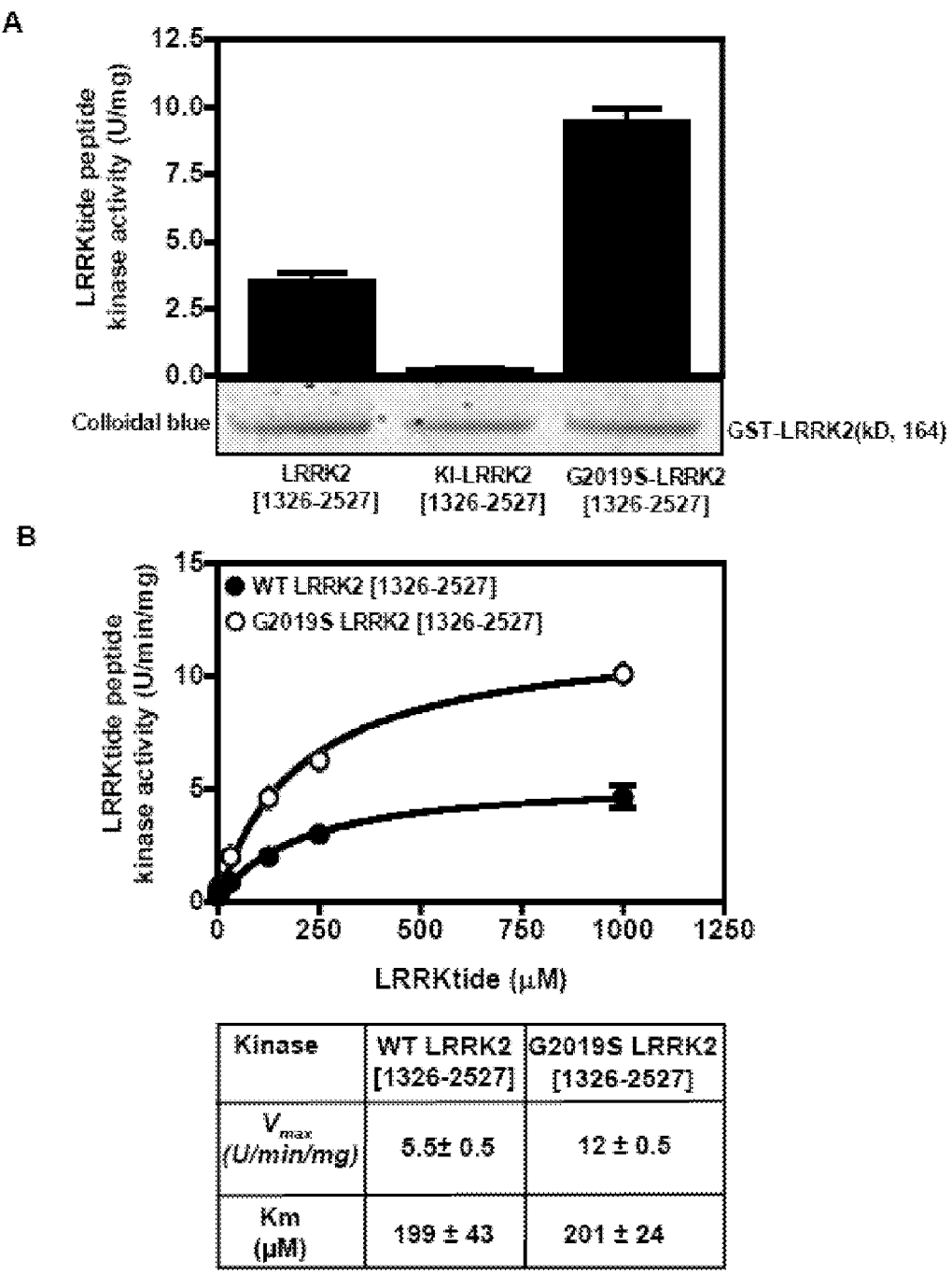
FIG. 6 depicts the generation of a peptide substrate for LRRK2. (A) 293 cells were transfected with constructs encoding the indicated forms of active and kinase-inactive (KI, D2017A) GST-LRRK2. Thirty-six hours post-transfection, LRRK2 kinases were affinity purified and analysed by electrophoresis on a polyacrylamide gel and stained with colloidal blue to quantify relative protein levels. GST-LRRK2 was assayed by measuring phosphorylation of the LRRKtide peptide (RLGRDKYKTLRQIRQ; SEQ ID NO:1) at 300 µM. Results of the kinase catalytic assays are presented as the mean catalytic activity ±S.D. of assays carried out in triplicate. The results presented are representative of 2 to 3 independent experiments. (B) As in (A) except that concentrations of LRRKtide varied to enable calculation of the $V_{max}$ and $K_m$ enzymatic parameters.
Figure 7:
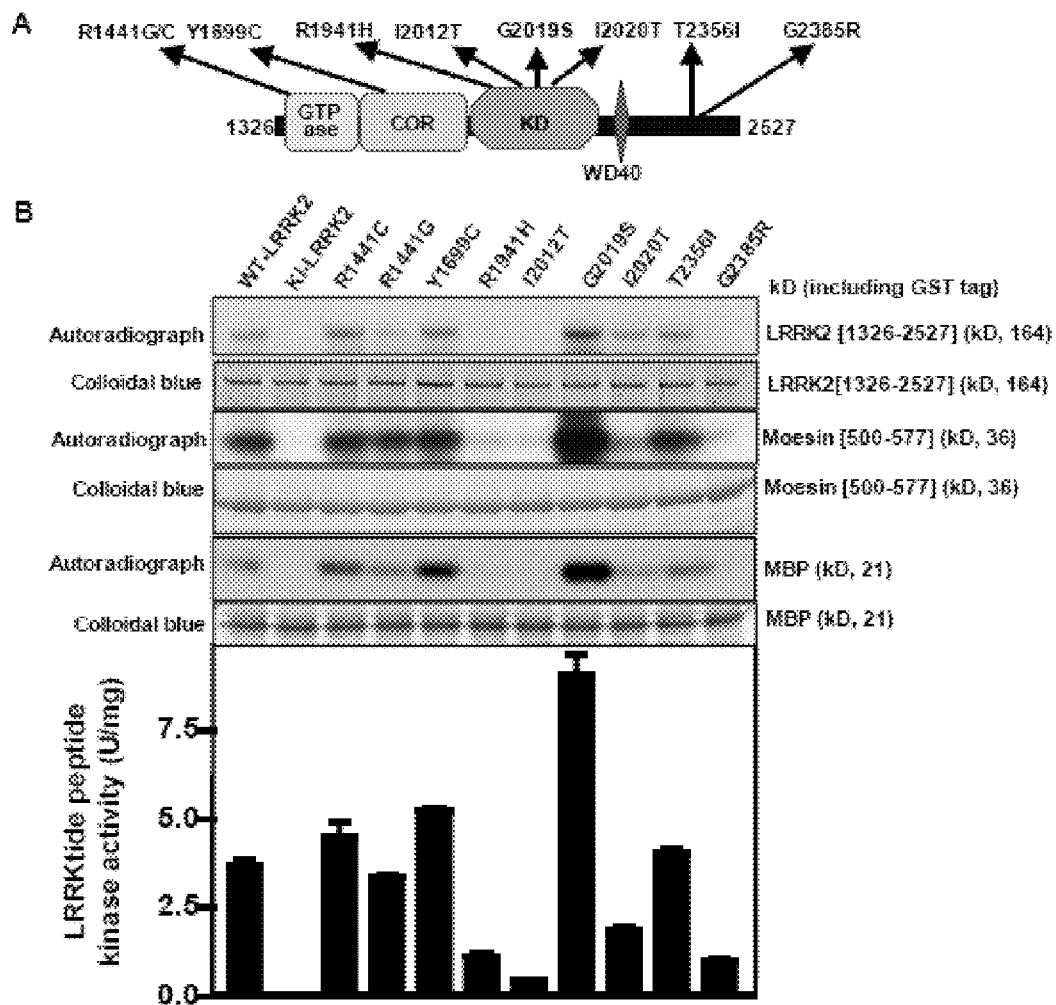
FIG. 7A-B depict the analysis of PD disease LRRK2 mutants. Schematic representation showing the location of nine PD causing mutations on LRRK2 that were analysed. (B) The non-mutated and indicated mutant forms of GST-LRRK2[1326-2527] were expressed in 293 cells and affinity purified on glutathione-Sepharose. Two micrograms of each preparation was analysed by electrophoresis on a polyacrylamide gel that was stained with colloidal blue to quantify relative protein levels. Each preparation was assayed by measuring autophosphorylation as well as phosphorylation of MBP, moesin [500-577] and LRRKtide peptide. The data for LRRKtide phosphorylation are presented as the mean specific activity (Units per mg of total protein within purified GST-LRRK2 preparation) ±S.D. of assays carried out in triplicate. The results presented are representative of 2 to 3 independent experiments.
Figure 8:
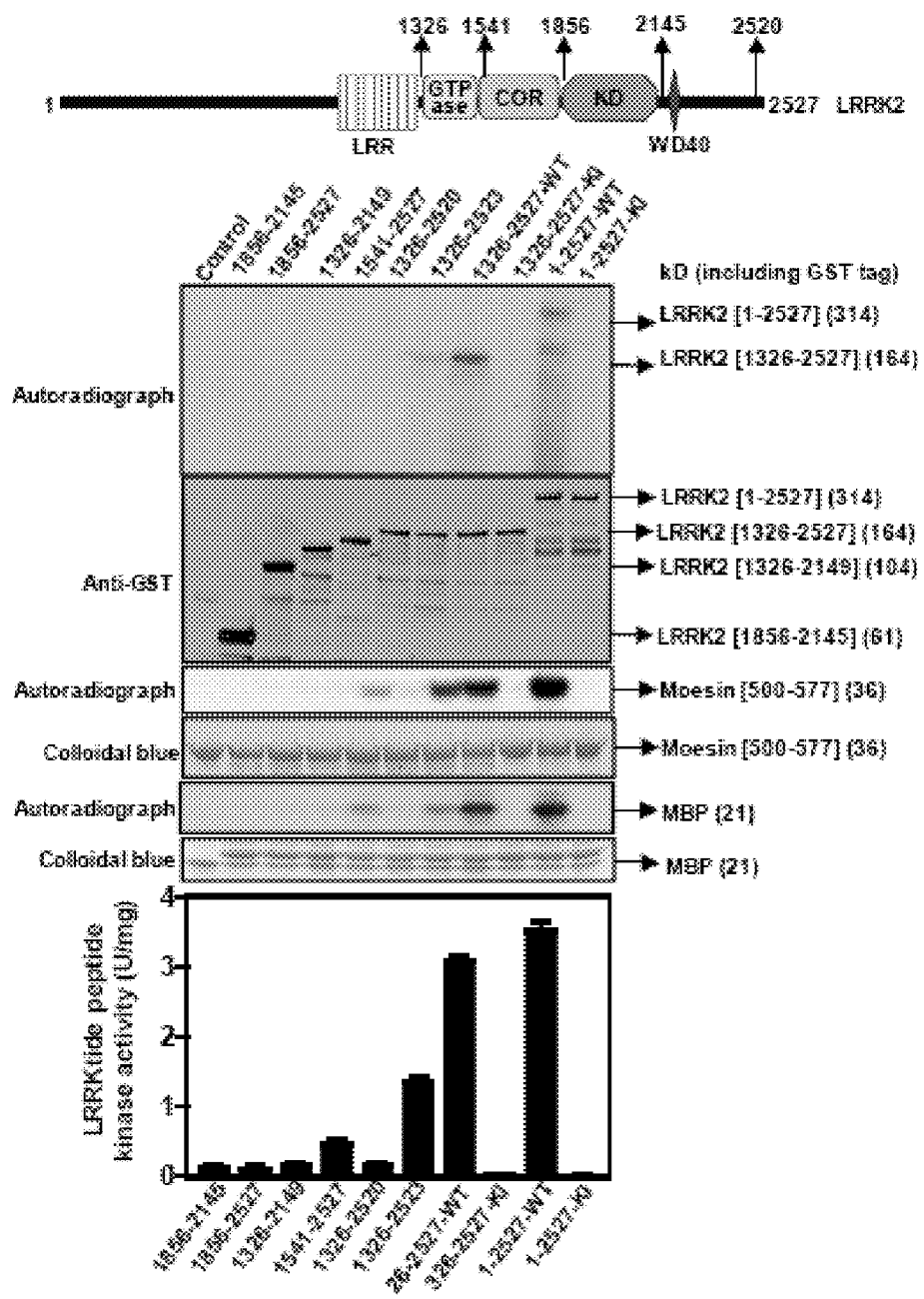
FIG. 8 depicts the role of non-kinase domains in regulating LRRK2 activity. (A) (Upper panel) Schematic representation of the domain structure of LRRK2 showing predicted functional domains and numbering of residues corresponds to human LRRK2 residue (accession number AAV63975). The wild type and indicated fragments of GST-LRRK2 were expressed in 293 cells and affinity purified on glutathione-Sepharose. One microgram of each preparation was analysed by electrophoresis on a polyacrylamide gel that analysed by electrophoresis on a polyacrylamide gel and immunoblotted with an anti-GST antibody to quantify relative protein levels. Each preparation was also assayed by measuring autophosphorylation as well as phosphorylation of MBP, moesin [500-577] and LRRKtide. The data for the LRRKtide assay are presented as the mean specific activity (Units per mg of total protein within purified GST-LRRK2 preparation) ±S.D. for assays carried out in triplicate. (B) As in (A) except that the effect of the indicated C-terminal point mutations and small C-terminal truncations of GST-LRRK2[1327-2527, G2019S] are analysed using the LRRKtide substrate. The results presented are representative of 2 to 3 independent experiments.

In the studies shown in FIGS. 6-8, the same amounts of GST-purified proteins were loaded onto each gel and the same amounts of total protein were used in each assay. All LRRK2 preparations used were similarly pure.

Figure 11:
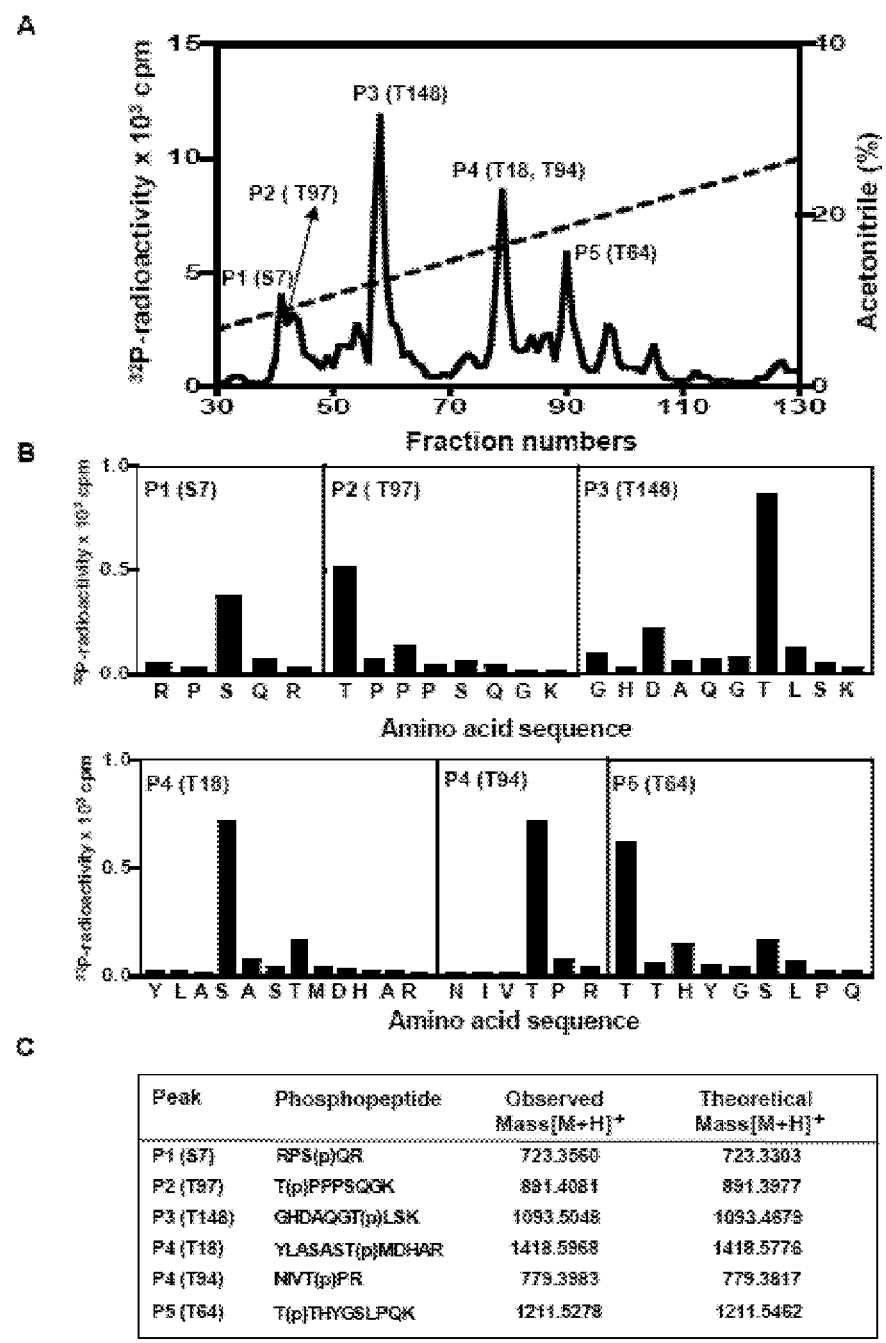
FIG. 11 depicts the analysis of the phosphorylation of MBP by LRRK2. (A) 32P-labelled MBP after phosphorylation with the GST-LRRK2 [1326-2527, G2019S] for 40 min under identical conditions used to phosphorylate moesin (FIG. 4B). This was only phosphorylated to 0.01 moles of $^{32}$P per mole of MBP. The phosphorylated MBP was digested with trypsin and chromatographed on a C18 column. Fractions containing the major $^{32}$P-labelled tryptic peptides (P1-P5) are shown. No other major $^{32}$P-labelled peptides were observed in other fractions of the chromatography. (B) The indicated peptides were subjected to solid-phase sequencing and the $^{32}$P-radioactivity released after each cycle of Edman degradation was determined. (C) Peptides were also analysed by MALDI-TOF-TOF mass spectrometry and the inferred amino acid sequence and the site of phosphorylation denoted by (p) is indicated, together with the observed and theoretical mass of each peptide.

Kinase assays in FIGS. 7 and 8 are undertaken with 1 μM MBP and 300 μM LRRKtide. Under the conditions used, about 300-1000 cpm were incorporated into MBP and typically 10-20-fold higher counts into the LRRKtide. An advantage of the LRRKtide peptide substrate is that it can be deployed at a much higher concentration than MBP and is less likely to be phosphorylated by possible contaminating protein kinases. MBP is also phosphorylated at low levels on at least 10 different sites by LRRK2 as shown in FIG. 11.

Mapping phosphorylated residues in MBP phosphorylated by LRRK2. Also studied were the residues on MBP that were phosphorylated by LRRK2. We found that MBP was phosphorylated by GST-LRRK2[1326-2527, G2019S] poorly and only to a stoichiometry of only 0.01 moles of phosphate per mole of protein. Trypsin digestion of $^{32}$P-MBP phosphorylated under these conditions revealed over 10 different $^{32}$P-labelled peptides (FIG. 11), suggesting that LRRK2 in contrast to moesin, is phosphorylating numerous sites on MBP, and all at very low stoichiometries. Using mass spectrometry and solid phase sequencing, it was possible to map six of these phosphorylation sites as Ser7, Thr18, Thr64, Thr94, Thr97, Thr148 (FIG. 11).

Figure 12:
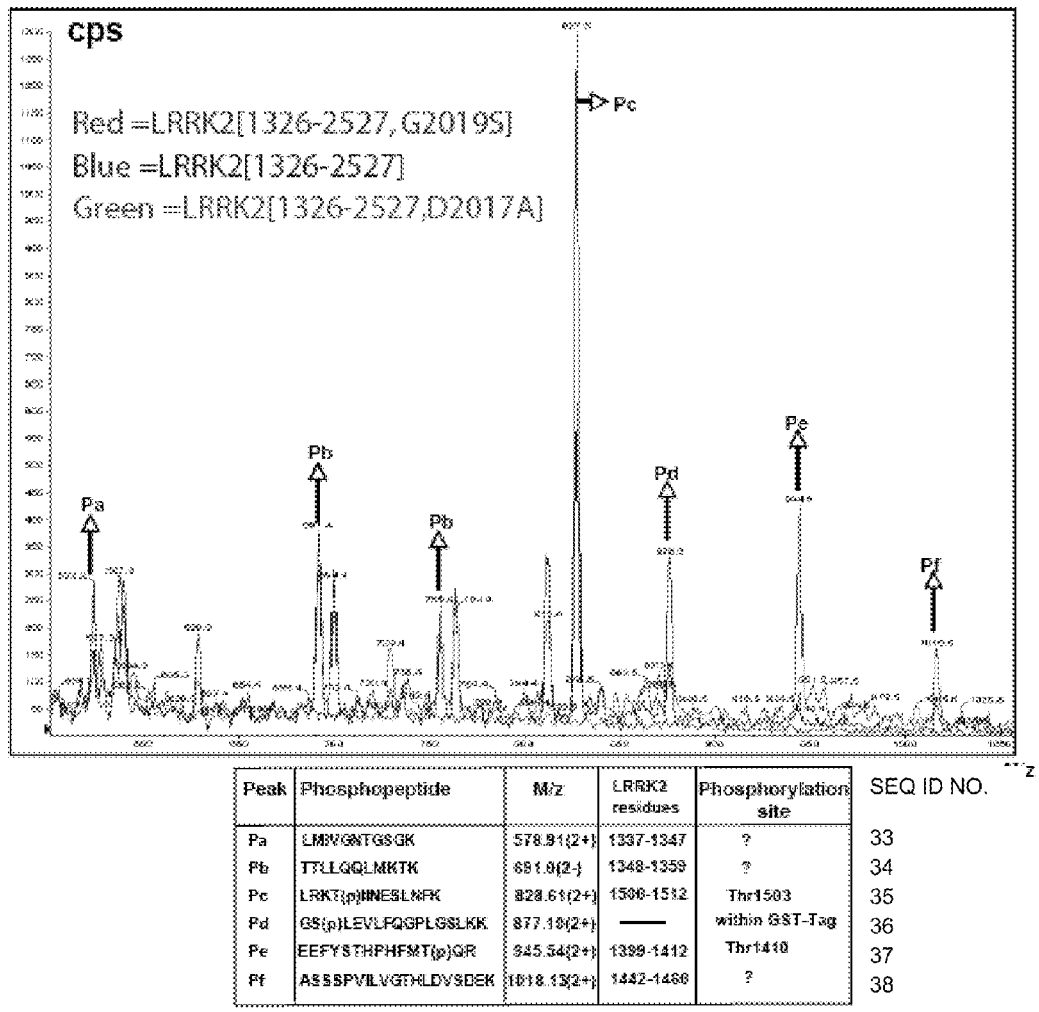
FIG. 12 depicts the analysis of the autophosphorylation sites on LRRK2. (A) The indicated forms of active and kinase-inactive (KI) forms of GST-LRRK2[1326-2527] were incubated for 40 min in the presence of 100 μM ATP. The samples were subjected to electrophoresis on a polyacrylamide and the coomassie-stained bands corresponding to GST-LRRK2[1326-2527] were excised and digested with trypsin. Phosphopeptides were identified by combined LC-MS and MS/MS analysis. The figure shows the signal intensity (cps, counts of ions detected per second) versus the ion distribution (m/z) for the phosphopeptides derived from GST-LRRK2[1326-2527] KI-GST-LRRK2[1326-2527, D2017A], GST-LRRK2[1326-2527, G2019S]. The phosphorylated peptides that we were able to identify by mass spectrometry are labelled Pa to Pf are marked. In cases where the precise site of phosphorylation within a peptide could not be determined this is indicated with a ? within the table
Figure 13:
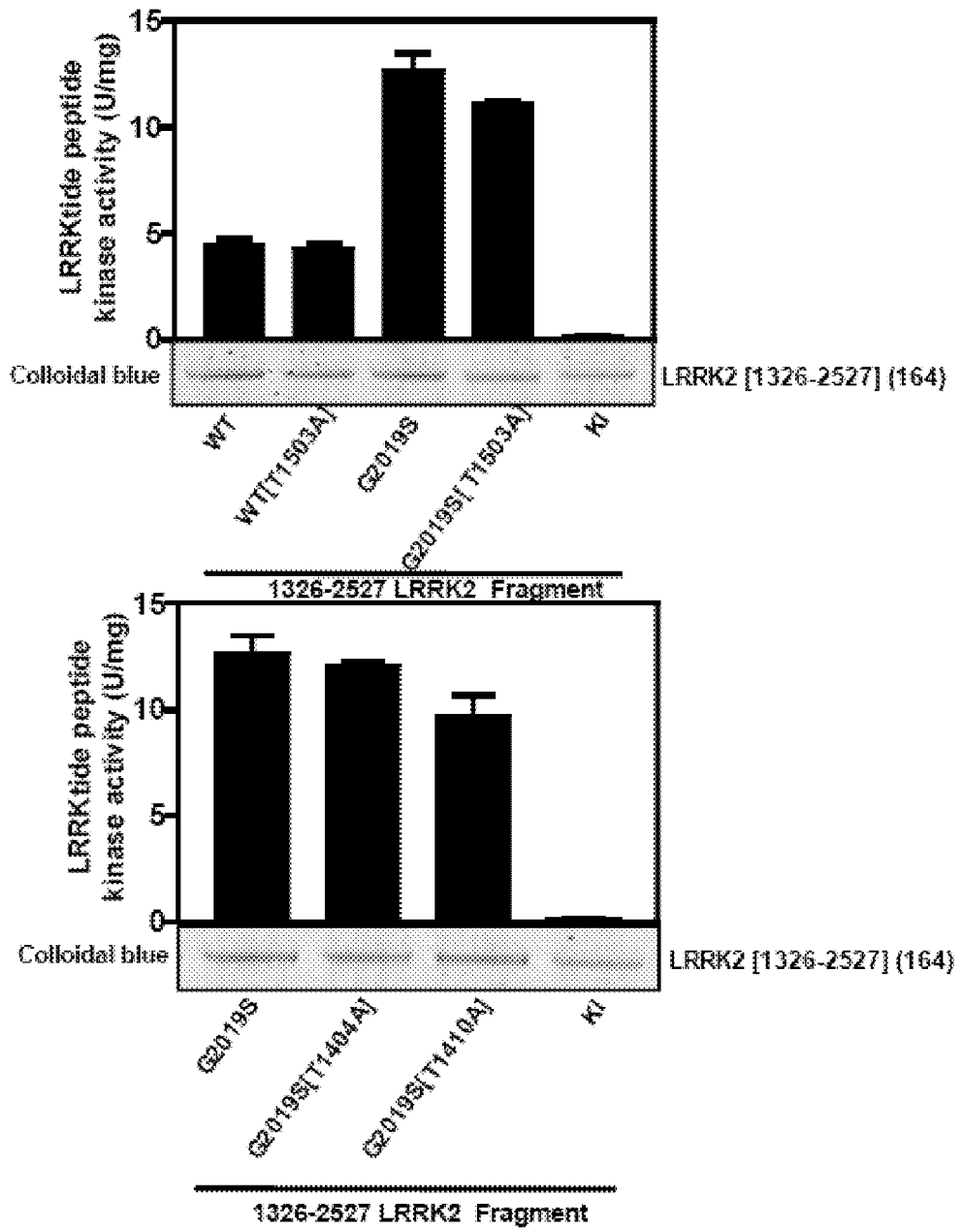
FIG. 13 depicts that the mutation of the autophosphorylation sites on LRRK2 does not affect activity. The non-mutated and indicated autophosphorylation sites mutants of GST-LRRK2[1326-2527] were expressed in 293 cells and affinity purified on glutathione-Sepharose. These were analysed by electrophoresis on a polyacrylamide gel and stained with colloidal blue to quantify relative protein levels. Each preparation was assayed by measuring activity towards the LRRK-tide peptide. The data are presented as the mean catalytic activity ±S.D. for assays carried out in triplicate.
Figure 16:
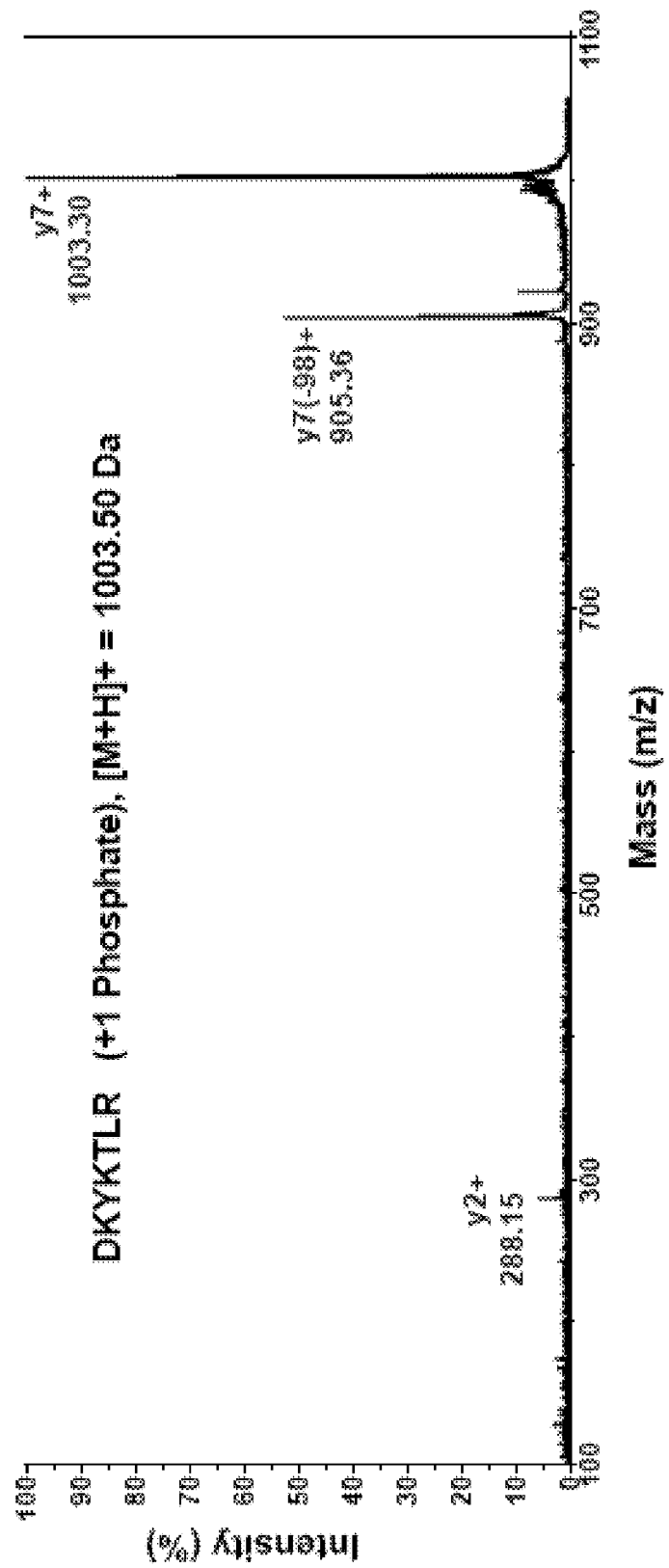
FIG. 16 depicts MALDI-ToF-ToF analysis of the major LRRK2 phosphorylated peptide on moesin. Peptide P2 derived from experiment shown in FIG. 4A was analysed on an Applied Biosystems 4700 Proteomics Analyser in reflector mode using 5 mg/ml alpha-cyano-4-hydroxy cinnamic acid in 50% Acetonitrile 0.1% Trifluoroacetic acid as the matrix. The loss of $H_3PO_4$ from this peptide is shown by the presence of the y7(-98)$^+$ ion. A similar characteristic loss of 98 Da was observed on analysis of the P1 and P3 peptides shown in FIG. 4A.

Mapping LRRK2 sites of autophosphorylation. Mass spectrometry mapping was also done of the autophosphorylation sites on GST-LRRK2[1326-2527], GST-LRRK2[1326-2527, G2019S] as well as catalytically inactive GST-LRRK2[1326-2527, D2017A] that were observed following incubation of these enzymes with Mg-ATP. No phospho-peptides were observed on the catalytically-inactive LRRK2, but the non-mutant and G2019S forms of LRRK2 autophosphorylated at numerous sites (FIG. 12). By mass spectrometry analysis, 5 phosphorylated peptides were identified that were all located within the GTPase domain (between residues 1335-1504, FIG. 12). The major autophosphorylation site was on non-mutated GST-LRRK2[1326-2527] was Thr1503. This residue was phosphorylated at a 2-3-fold higher level on GST-LRRK2[1326-2527, G2019S]. Others including Thr1410 were phosphorylated to a higher stoichiometry on the more active GST-LRRK2[1326-2527, G2019S] mutant (FIG. 12). Mutations at Thr1410 and Thr1503 to Ala did not affect LRRK2 catalytic activity (FIG. 13).

The most active mutant G2019S form of LRRK2 encompassing residues 1326-2527 was employed for a kinase substrate screen in brain and identified moesin as the best-known protein substrate for this enzyme. A peptide encompassing the phosphorylation site Thr558, was also a useful in vitro substrate. Using this methodology the requirements for catalytic kinase activity of LRRK2 was analyzed by comparing a set of point mutants and deletions and to establish how mutations of LRRK2 found in PD patients impacted on enzyme activity. As the sequences surrounding the Thr558 site on moesin are identical in ezrin and radixin, it is likely that LRRK2 will also be capable of phosphorylating these proteins.

Mmoesin and radixin have been implicated in playing a key role in regulating neurite outgrowth, as neurones that are deficient in these proteins display a marked reduction of growth cone size, disappearance of radial striations, retraction of the growth cone, and a marked disorganization of actin filaments that invade the central region of growth cones. Recent studies also demonstrate that overexpression of the activated G2019S LRRK2 mutant induces a progressive reduction in neurite length and branching both in primary neuronal cell culture and in the rat nigrostriatal pathway, whereas LRRK2 deficiency leads to increased neurite length and branching. Taken together these data suggest that deregulation of moesin phosphorylation by mutant LRRK2 might contribute to the early loss of dopaminergic axon terminals in Parkinson's disease. In humans inactivating mutations in a gene encoding a protein related to moesin, termed merlin, cause neurofibromatosis type 2, a form of cancer affecting predominantly the nervous system.

The most common G2019S LRRK2 PD mutation enhances kinase activity, a conclusion that is consistent with two recent studies in which LRRK2 activity was assessed by autophosphorylation and phosphorylation of MBP. Kinetic analysis with LRRKtide also indicates that the G2019S mutation stimulates LRRK2 activity by increasing the catalytic $V_{max}$ constant rather than enhancing substrate-binding $K_m$ affinity. Analysis of the 518 human kinases indicates that two protein kinases (TSSK1, BUBR1), as well as seven predicted inactive pseudokinases (KSR2, STLK6, RSKL1, SgK071, Domain2_GCN2, SgK269, SgK196), have a Gly to Ser substitution motifs at subdomain VII of their catalytic domain.

Not all PD mutations stimulate the activity of LRRK2. Four PD mutations R1441C, R1441G (located in GTPase domain), Y1699C (located in COR domain) and T2356I (located in C-terminal tail) did not significantly influence LRRK2 kinase activity. Moreover, three mutations R1941H, I2012T (located in kinase domain) and G2385R (located in the C-terminal tail) markedly inhibited LRRK2 kinase activity. Another PD mutation I2020T (in the residue located next to the Gly2019) reduced LRRK2 autophosphorylation and phosphorylation of MBP and moesin, but to a lower extent than the R1941H, I2012T and G2385R mutations. A recent report indicated that the Y1699C mutation possessed approximately 50% increased autophosphorylation compared to the wild type protein. Although this mutant possesses marginally greater activity than the wild type protein (FIG. 7), it is significantly less active than the G2019S mutant. Another report judged the ability of the I2020T LRRK2 mutant to autophosphorylate to a approximately 40% higher level than wild type LRRK2, which contrasts to the present disclosure that this mutant possess lower activity.

These results in assessing PD mutant forms of LRRK2, indicate that not all mutations exert their effects in the same manner as the G2019S mutation, which increases protein kinase activity. It is possible that some of the mutations exert their effects by interfering with the cellular interaction of LRRK2 with regulatory binding partners and/or alter LRRK2 cellular stability or localisation. The finding that some mutations reduce kinase activity, indicate that inhibition of LRRK2 might also have the potential to lead to degeneration of dopaminergic neurones and development of PD. If this was the case, it would suggest that the therapeutic efficacy of LRRK2 inhibitors might be limited to treatment of patients with activating G2019S LRRK2 mutations and that doses of such drugs would need to be utilised that do not reduce the activity of the disease causing LRRK2[G2019S] enzyme below basal levels.

Also demonstrated is that an intact C-terminal tail of LRRK2 is required for activity, as truncation of only the seven C-terminal residues of this region ablated LRRK2 activity. The G2385R PD mutation located C-terminal to the WD40 motif inactivated LRRK2 kinase activity. This mutation, especially prevalent in ethnic Chinese Taiwanese populations, may represent a polymorphism that increases the risk of developing PD rather than a PD causative mutation. The C-terminal region of LRRK2, apart from the WD40 motif, possesses no homology to any other known protein or other functional domain. Taken together these observations indicate that the entire C-terminal region of LRRK2 plays an important role in regulating kinase activity.

The results disclosed herein define the minimum fragment of LRRK2 that retains protein kinase activity and also demonstrate that in vitro, LRRK2 efficiently phosphorylates moesin at Thr558.

Example 2

Ezrin and Radixin are Phosphorylated by LRRK2 at the Residue Equivalent to Thr558 of Moesin The amino acid sequence surrounding the Thr558 site of phosphorylation in moesin is identical in ezrin and radixin, suggesting that these proteins will also be phosphorylated by LRRK2. To investigate this, it was determined whether LRRK2 would phosphorylate full-length ezrin and radixin that had been expressed in *E. coli*. Similarly to full-length moesin, ezrin and radixin were only phosphorylated by LRRK2[1326-2527, G2019S] after they were heated at 70° C. (FIG. 5D and FIG. 15). Mutation of the residue equivalent to Thr558 in ezrin (Thr567) and radixin (Thr564) to Ala, strongly reduced phosphorylation of these proteins by LRRK2 indicating that these are major phosphorylation sites. Under the conditions used, GST-ezrin was phosphorylated at approximately 2-fold greater extent by LRRK2[1326-2527, G2019S] than GST-moesin and GST-radixin, suggesting that this might represent the best in vitro substrate to assess LRRK2 enzymic activity.

Example 3

Assay Formats Suitable for Compound Screening

Protein kinase screening assay formats known in the art may be used, adapted in view of the identification of ESM family polypeptides as substrates of LRRK2 polypeptides.

For example, the techniques used in Example 1 may be used in screening compounds. Assays similar to those described in WO 03/087400 (incorporated by reference herein) may be used. Screening assays which are capable of high throughput operation may be used. For example, assays using a substrate peptide based on one of the ERM family polypeptide phosphorylation sites, for example using an antibody binding to the phosphorylated form of the peptide but not the unphosphorylated for (or vice versa) may be suitable.

Cell based assays may be used, for example when assessing the effect of compounds on cell volume responses.

Protein-protein binding assays may be used, for example using surface plasmon resonance-based techniques or chip-based binding assays, as well known to those skilled in the art.

SPA-based (Scintillation Proximity Assay; Amersham International) assays may be used as well known to those skilled in the art. For example, beads comprising scintillant and a substrate polypeptide, for example a moesin peptide substrate as discussed above may be prepared. The beads may be mixed with a sample comprising $^{32}$P- or $^{33}$P-γ-labelled ATP, a LRRK2 polypeptide and with the test compound. Conveniently this is done in a 96-well format. The plate is then counted using a suitable scintillation counter, using known parameters for $^{32}$P or $^{33}$P SPA assays. Only $^{32}$P or $^{33}$P that is in proximity to the scintillant, i.e. only that bound to the substrate that is bound to the beads, is detected. Variants of such an assay, for example in which the substrate polypeptide is immobilised on the scintillant beads via binding to an antibody or antibody fragment, may also be used.

A non-radioactive assay, suitable for screening of small drug-like compound libraries, in an ELISA format can be used.

Anti-phospho-moesin558 and anti-phospho-moesin526 anti-phospho-peptide antibodies can be raised in sheep, for example for use in western blotting. They are evaluated for use in the ELISA format. Immobilization of moesin or a moesin fragment to a microtitre plate, eg by absorption or capture via GST-tag, is not expected to affect the ability of the LRRK2 polypeptide to phosphorylate it.

The assay can be performed in maxisorp (Nunc) 384-clear plates. The moesin fragment, 30 ng/well, is coated overnight at 4° C. in Tris buffered saline (TBS) pH 7.4. Excess binding sites are blocked with 5% BSA in TBS containing 0.2% Tween (TBST) for 1 hour at room temperature and then washed three times with TBST. Fifteen microliters of LRRK2 (1-1000 ng) in reaction buffer (50 mM Tris pH 7.5, 0.01%

BSA, 0.1 mM EGTA, 1 mM DTT) is added to the well and 2 µl of compound dissolved in 11% DMSO was added and incubated for 30 minutes. The reaction is initiated by the addition of 5 µL ATP (1-1000 µM)/10 mM MgCl$_2$ and incubated at room temperature for 25 minutes. The reaction is stopped by addition of 20 µL 0.5 M EDTA. The plates were washed three times with TBST before the addition of 22 µL anti-phospho-moesin558 antibody (diluted 1:3700 fold in TBST containing 20 µg/ml blocking peptide). After 1 hour the plates are washed three times with TBST and then 22 µL of anti-sheep-peroxidase conjugate (1:5000 dilution in 1% BSA/TBST) is added to each well and incubated a further 1 hour. A final four washes of TBST are performed before addition of 22 µl peroxidase substrate 3,3',5,5'tetramethylbenzidine TMB in 50 mM acetic acid, 50 mM sodium Acetate, 0.0009% H$_2$O$_2$. Colour is developed for 15 minutes and stopped by addition of 5 µL 1M HCl. Plates are read on an absorbance reader at 450 nm.

Alternative commercially available peroxidase substrates could be used, which would allow different colour detection. For example orthophenylenediamine (OPD) which is read at 492 nm or Diammonium-2,2'-azino-bis(3-ethyl-benzothiazoline-6-sulfonate) which is read at 405 nm. Alternative detection technologies can also be applied using fluorescent substrates such as 10-acetyl-3.7, dihydroxyphenoxazine or luminal based sustrates for luminescence.

The assay is considered to be tolerant to a wide range of ATP concentrations (1-1000 µM) and 1% DMSO (compound storage solvent). Compound interference by autofluorescence, quenching or absorbance is considered to be minimised as it is heterogeneous involving several wash steps.

Example 4

Evaluation of Moesin, Radixin, Ezrin and Merlin as Substrates for LRRK2

Figure 18:
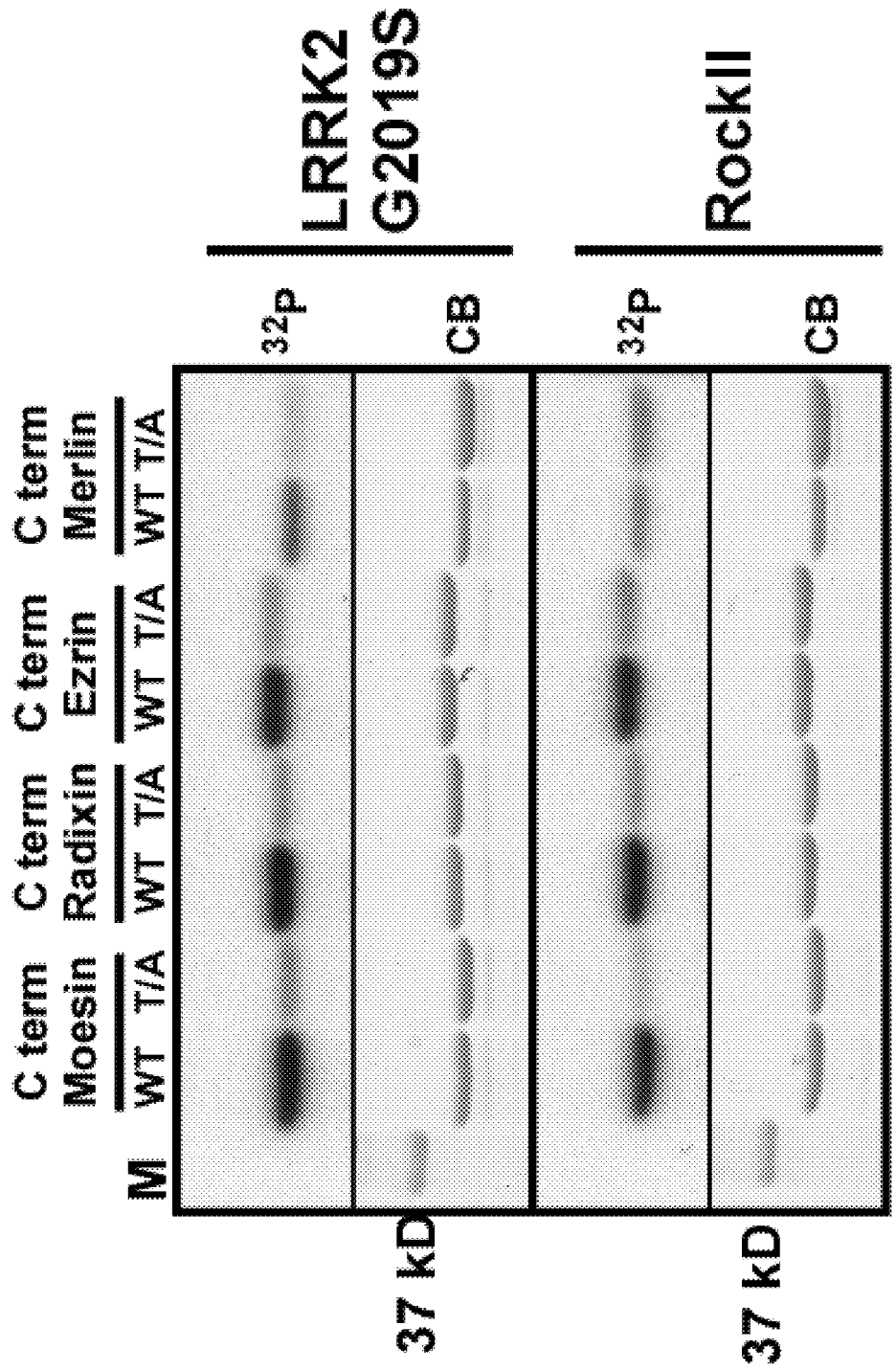
FIG. 18 depicts evaluation of moesin, radixin, ezrin and merlin as substrates for LRRK2. Reaction products were evaluated by SDS-PAGE and coomassie blue staining (CB) followed by autoradiography ($^{32}$P).

The carboxy termini of the ERM proteins, along with merlin, were produced as GST fusions in bacteria. The fragments and mutations generated were as follows: moesin amino acids 500-end, wild-type and T558A; ezrin amino acids 505-end, wild-type and T567A; radixin amino acids 503-end, wild-type and T664A; and merlin 514-end wild-type and T567A. The ability of LRRK2 and Rock to modify these proteins was determined by in vitro kinase reactions in the presence of [γ-$^{32}$P] ATP (FIG. 18). Recombinant GST-LRRK2 1326-end was prepared as described (Jaleel et al. 2007). Rock is a constitutively active fragment, amino acids 2-543, purified from insect cells. Reaction products were evaluated by SDS-PAGE and coomassie blue staining (CB) followed by autoradiography ($^{32}$P). LRRK2 readily modifies the analogous T558 sites on all ERM proteins and notably merlin, indicating that it is a novel in vitro substrate for LRRK2. Rock also modifies the ERM proteins on the T558 site and the analogous ERM residues, however it does not phosphorylate merlin on T567, indicating that it exhibits differing substrate determinants from LRRK2.

FIG. 19 depicts elucidation of LRRK2 phosphorylation site determinants in recombinant protein. FIG. 19A depicts in the left panels, moesin 500-end T526A subjected to site directed mutagenesis where the amino acids from the −8 to +8 position of the phosphorylation site were changed to Ala. In the right panels, moesin 500-end T526A was subjected to site directed mutagenesis where the indicated residues of moesin were replaced with the indicated residues. These proteins were subjected to in vitro kinase reactions with LRRK2 and Rock and reaction products were evaluated by SDS-PAGE and coomassie blue staining (CB) followed by autoradiography ($^{32}$P). FIG. 19B depicts the sequence of the residues surrounding the moesing T558 phosphorylation site is shown with numbering and residue position indicated.

FIG. 20 depicts elucidation of LRRK2 phosphorylation site determinants in peptides. To further study the amino acid determinants that direct LRRK2 recognition of LRRKtide compared to Rock, individual peptides were synthesized where the residues −6 to +5 of LRRKtide were substituted with Ala, 3A and C. Additionally, peptides were synthesized where the residues were also altered to the indicated residues FIGS. 19B and D. A longer LRRKtide (Long), with the +7 to +12 residues of the Thr 558 site was compared to the LRRKtide. Concentration dependent phosphorylation of peptides was monitored for both LRRK2 (A and B) and Rock (C and D).

−6 Position

Substitution of Gly 552 to Ala had moderate effects on the recognition of recombinant protein substrate by LRRK2 and Rock. This was similar for LRRK2 modification of the peptide with the 552A alteration, however the negative effect was more evident for Rock as there larger decrease in reaction rate.

−5 Position

The substitution of Arg 553 to Ala decreased the modification of recombinant protein as well as peptide for both LRRK2 and Rock.

−4 Position

Recombinant protein data indicate that an acidic residue at the −4 position is disfavored by LRRK2 and Rock, demonstrated by an increase in signal when this residue is changed to Ala. For LRRK2, the positive effect of removing the negative charge at this position less pronounced when assayed by peptide phosphorylation; but, is clearly evident for Rock shown by the increase in reaction rate for the peptide.

−3 Position

Recombinant protein data indicate that a basic residue (K555) is less favored at the −3 position for LRRK2, demonstrated by an increase in signal when this residue is changed to Ala. However, for Rock, a basic residue at this position seems preferred, as a mutation to Ala or Glu acid blocks phosphorylation. A Pro residue is very well tolerated at this position for both LRRK2 and Rock. Enhanced modification of the K555A peptide is not seen with LRRK2 and the Rock preference for a basic residue at 555 is evident by the decrease in reaction rate.

−2 Position

Substitution of Tyr556 to Ala decreases LRRK2 phosphorylation of the recombinant protein to near background levels and markedly decreases the phosphorylation by Rock. Additionally, Tyr556 to Pro, Glu or Arg also has deleterious effects of LRRK2 recognition of the substrate. All of these observations are recapitulated when the substitutions are evaluated in the context of the LRRKtide. Interestingly for Rock, the Tyr556Pro mutant is weakly modified by Rock and the negative charge of the Tyr556Glu substitution completely blocks phosphorylation by Rock. These results are also recapitulated with peptide phosphorylation. A basic charge at the −2 position, Tyr556Arg, results in a massive increase in phosphorylation by Rock. Although the 556R peptide is phosphorylated similar to wild-type levels. These results indicate that a hydrophobic residue at the −2 position is necessary for LRRK2 and that a basic charge is most preferred by Rock.

−1 Position

Substitution of Lys557 to Ala resulted in a decrease in modification by LRRK2. and a complete block of phosphorylation by Rock. This effect was more pronounced when Lys557 was altered in the peptide and the reaction rate values are less than half of that for wild-type.

+1 Position

In recombinant protein, substitution of Leu559 to Ala, Phe, Gly, Lys, Pro, or Tyr has little to no effect on the phosphorylation by LRRK2, but alteration of Leu559 to Glu is deleterious. When Leu559Ala is assayed in the context of LRRKtide, there is a decrease in the reaction rate to approximately half that of wild-type. However, the Leu at the +1 position appears to be crucial for substrate recognition by Rock, as any mutation assayed in recombinant protein or LRRKtide at this position blocks phosphorylation.

+2 Position

For both LRRK2 and Rock, a basic residue is preferred at this position. Substitution of Arg560 to Ala, Pro or Glu blocks phosphorylation by both kinases. When the Arg560 to Ala, Pro or Glu is assayed in the context of LRRKtide, LRRK2 is unable to phosphorylate the peptide. For Rock, substitution of Arg560 to Ala or Pro decreases the reaction rate but not completely, with the Pro substitution showing a slightly lower affinity.

+3 Position

Alteration of Gln561 to Ala exhibited a negligible effect on the ability of LRRK2 or Rock to modify the recombinant substrate. For LRRK2 this effect was also minimal when assayed by peptide phosphorylation, with only a slight decrease in reaction rate. However for Rock, there was a marked shift in reaction rate seen when Gln561 was substituted with Ala in the LRRKtide.

+4 Position

Substitution of Ile562 to Ala decreased LRRK2 phosphorylation of both the recombinant substrate as well as the peptide substrate. This substitution increased Rock modification of the recombinant substrate but slightly decreased the phosphorylation of the peptide substrate.

+5 Position

Altering Arg563 to Ala, Pro or Glu has moderate effects on recombinant protein substrate recognition for LRRK2; however, Rock is more tolerant of Ala and Glu substitutions in the recombinant protein but not Pro. The Ala substitution in the LRRKtide elicits moderate effects on reaction rate for Rock, however a severe decrease in rate is seen with LRRK2. Pro and Glu substitutions 563 block phosphorylation by LRRK2, with a decrease in reaction rate seen for Rock with these alterations.

+6 Position

Substitution of Gln564 to Ala decreases both LRRK2 and Rock modification of the recombinant substrate.

+7 Position

Substitution of Gly564 to Ala slightly decreases both LRRK2 and Rock modification of the recombinant substrate.

+8 Position

Substitution of Asn564 to Ala slightly increases LRRK2 modification of the recombinant substrate and slightly decreases Rock phosphorylation of recombinant substrate.

Example 5

General Immunoprecipitation and Kinase Assay Protocol

1) Harvest cells by scraping in lysis buffer (500 µl for a 10 cm dish) Lysis Buffer: 50 mM Tris pH 7.5, 1% Triton X-100, 1 mM NaV, 5 mM sodium pyrophosphate, 50 mM NaF, 0.27 M Sucrose, 1 mM EGTA, 1 mM EDTA (Add reducing agent (0.1% β-mercaptoethanol) and inhibitors (1 mM Benzamidine, 1 mM PMSF) before use).
2) Centrifuge lysates 13000 rpm for 25 min at 4° C. and retain supernatant.
3) Perform protein assay.
4) Immunoprecipitate from 1-2 mg total protein lysate using 5 µg LRRK2 100-500 antibody coupled to protein G sepharose (10 ul of 50% slurry per sample).
5) Mix lysates and antibody bound beads for 2 hr at 4° C.
6) Spin down beads (13000 rpm 1 min) and remove lysate.
7) Resuspend beads in 5001 lysis buffer with the addition of 0.5M NaCl.
8) Spin down beads, remove buffer and repeat wash once more with lysis buffer plus 0.5M NaCl then twice more with lysis buffer with no NaCl then once more with 1× kinase assay buffer.
9) Spin down and remove all supernatant. For western blot add 20 µl SDS PAGE sample buffer to beads, heat for 10 min at 70° C. and run on gel.
10) For kinase assay resuspend beads in 50 µl kinase assay buffer and incubate for 20 min at 30° C. Kinase Assay Buffer: 50 mM Tris HCL pH 7.5, 0.1 mM EGTA, 10 mM MgCl, 0.1 mM $^{32}$P ATP (approx 300 cpm/pmol), 0.1% B-mercaptoethanol, 20 uM Nictide substrate.
11) Spot 40 µl of the kinase buffer onto 1.5 cm square Whatman p81 paper and place into 50 mM phosphoric acid to terminate the kinase reaction.

Example 6

Generation of Antibodies to LRRK2

Antibodies to LRRK2 were generated in sheep using the immunogen sequences shown in Table 2 Only the antibodies raised to LRRK2 (100-500) (immunogen shown in FIG. 11) were considered to be useful in immunoprecipitating LRRK2 that retained protein kinase activity and was therefore useful in a protein kinase assay. The antibody S224C raised to (2078-2099) immunoprecipitated LRRK2 but was inhibitory to the kinase activity. Antibody LRRK2 (1245-1259) is considered to be useful in immunoblotting but is not considered to be useful for immunoprecipitation.

TABLE 2

Anti-LRRK2 antibodies

| Sheep No. | Antibody Name | Immunogen Sequence | SEQ ID NO. |
| --- | --- | --- | --- |
| S869B | LRRK2 (1-190) | GST-LRRK2 [DU 6688] | — |
| S137C | LRRK2 (1326-2527) | GST-LRRK2 [DU 10525] | — |
| S348C | LRRK2 (100-500) | LRRK2 (100-500) GST cleaved [DU 13636] | — |
| S407C | LRRK2 (100-500) | LRRK2 (100-500) GST cleaved [DU 13636] | — |

TABLE 2-continued

Anti-LRRK2 antibodies

| Sheep No. | Antibody Name | Immunogen Sequence | SEQ ID NO. |
|---|---|---|---|
| S750B | LRRK2 (16-35) | LKKLIVRLNNVQEGKQIETL [residues 16-35 of human] | 54 |
| S224C | LRRK2 (2078-2099) | KFPNEFDELEIQGKLPDPVKEY [residues 2078-2099 of human] | 55 |
| S374C | LRRK2 (2498-2514) | CINLPHEVQNLEKHIEVR [residues 2498-2514 of human + N-terminal cysteine for coupling]10 | 56 |
| S616B | LRRK2 (2508-2527) | EKHIEVRKELAEKMRRTSVE [residues 2508-2527 of human] | 57 |
| S357C | LRRK2 phospho Ser 910 | VKKKSNS*ISVGEFY [residues 904-917 of human] | 58 |
| S044C | LRRK2 phospho Thr 1503 | CLAKLRKT*IINESLN [residues 1497-1510 of human + N-terminal cysteine for coupling] | 59 |
| S146C | LRRK2 phospho Thr 1503 | CLAKLRKT*IINESLN [residues 1497-1510 of human + N-terminal cysteine for coupling] | 60 |
| . . . | . . . | . . . | |
| S994B | LRRK2 (1245-1259) | CRVEKLHLSHNKLKEI [residues 1245-1259 of mouse + N-terminal cysteine for coupling] | 61 |
| S994B | LRRK2 (2078-2096) | CFPNEFDELAIQGKLPDPV [residues 2078-2096 of mouse + N-terminal cysteine for coupling] | 62 |
| S184C | LRRK2 (2078-2096) | CFPNEFDELAIQGKLPDPV [residues 2078-2096 of mouse + N-terminal cysteine for coupling] | 63 |
| S225C | LRRK2 (2078-2099) | RFPNEFDELAIQGKLPDPVKEY [residues 2078-2099 of mouse] | 64 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A method for identifying a compound expected to be useful in inhibiting LRRK2 protein kinase activity, the method comprising the steps of:
   (1) determining whether a test compound inhibits the protein kinase activity of a LRRK2 polypeptide on a substrate polypeptide, and
   (2) selecting a compound which inhibits said LRRK2 polypeptide protein kinase activity,
   wherein the substrate polypeptide comprises a sequence selected from the group consisting of RLGRDKYKTLRQIRQ (SEQ ID NO:1), RLGRDKYKSLRQIRQ (SEQ ID NO:3), WWRFYTLRRA (SEQ ID NO:65), WWKFYTLRRA (SEQ ID NO:47), WWRFYTLRKA (SEQ ID NO:48), MRQGRDKYKTLRQIRQGNTKQRIDEFEAL (SEQ ID NO:44), VKAGRDKYKTLRQIRQGNTKQRIDEFEAM (SEQ ID NO:45), RLGRDKYK(T/S)LRQIRQGNTKQR (SEQ ID NO:4), RLGWWRFYTLRRARQGNTKQR (SEQ ID NO:51), RLGWWKFYTLRRARQGNTKQR (SEQ ID NO:49), RLGWWRFYTLRKARQGNTKQR (SEQ ID NO:50), moesin (SEQ ID NO:39), ezrin (SEQ ID NO:70), radixin (SEQ ID NO:41), or a fusion peptide thereof.

2. The method of claim 1 wherein the LRRK2 polypeptide is wild type human LRRK2 (SEQ ID NO:69); or a fragment comprising at least residues 1326-2527 of wild type human LRRK2; or a fusion either thereof.

3. The method of claim 1 wherein the LRRK2 polypeptide is human LRRK2 having a naturally occurring mutation of wild type human LRRK2; or a fragment corresponding to at least residues 1326-2527 of human LRRK2; or a fusion either thereof.

4. The method of claim 3 wherein the naturally occurring mutation of human LRRK2 is a mutation associated with Parkinson's Disease (PD).

5. The method of claim 3 wherein the mutation, using the numbering of wild type human LRRK2, is G2019S.

6. The method of claim 2 wherein the LRRK2 polypeptide is a GST fusion polypeptide.

7. The method of claim 5 wherein the LRRK2 polypeptide is GST-LRRK2[1326-2527, G2019S].

8. The method of claim 1 wherein the substrate polypeptide is from 10 to 100 amino acids, is selected from the group consisting of RLGRDKYKTLRQIRQ (SEQ ID NO:1), RLGRDKYKSLRQIRQ (SEQ ID NO:3), WWRFYTLRRA (SEQ ID NO:65), WWKFYTLRRA (SEQ ID NO:47), WWRFYTLRKA (SEQ ID NO:48), MRQGRDKYKTLRQIRQGNTKQRIDEFEAL (SEQ ID NO:44), VKAGRDKYKTLRQIRQGNTKQRIDEFEAM (SEQ ID NO:45), RLGRDKYK(T/S)LRQIRQGNTKQR (SEQ ID NO:4), RLGWWRFYTLRRARQGNTKQR (SEQ ID NO:51), RLGWWKFYTLRRARQGNTKQR (SEQ ID NO:49), RLGWWRFYTLRKARQGNTKQR (SEQ ID NO:50), moesin (SEQ ID NO:39), ezrin (SEQ ID NO:70), radixin (SEQ ID NO:41), or a fusion peptide thereof, and optionally includes up to ten conservative or non-conservative amino acid substitutions at residues other than the T/S residue.

* * * * *

SEQUENCE LISTING

<160> NUMBER OF SEQ ID NOS: 70

<210> SEQ ID NO 1
<211> LENGTH: 15
<212> TYPE: PRT
<213> ORGANISM: Homo sapiens

<400> SEQUENCE: 1

Arg Leu Gly Arg Asp Lys Tyr Lys Thr Leu Arg Gln Ile Arg Gln
1               5                   10                  15

<210> SEQ ID NO 2
<211> LENGTH: 21
<212> TYPE: PRT
<213> ORGANISM: Homo sapiens

<400> SEQUENCE: 2

Arg Leu Gly Arg Asp Lys Tyr Lys Thr Leu Arg Gln Ile Arg Gln Gly
1               5                   10                  15

Asn Thr Lys Gln Arg
            20

<210> SEQ ID NO 3
<211> LENGTH: 15
<212> TYPE: PRT
<213> ORGANISM: Homo sapiens
<220> FEATURE:
<221> NAME/KEY: Variation
<222> LOCATION: (9)..(9)
<223> OTHER INFORMATION: Ser or Thr

<400> SEQUENCE: 3

Arg Leu Gly Arg Asp Lys Tyr Lys Xaa Leu Arg Gln Ile Arg Gln
1               5                   10                  15

<210> SEQ ID NO 4
<211> LENGTH: 21
<212> TYPE: PRT
<213> ORGANISM: Homo sapiens
<220> FEATURE:
<221> NAME/KEY: Variation
<222> LOCATION: (9)..(9)
<223> OTHER INFORMATION: Ser or Thr

<400> SEQUENCE: 4

Arg Leu Gly Arg Asp Lys Tyr Lys Xaa Leu Arg Gln Ile Arg Gln Gly
1               5                   10                  15

Asn Thr Lys Gln Arg
            20

<210> SEQ ID NO 5
<211> LENGTH: 13
<212> TYPE: PRT
<213> ORGANISM: Homo sapiens

<400> SEQUENCE: 5

Ile Gly Leu Gln Met Gly Thr Asn Lys Phe Ala Ser Gln
1               5                   10

<210> SEQ ID NO 6
<211> LENGTH: 13
<212> TYPE: PRT
<213> ORGANISM: Homo sapiens

<400> SEQUENCE: 6

Gln Met Thr Ala Tyr Gly Thr Arg Arg His Leu Tyr Asp
1               5                   10

<210> SEQ ID NO 7
<211> LENGTH: 13
<212> TYPE: PRT
<213> ORGANISM: Homo sapiens

<400> SEQUENCE: 7

Asp Arg Lys Lys Arg Tyr Thr Val Val Gln Asn Pro Tyr
1               5                   10

<210> SEQ ID NO 8
<211> LENGTH: 13
<212> TYPE: PRT
<213> ORGANISM: Homo sapiens

<400> SEQUENCE: 8

Lys Gln Gln Arg Glu Lys Thr Arg Trp Leu Asn Ser Gly
1               5                   10

<210> SEQ ID NO 9
<211> LENGTH: 13
<212> TYPE: PRT
<213> ORGANISM: Homo sapiens

<400> SEQUENCE: 9

Ser Ala Val Arg Leu Arg Ser Ser Val Pro Gly Val Pro
1               5                   10

<210> SEQ ID NO 10
<211> LENGTH: 13
<212> TYPE: PRT
<213> ORGANISM: Homo sapiens

<400> SEQUENCE: 10

Ser Val Arg Arg Ser Tyr Ser Ser Ser Gly Ser Leu
1               5                   10

<210> SEQ ID NO 11
<211> LENGTH: 13
<212> TYPE: PRT
<213> ORGANISM: Homo sapiens

<400> SEQUENCE: 11

Met Glu Arg Arg Arg Ile Thr Ser Ala Ala Arg Arg Ser
1               5                   10

<210> SEQ ID NO 12
<211> LENGTH: 13
<212> TYPE: PRT
<213> ORGANISM: Homo sapiens

<400> SEQUENCE: 12

Thr Ser Ala Ala Arg Arg Ser Tyr Val Ser Ser Gly Glu
1               5                   10

<210> SEQ ID NO 13
<211> LENGTH: 13
<212> TYPE: PRT
<213> ORGANISM: Homo sapiens

<400> SEQUENCE: 13

Gly Pro Gly Thr Arg Leu Ser Leu Ala Arg Met Pro Pro
1               5                   10

<210> SEQ ID NO 14
<211> LENGTH: 13
<212> TYPE: PRT
<213> ORGANISM: Homo sapiens

<400> SEQUENCE: 14

Asn Ile Pro Arg Arg Thr Thr Gln Arg Ile Val Ala Pro
1               5                   10

<210> SEQ ID NO 15
<211> LENGTH: 13
<212> TYPE: PRT
<213> ORGANISM: Homo sapiens

<400> SEQUENCE: 15

Ala Lys Ser Arg Leu Gln Thr Ala Pro Val Pro Met Pro
1               5                   10

<210> SEQ ID NO 16
<211> LENGTH: 13
<212> TYPE: PRT
<213> ORGANISM: Homo sapiens

<400> SEQUENCE: 16

Ile Glu Thr His Lys Leu Thr Phe Arg Glu Asn Ala Arg
1               5                   10

<210> SEQ ID NO 17
<211> LENGTH: 13
<212> TYPE: PRT
<213> ORGANISM: Homo sapiens

<400> SEQUENCE: 17

Thr Ser Pro Arg His Leu Ser Asn Val Ser Ser Ser Gly
1               5                   10

<210> SEQ ID NO 18
<211> LENGTH: 13
<212> TYPE: PRT
<213> ORGANISM: Homo sapiens

<400> SEQUENCE: 18

Ala Ser Pro Arg Arg Leu Ser Asn Val Ser Ser Ser Gly
1               5                   10

<210> SEQ ID NO 19
<211> LENGTH: 13
<212> TYPE: PRT
<213> ORGANISM: Homo sapiens

<400> SEQUENCE: 19

Gly Arg Asp Lys Tyr Lys Thr Leu Arg Gln Ile Arg Gln
1               5                   10

<210> SEQ ID NO 20
<211> LENGTH: 13
<212> TYPE: PRT
<213> ORGANISM: Homo sapiens

<400> SEQUENCE: 20

Pro Arg Glu Lys Arg Arg Ser Thr Gly Val Ser Phe Trp
1               5                   10

<210> SEQ ID NO 21

```
<211> LENGTH: 13
<212> TYPE: PRT
<213> ORGANISM: Homo sapiens

<400> SEQUENCE: 21

Arg Pro Gln Arg Ala Thr Ser Asn Val Phe Ala Met Phe
1               5                   10

<210> SEQ ID NO 22
<211> LENGTH: 13
<212> TYPE: PRT
<213> ORGANISM: Homo sapiens

<400> SEQUENCE: 22

Lys Lys Lys Lys Arg Phe Ser Phe Lys Lys Ser Phe Lys
1               5                   10

<210> SEQ ID NO 23
<211> LENGTH: 13
<212> TYPE: PRT
<213> ORGANISM: Homo sapiens

<400> SEQUENCE: 23

Gly Ser Ser Lys His Asn Thr Ile Lys Lys Leu Tyr Leu
1               5                   10

<210> SEQ ID NO 24
<211> LENGTH: 5
<212> TYPE: PRT
<213> ORGANISM: Homo sapiens
<220> FEATURE:
<221> NAME/KEY: Phosphorylation
<222> LOCATION: (3)..(3)
<223> OTHER INFORMATION: Phospho threonine

<400> SEQUENCE: 24

Tyr Lys Thr Leu Arg
1               5

<210> SEQ ID NO 25
<211> LENGTH: 7
<212> TYPE: PRT
<213> ORGANISM: Homo sapiens
<220> FEATURE:
<221> NAME/KEY: Phosphorylation
<222> LOCATION: (5)..(5)
<223> OTHER INFORMATION: Phospho threonine

<400> SEQUENCE: 25

Asp Lys Tyr Lys Thr Leu Arg
1               5

<210> SEQ ID NO 26
<211> LENGTH: 10
<212> TYPE: PRT
<213> ORGANISM: Homo sapiens
<220> FEATURE:
<221> NAME/KEY: Phosphorylation
<222> LOCATION: (3)..(3)
<223> OTHER INFORMATION: Phospho threonine

<400> SEQUENCE: 26

Ala Leu Thr Ser Glu Leu Ala Asn Ala Arg
1               5                   10

<210> SEQ ID NO 27
<211> LENGTH: 5
<212> TYPE: PRT
```

```
<213> ORGANISM: Homo sapiens
<220> FEATURE:
<221> NAME/KEY: Phosphorylation
<222> LOCATION: (3)..(3)
<223> OTHER INFORMATION: Phospho serine

<400> SEQUENCE: 27

Arg Pro Ser Gln Arg
1               5

<210> SEQ ID NO 28
<211> LENGTH: 8
<212> TYPE: PRT
<213> ORGANISM: Homo sapiens
<220> FEATURE:
<221> NAME/KEY: Phosphorylation
<222> LOCATION: (1)..(1)
<223> OTHER INFORMATION: Phospho threonine

<400> SEQUENCE: 28

Thr Pro Pro Pro Ser Gln Gly Lys
1               5

<210> SEQ ID NO 29
<211> LENGTH: 10
<212> TYPE: PRT
<213> ORGANISM: Homo sapiens
<220> FEATURE:
<221> NAME/KEY: Phosphorylation
<222> LOCATION: (7)..(7)
<223> OTHER INFORMATION: Phospho threonine

<400> SEQUENCE: 29

Gly His Asp Ala Gln Gly Thr Leu Ser Lys
1               5                   10

<210> SEQ ID NO 30
<211> LENGTH: 12
<212> TYPE: PRT
<213> ORGANISM: Homo sapiens
<220> FEATURE:
<221> NAME/KEY: Phosphorylation
<222> LOCATION: (7)..(7)
<223> OTHER INFORMATION: Phospho threonine

<400> SEQUENCE: 30

Tyr Leu Ala Ser Ala Ser Thr Met Asp His Ala Arg
1               5                   10

<210> SEQ ID NO 31
<211> LENGTH: 6
<212> TYPE: PRT
<213> ORGANISM: Homo sapiens
<220> FEATURE:
<221> NAME/KEY: Phosphorylation
<222> LOCATION: (4)..(4)
<223> OTHER INFORMATION: Phospho threonine

<400> SEQUENCE: 31

Asn Ile Val Thr Pro Arg
1               5

<210> SEQ ID NO 32
<211> LENGTH: 10
<212> TYPE: PRT
<213> ORGANISM: Homo sapiens
<220> FEATURE:
<221> NAME/KEY: PHOSPHORYLATION
<222> LOCATION: (1)..(1)
<223> OTHER INFORMATION: Phospho threonine
```

<400> SEQUENCE: 32

Thr Thr His Tyr Gly Ser Leu Pro Gln Lys
1               5                   10

<210> SEQ ID NO 33
<211> LENGTH: 11
<212> TYPE: PRT
<213> ORGANISM: Homo sapiens

<400> SEQUENCE: 33

Leu Met Ile Val Gly Asn Thr Gly Ser Gly Lys
1               5                   10

<210> SEQ ID NO 34
<211> LENGTH: 11
<212> TYPE: PRT
<213> ORGANISM: Homo sapiens

<400> SEQUENCE: 34

Thr Thr Leu Leu Gln Gln Leu Met Lys Thr Lys
1               5                   10

<210> SEQ ID NO 35
<211> LENGTH: 13
<212> TYPE: PRT
<213> ORGANISM: Homo sapiens
<220> FEATURE:
<221> NAME/KEY: Phosphorylation
<222> LOCATION: (4)..(4)
<223> OTHER INFORMATION: Phospho threonine

<400> SEQUENCE: 35

Leu Arg Lys Thr Ile Ile Asn Glu Ser Leu Asn Phe Lys
1               5                   10

<210> SEQ ID NO 36
<211> LENGTH: 16
<212> TYPE: PRT
<213> ORGANISM: Homo sapiens
<220> FEATURE:
<221> NAME/KEY: Phosphorylation
<222> LOCATION: (2)..(2)
<223> OTHER INFORMATION: Phospho serine

<400> SEQUENCE: 36

Gly Ser Leu Glu Val Leu Phe Gln Gly Pro Leu Gly Ser Leu Lys Lys
1               5                   10                  15

<210> SEQ ID NO 37
<211> LENGTH: 14
<212> TYPE: PRT
<213> ORGANISM: Homo sapiens
<220> FEATURE:
<221> NAME/KEY: Phosphorylation
<222> LOCATION: (12)..(12)
<223> OTHER INFORMATION: Phospho threonine

<400> SEQUENCE: 37

Glu Glu Phe Tyr Ser Thr His Pro His Phe Met Thr Gln Arg
1               5                   10

<210> SEQ ID NO 38
<211> LENGTH: 19
<212> TYPE: PRT
<213> ORGANISM: Homo sapiens

<400> SEQUENCE: 38

```
Ala Ser Ser Pro Val Ile Leu Val Gly Thr His Leu Asp Val Ser
1               5                   10                  15

Asp Glu Lys

<210> SEQ ID NO 39
<211> LENGTH: 577
<212> TYPE: PRT
<213> ORGANISM: Homo sapiens

<400> SEQUENCE: 39

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
                20                  25                  30

Val Val Lys Thr Ile Gly Leu Arg Glu Val Trp Phe Phe Gly Leu Gln
            35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Leu Ile Gln Asp
                85                  90                  95

Ile Thr Gln Arg Leu Phe Phe Leu Gln Val Lys Glu Gly Ile Leu Asn
                100                 105                 110

Asp Asp Ile Tyr Cys Pro Pro Glu Thr Ala Val Leu Leu Ala Ser Tyr
            115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
                180                 185                 190

Lys Ile Ala Gln Asp Leu Glu Met Tyr Gly Val Asn Tyr Phe Ser Ile
            195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Ala Leu Cys Met Gly Asn His
            275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Met Glu Arg
305                 310                 315                 320

Ala Met Leu Glu Asn Glu Lys Lys Arg Glu Met Ala Glu Lys Glu
                325                 330                 335

Lys Glu Lys Ile Glu Arg Glu Lys Glu Glu Leu Met Glu Arg Leu Lys
                340                 345                 350
```

-continued

```
Gln Ile Glu Glu Gln Thr Lys Lys Ala Gln Gln Leu Glu Glu Gln
        355                 360                 365

Thr Arg Arg Ala Leu Glu Leu Glu Gln Glu Arg Lys Arg Ala Gln Ser
    370                 375                 380

Glu Ala Glu Lys Leu Ala Lys Glu Arg Gln Glu Ala Glu Glu Ala Lys
385                 390                 395                 400

Glu Ala Leu Leu Gln Ala Ser Arg Asp Gln Lys Lys Thr Gln Glu Gln
                405                 410                 415

Leu Ala Leu Glu Met Ala Glu Leu Thr Ala Arg Ile Ser Gln Leu Glu
            420                 425                 430

Met Ala Arg Gln Lys Lys Glu Ser Glu Ala Val Glu Trp Gln Gln Lys
        435                 440                 445

Ala Gln Met Val Gln Glu Asp Leu Glu Lys Thr Arg Ala Glu Leu Lys
    450                 455                 460

Thr Ala Met Ser Thr Pro His Val Ala Glu Pro Ala Glu Asn Glu Gln
465                 470                 475                 480

Asp Glu Gln Asp Glu Asn Gly Ala Glu Ala Ser Ala Asp Leu Arg Ala
                485                 490                 495

Asp Ala Met Ala Lys Asp Arg Ser Glu Glu Arg Thr Thr Glu Ala
            500                 505                 510

Glu Lys Asn Glu Arg Val Gln Lys His Leu Lys Ala Leu Thr Ser Glu
        515                 520                 525

Leu Ala Asn Ala Arg Asp Glu Ser Lys Lys Thr Ala Asn Asp Met Ile
    530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
                565                 570                 575

Met
```

```
<210> SEQ ID NO 40
<211> LENGTH: 586
<212> TYPE: PRT
<213> ORGANISM: Homo sapiens

<400> SEQUENCE: 40

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45

Tyr Val Asp Asn Lys Gly Phe Pro Thr Trp Leu Lys Leu Asp Lys Lys
    50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
        115                 120                 125

Ala Val Gln Ala Lys Phe Gly Asp Tyr Asn Lys Glu Val His Lys Ser
    130                 135                 140

Gly Tyr Leu Ser Ser Glu Arg Leu Ile Pro Gln Arg Val Met Asp Gln
```

```
            145                 150                 155                 160
His Lys Leu Thr Arg Asp Gln Trp Glu Asp Arg Ile Gln Val Trp His
            165                 170                 175
Ala Glu His Arg Gly Met Leu Lys Asp Asn Ala Met Leu Glu Tyr Leu
            180                 185                 190
Lys Ile Ala Gln Asp Leu Glu Met Tyr Gly Ile Asn Tyr Phe Glu Ile
            195                 200                 205
Lys Asn Lys Lys Gly Thr Asp Leu Trp Leu Gly Val Asp Ala Leu Gly
            210                 215                 220
Leu Asn Ile Tyr Glu Lys Asp Lys Leu Thr Pro Lys Ile Gly Phe
225                 230                 235                 240
Pro Trp Ser Glu Ile Arg Asn Ile Ser Phe Asn Asp Lys Lys Phe Val
            245                 250                 255
Ile Lys Pro Ile Asp Lys Lys Ala Pro Asp Phe Val Phe Tyr Ala Pro
            260                 265                 270
Arg Leu Arg Ile Asn Lys Arg Ile Leu Gln Leu Cys Met Gly Asn His
            275                 280                 285
Glu Leu Tyr Met Arg Arg Lys Pro Asp Thr Ile Glu Val Gln Gln
            290                 295                 300
Met Lys Ala Gln Ala Arg Glu Glu Lys His Gln Lys Gln Leu Glu Arg
305                 310                 315                 320
Gln Gln Leu Glu Thr Glu Lys Lys Arg Arg Glu Thr Val Glu Arg Glu
            325                 330                 335
Lys Glu Gln Met Met Arg Glu Lys Glu Glu Leu Met Leu Arg Leu Gln
            340                 345                 350
Asp Tyr Glu Glu Lys Thr Lys Lys Ala Glu Arg Glu Leu Ser Glu Gln
            355                 360                 365
Ile Gln Arg Ala Leu Gln Leu Glu Glu Glu Arg Lys Arg Ala Gln Glu
            370                 375                 380
Glu Ala Glu Arg Leu Glu Ala Asp Arg Met Ala Ala Leu Arg Ala Lys
385                 390                 395                 400
Glu Glu Leu Glu Arg Gln Ala Val Asp Gln Ile Lys Ser Gln Glu Gln
            405                 410                 415
Leu Ala Ala Glu Leu Ala Glu Tyr Thr Ala Lys Ile Ala Leu Leu Glu
            420                 425                 430
Glu Ala Arg Arg Arg Lys Glu Asp Glu Val Glu Glu Trp Gln His Arg
            435                 440                 445
Ala Lys Glu Ala Gln Asp Asp Leu Val Lys Thr Lys Glu Glu Leu His
            450                 455                 460
Leu Val Met Thr Ala Pro Pro Pro Pro Pro Val Tyr Glu Pro
465                 470                 475                 480
Val Ser Tyr His Val Gln Glu Ser Leu Gln Asp Glu Gly Ala Glu Pro
            485                 490                 495
Thr Gly Tyr Ser Ala Glu Leu Ser Ser Glu Gly Ile Arg Asp Asp Arg
            500                 505                 510
Asn Glu Glu Lys Arg Ile Thr Glu Ala Glu Lys Asn Glu Arg Val Gln
            515                 520                 525
Arg Gln Leu Val Thr Leu Ser Ser Glu Leu Ser Gln Ala Arg Asp Glu
            530                 535                 540
Asn Lys Arg Thr His Asn Asp Ile Ile His Asn Glu Asn Met Arg Gln
545                 550                 555                 560
Gly Arg Asp Lys Tyr Lys Thr Leu Arg Gln Ile Arg Gln Gly Asn Thr
            565                 570                 575
```

Lys Gln Arg Ile Asp Glu Phe Glu Ala Leu
            580                 585

<210> SEQ ID NO 41
<211> LENGTH: 583
<212> TYPE: PRT
<213> ORGANISM: Homo sapiens

<400> SEQUENCE: 41

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Val Gly Leu Arg Glu Val Trp Phe Phe Gly Leu Gln
            35                  40                  45

Tyr Val Asp Ser Lys Gly Tyr Ser Thr Trp Leu Lys Leu Asn Lys Lys
        50                  55                  60

Val Thr Gln Gln Asp Val Lys Lys Glu Asn Pro Leu Gln Phe Lys Phe
65                  70                  75                  80

Arg Ala Lys Phe Phe Pro Glu Asp Val Ser Glu Glu Leu Ile Gln Glu
                85                  90                  95

Ile Thr Gln Arg Leu Phe Phe Leu Gln Val Lys Glu Ala Ile Leu Asn
            100                 105                 110

Asp Glu Ile Tyr Cys Pro Pro Glu Thr Ala Val Leu Leu Ala Ser Tyr
        115                 120                 125

Ala Val Gln Ala Lys Tyr Gly Asp Tyr Asn Lys Glu Ile His Lys Pro
    130                 135                 140

Gly Tyr Leu Ala Asn Asp Arg Leu Leu Pro Gln Arg Val Leu Glu Gln
145                 150                 155                 160

His Lys Leu Thr Lys Glu Gln Trp Glu Glu Arg Ile Gln Asn Trp His
                165                 170                 175

Glu Glu His Arg Gly Met Leu Arg Glu Asp Ser Met Met Glu Tyr Leu
            180                 185                 190

Lys Ile Ala Gln Asp Leu Glu Met Tyr Gly Val Asn Tyr Phe Glu Ile
        195                 200                 205

Lys Asn Lys Lys Gly Thr Glu Leu Trp Leu Gly Val Asp Ala Leu Gly
    210                 215                 220

Leu Asn Ile Tyr Glu His Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Leu Glu Arg
305                 310                 315                 320

Ala Gln Leu Glu Asn Glu Lys Glu Arg Glu Ile Ala Glu Lys Glu
                325                 330                 335

Lys Glu Arg Ile Glu Arg Glu Lys Glu Glu Leu Met Glu Arg Leu Lys
            340                 345                 350

Gln Ile Glu Glu Gln Thr Ile Lys Ala Gln Lys Glu Leu Glu Glu Gln
        355                 360                 365

```
Thr Arg Lys Ala Leu Glu Leu Asp Gln Glu Arg Lys Arg Ala Lys Glu
        370                 375                 380

Glu Ala Glu Arg Leu Glu Lys Glu Arg Arg Ala Glu Glu Ala Lys
385                 390                 395                 400

Ser Ala Ile Ala Lys Gln Ala Ala Asp Gln Met Lys Asn Gln Glu Gln
                405                 410                 415

Leu Ala Ala Glu Leu Ala Glu Phe Thr Ala Lys Ile Ala Leu Leu Glu
                420                 425                 430

Glu Ala Lys Lys Lys Lys Glu Glu Glu Ala Thr Glu Trp Gln His Lys
                435                 440                 445

Ala Phe Ala Ala Gln Glu Asp Leu Glu Lys Thr Lys Glu Glu Leu Lys
        450                 455                 460

Thr Val Met Ser Ala Pro Pro Pro Pro Pro Pro Val Ile Pro
465                 470                 475                 480

Pro Thr Glu Asn Glu His Asp Glu His Asp Glu Asn Asn Ala Glu Ala
                485                 490                 495

Ser Ala Glu Leu Ser Asn Glu Gly Val Met Asn His Arg Ser Glu Glu
                500                 505                 510

Glu Arg Val Thr Glu Thr Gln Lys Asn Glu Arg Val Lys Lys Gln Leu
                515                 520                 525

Gln Ala Leu Ser Ser Glu Leu Ala Gln Ala Arg Asp Glu Thr Lys Lys
        530                 535                 540

Thr Gln Asn Asp Val Leu His Ala Glu Asn Val Lys Ala Gly Arg Asp
545                 550                 555                 560

Lys Tyr Lys Thr Leu Arg Gln Ile Arg Gln Gly Asn Thr Lys Gln Arg
                565                 570                 575

Ile Asp Glu Phe Glu Ala Met
                580

<210> SEQ ID NO 42
<211> LENGTH: 595
<212> TYPE: PRT
<213> ORGANISM: Homo sapiens

<400> SEQUENCE: 42

Met Ala Gly Ala Ile Ala Ser Arg Met Ser Phe Ser Ser Leu Lys Arg
1               5                   10                  15

Lys Gln Pro Lys Thr Phe Thr Val Arg Ile Val Thr Met Asp Ala Glu
                20                  25                  30

Met Glu Phe Asn Cys Glu Met Lys Trp Lys Gly Lys Asp Leu Phe Asp
                35                  40                  45

Leu Val Cys Arg Thr Leu Gly Leu Arg Glu Thr Trp Phe Phe Gly Leu
        50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Glu Leu Val Gln Glu
                100                 105                 110

Ile Thr Gln His Leu Phe Phe Leu Gln Val Lys Lys Gln Ile Leu Asp
                115                 120                 125

Glu Lys Ile Tyr Cys Pro Pro Glu Ala Ser Val Leu Leu Ala Ser Tyr
        130                 135                 140

Ala Val Gln Ala Lys Tyr Gly Asp Tyr Asp Pro Ser Val His Lys Arg
145                 150                 155                 160
```

-continued

```
Gly Phe Leu Ala Gln Glu Glu Leu Leu Pro Lys Arg Val Ile Asn Leu
                165                 170                 175
Tyr Gln Met Thr Pro Glu Met Trp Glu Arg Ile Thr Ala Trp Tyr
            180                 185                 190
Ala Glu His Arg Gly Arg Ala Arg Asp Glu Ala Glu Met Glu Tyr Leu
                195                 200                 205
Lys Ile Ala Gln Asp Leu Glu Met Tyr Gly Val Asn Tyr Phe Ala Ile
            210                 215                 220
Arg Asn Lys Lys Gly Thr Glu Leu Leu Leu Gly Val Asp Ala Leu Gly
225                 230                 235                 240
Leu His Ile Tyr Asp Pro Glu Asn Arg Leu Thr Pro Lys Ile Ser Phe
                245                 250                 255
Pro Trp Asn Glu Ile Arg Asn Ile Ser Tyr Ser Asp Lys Glu Phe Thr
            260                 265                 270
Ile Lys Pro Leu Asp Lys Lys Ile Asp Val Phe Lys Phe Asn Ser Ser
            275                 280                 285
Lys Leu Arg Val Asn Lys Leu Ile Leu Gln Leu Cys Ile Gly Asn His
            290                 295                 300
Asp Leu Phe Met Arg Arg Lys Ala Asp Ser Leu Glu Val Gln Gln
305                 310                 315                 320
Met Lys Ala Gln Ala Arg Glu Glu Lys Ala Arg Lys Gln Met Glu Arg
                325                 330                 335
Gln Arg Leu Ala Arg Glu Lys Gln Met Arg Glu Ala Glu Arg Thr
            340                 345                 350
Arg Asp Glu Leu Glu Arg Arg Leu Leu Gln Met Lys Glu Glu Ala Thr
            355                 360                 365
Met Ala Asn Glu Ala Leu Met Arg Ser Glu Glu Thr Ala Asp Leu Leu
370                 375                 380
Ala Glu Lys Ala Gln Ile Thr Glu Glu Glu Ala Lys Leu Leu Ala Gln
385                 390                 395                 400
Lys Ala Ala Glu Ala Glu Gln Glu Met Gln Arg Ile Lys Ala Thr Ala
                405                 410                 415
Ile Arg Thr Glu Glu Glu Lys Arg Leu Met Glu Gln Lys Val Leu Glu
            420                 425                 430
Ala Glu Val Leu Ala Leu Lys Met Ala Glu Glu Ser Glu Arg Arg Ala
            435                 440                 445
Lys Glu Ala Asp Gln Leu Lys Gln Asp Leu Gln Glu Ala Arg Glu Ala
            450                 455                 460
Glu Arg Arg Ala Lys Gln Lys Leu Leu Glu Ile Ala Thr Lys Pro Thr
465                 470                 475                 480
Tyr Pro Pro Met Asn Pro Ile Pro Ala Pro Leu Pro Pro Asp Ile Pro
                485                 490                 495
Ser Phe Asn Leu Ile Gly Asp Ser Leu Ser Phe Asp Phe Lys Asp Thr
            500                 505                 510
Asp Met Lys Arg Leu Ser Met Glu Ile Glu Lys Glu Lys Val Glu Tyr
            515                 520                 525
Met Glu Lys Ser Lys His Leu Gln Glu Gln Leu Asn Glu Leu Lys Thr
            530                 535                 540
Glu Ile Glu Ala Leu Lys Leu Lys Glu Arg Glu Thr Ala Leu Asp Ile
545                 550                 555                 560
Leu His Asn Glu Asn Ser Asp Arg Gly Gly Ser Ser Lys His Asn Thr
                565                 570                 575
Ile Lys Lys Leu Thr Leu Gln Ser Ala Lys Ser Arg Val Ala Phe Phe
            580                 585                 590
```

Glu Glu Leu
        595

<210> SEQ ID NO 43
<211> LENGTH: 29
<212> TYPE: PRT
<213> ORGANISM: Homo sapiens

<400> SEQUENCE: 43

Met Arg Leu Gly Arg Asp Lys Tyr Lys Thr Leu Arg Gln Ile Arg Gln
1               5                   10                  15

Gly Asn Thr Lys Gln Arg Ile Asp Glu Phe Glu Ser Met
            20                  25

<210> SEQ ID NO 44
<211> LENGTH: 29
<212> TYPE: PRT
<213> ORGANISM: Homo sapiens

<400> SEQUENCE: 44

Met Arg Gln Gly Arg Asp Lys Tyr Lys Thr Leu Arg Gln Ile Arg Gln
1               5                   10                  15

Gly Asn Thr Lys Gln Arg Ile Asp Glu Phe Glu Ala Leu
            20                  25

<210> SEQ ID NO 45
<211> LENGTH: 29
<212> TYPE: PRT
<213> ORGANISM: Homo sapiens

<400> SEQUENCE: 45

Val Lys Ala Gly Arg Asp Lys Tyr Lys Thr Leu Arg Gln Ile Arg Gln
1               5                   10                  15

Gly Asn Thr Lys Gln Arg Ile Asp Glu Phe Glu Ala Met
            20                  25

<210> SEQ ID NO 46
<211> LENGTH: 29
<212> TYPE: PRT
<213> ORGANISM: Homo sapiens

<400> SEQUENCE: 46

Asp Arg Gly Gly Ser Ser Lys His Asn Thr Ile Lys Lys Leu Thr Leu
1               5                   10                  15

Gln Ser Ala Lys Ser Arg Val Ala Phe Phe Glu Glu Leu
            20                  25

<210> SEQ ID NO 47
<211> LENGTH: 17
<212> TYPE: PRT
<213> ORGANISM: Artificial
<220> FEATURE:
<223> OTHER INFORMATION: Recombinant protein

<400> SEQUENCE: 47

Arg Leu Gly Arg Asp Lys Tyr Lys Thr Leu Arg Gln Ile Arg Gln Gly
1               5                   10                  15

Asn

<210> SEQ ID NO 48
<211> LENGTH: 10
<212> TYPE: PRT
<213> ORGANISM: Artificial

```
<220> FEATURE:
<223> OTHER INFORMATION: Recombinant protein

<400> SEQUENCE: 48

Trp Trp Arg Phe Tyr Thr Leu Arg Lys Ala
1               5                   10

<210> SEQ ID NO 49
<211> LENGTH: 21
<212> TYPE: PRT
<213> ORGANISM: Artificial
<220> FEATURE:
<223> OTHER INFORMATION: Recombinant protein

<400> SEQUENCE: 49

Arg Leu Gly Trp Trp Lys Phe Tyr Thr Leu Arg Arg Ala Arg Gln Gly
1               5                   10                  15

Asn Thr Lys Gln Arg
            20

<210> SEQ ID NO 50
<211> LENGTH: 21
<212> TYPE: PRT
<213> ORGANISM: Artificial
<220> FEATURE:
<223> OTHER INFORMATION: Recombinant protein

<400> SEQUENCE: 50

Arg Leu Gly Trp Trp Arg Phe Tyr Thr Leu Arg Lys Ala Arg Gln Gly
1               5                   10                  15

Asn Thr Lys Gln Arg
            20

<210> SEQ ID NO 51
<211> LENGTH: 21
<212> TYPE: PRT
<213> ORGANISM: Artificial
<220> FEATURE:
<223> OTHER INFORMATION: Recombinant protein

<400> SEQUENCE: 51

Arg Leu Gly Trp Trp Arg Phe Tyr Thr Leu Arg Arg Ala Arg Gln Gly
1               5                   10                  15

Asn Thr Lys Gln Arg
            20

<210> SEQ ID NO 52
<211> LENGTH: 10
<212> TYPE: PRT
<213> ORGANISM: Artificial
<220> FEATURE:
<223> OTHER INFORMATION: Recombinant protein
<220> FEATURE:
<221> NAME/KEY: Variation
<222> LOCATION: (1)..(1)
<223> OTHER INFORMATION: Trp, Phe, Arg or Lys
<220> FEATURE:
<221> NAME/KEY: Variation
<222> LOCATION: (2)..(2)
<223> OTHER INFORMATION: Trp, Phe, Arg or Lys
<220> FEATURE:
<221> NAME/KEY: Variation
<222> LOCATION: (3)..(3)
<223> OTHER INFORMATION: Arg or Lys
<220> FEATURE:
<221> NAME/KEY: Variation
<222> LOCATION: (4)..(4)
<223> OTHER INFORMATION: Phe,Trp, His or Arg
<220> FEATURE:
```

```
<221> NAME/KEY: Variation
<222> LOCATION: (5)..(5)
<223> OTHER INFORMATION: Tyr, Trp or Arg
<220> FEATURE:
<221> NAME/KEY: Variation
<222> LOCATION: (6)..(6)
<223> OTHER INFORMATION: Ser or Thr
<220> FEATURE:
<221> NAME/KEY: Variation
<222> LOCATION: (7)..(7)
<223> OTHER INFORMATION: Leu, Val or Ile
<220> FEATURE:
<221> NAME/KEY: Variation
<222> LOCATION: (8)..(8)
<223> OTHER INFORMATION: Arg or Lys
<220> FEATURE:
<221> NAME/KEY: Variation
<222> LOCATION: (9)..(9)
<223> OTHER INFORMATION: Arg or Lys
<220> FEATURE:
<221> NAME/KEY: Variation
<222> LOCATION: (10)..(10)
<223> OTHER INFORMATION: Ala or Tyr

<400> SEQUENCE: 52

Xaa Xaa Xaa Xaa Xaa Xaa Xaa Xaa Xaa Xaa
1               5                   10

<210> SEQ ID NO 53
<211> LENGTH: 21
<212> TYPE: PRT
<213> ORGANISM: Artificial
<220> FEATURE:
<223> OTHER INFORMATION: Recombinant protein

<400> SEQUENCE: 53

Arg Leu Gly Trp Trp Arg Phe Tyr Ala Leu Arg Arg Ala Arg Gln Gly
1               5                   10                  15

Asn Thr Lys Gln Arg
            20

<210> SEQ ID NO 54
<211> LENGTH: 20
<212> TYPE: PRT
<213> ORGANISM: Homo sapiens

<400> SEQUENCE: 54

Leu Lys Lys Leu Ile Val Arg Leu Asn Asn Val Gln Glu Gly Lys Gln
1               5                   10                  15

Ile Glu Thr Leu
            20

<210> SEQ ID NO 55
<211> LENGTH: 22
<212> TYPE: PRT
<213> ORGANISM: Homo sapiens

<400> SEQUENCE: 55

Lys Phe Pro Asn Glu Phe Asp Glu Leu Glu Ile Gln Gly Lys Leu Pro
1               5                   10                  15

Asp Pro Val Lys Glu Tyr
            20

<210> SEQ ID NO 56
<211> LENGTH: 18
<212> TYPE: PRT
<213> ORGANISM: Homo sapiens

<400> SEQUENCE: 56
```

```
Cys Ile Asn Leu Pro His Glu Val Gln Asn Leu Glu Lys His Ile Glu
1               5                   10                  15

Val Arg

<210> SEQ ID NO 57
<211> LENGTH: 20
<212> TYPE: PRT
<213> ORGANISM: Homo sapiens

<400> SEQUENCE: 57

Glu Lys His Ile Glu Val Arg Lys Glu Leu Ala Glu Lys Met Arg Arg
1               5                   10                  15

Thr Ser Val Glu
            20

<210> SEQ ID NO 58
<211> LENGTH: 14
<212> TYPE: PRT
<213> ORGANISM: Homo sapiens
<220> FEATURE:
<221> NAME/KEY: Phosphorylation
<222> LOCATION: (7)..(7)
<223> OTHER INFORMATION: Phospho serine

<400> SEQUENCE: 58

Val Lys Lys Lys Ser Asn Ser Ile Ser Val Gly Glu Phe Tyr
1               5                   10

<210> SEQ ID NO 59
<211> LENGTH: 15
<212> TYPE: PRT
<213> ORGANISM: Homo sapiens
<220> FEATURE:
<221> NAME/KEY: Phosphorylation
<222> LOCATION: (8)..(8)
<223> OTHER INFORMATION: Phospho threonine

<400> SEQUENCE: 59

Cys Leu Ala Lys Leu Arg Lys Thr Ile Ile Asn Glu Ser Leu Asn
1               5                   10                  15

<210> SEQ ID NO 60
<211> LENGTH: 15
<212> TYPE: PRT
<213> ORGANISM: Homo sapiens
<220> FEATURE:
<221> NAME/KEY: Phosphorylation
<222> LOCATION: (8)..(8)
<223> OTHER INFORMATION: Phospho threonine

<400> SEQUENCE: 60

Cys Leu Ala Lys Leu Arg Lys Thr Ile Ile Asn Glu Ser Leu Asn
1               5                   10                  15

<210> SEQ ID NO 61
<211> LENGTH: 16
<212> TYPE: PRT
<213> ORGANISM: Mus sp.

<400> SEQUENCE: 61

Cys Arg Val Glu Lys Leu His Leu Ser His Asn Lys Leu Lys Glu Ile
1               5                   10                  15

<210> SEQ ID NO 62
<211> LENGTH: 19
<212> TYPE: PRT
```

-continued

<213> ORGANISM: Mus sp.

<400> SEQUENCE: 62

Cys Phe Pro Asn Glu Phe Asp Glu Leu Ala Ile Gln Gly Lys Leu Pro
1               5                   10                  15

Asp Pro Val

<210> SEQ ID NO 63
<211> LENGTH: 19
<212> TYPE: PRT
<213> ORGANISM: Mus sp.

<400> SEQUENCE: 63

Cys Phe Pro Asn Glu Phe Asp Glu Leu Ala Ile Gln Gly Lys Leu Pro
1               5                   10                  15

Asp Pro Val

<210> SEQ ID NO 64
<211> LENGTH: 22
<212> TYPE: PRT
<213> ORGANISM: Mus sp.

<400> SEQUENCE: 64

Arg Phe Pro Asn Glu Phe Asp Glu Leu Ala Ile Gln Gly Lys Leu Pro
1               5                   10                  15

Asp Pro Val Lys Glu Tyr
            20

<210> SEQ ID NO 65
<211> LENGTH: 10
<212> TYPE: PRT
<213> ORGANISM: Artificial
<220> FEATURE:
<223> OTHER INFORMATION: Recombinant protein

<400> SEQUENCE: 65

Trp Trp Arg Phe Tyr Thr Leu Arg Arg Ala
1               5                   10

<210> SEQ ID NO 66
<211> LENGTH: 404
<212> TYPE: PRT
<213> ORGANISM: Artificial
<220> FEATURE:
<223> OTHER INFORMATION: Recombinant protein

<400> SEQUENCE: 66

Gly Pro Leu Gly Ser Met Gly Pro Gln Asp Val Gly Asn Asp Trp Glu
1               5                   10                  15

Val Leu Gly Val His Gln Leu Ile Leu Lys Met Leu Thr Val His Asn
                20                  25                  30

Ala Ser Val Asn Leu Ser Val Ile Gly Leu Lys Thr Leu Asp Leu Leu
            35                  40                  45

Leu Thr Ser Gly Lys Ile Thr Leu Leu Ile Leu Asp Glu Glu Ser Asp
        50                  55                  60

Ile Phe Met Leu Ile Phe Asp Ala Met His Ser Phe Pro Ala Asn Asp
65                  70                  75                  80

Glu Val Gln Lys Leu Gly Cys Lys Ala Leu His Val Leu Phe Glu Arg
                85                  90                  95

Val Ser Glu Glu Gln Leu Thr Gly Phe Val Glu Asn Lys Asp Tyr Met
                100                 105                 110

```
Ile Leu Leu Ser Ala Leu Thr Asn Phe Lys Asp Glu Glu Ile Val
        115                 120                 125
Leu His Val Leu His Cys Leu His Ser Leu Ala Ile Pro Cys Asn Asn
130                 135                 140
Val Glu Val Leu Met Ser Gly Asn Val Arg Cys Tyr Asn Ile Val Val
145                 150                 155                 160
Glu Ala Met Lys Ala Phe Pro Met Ser Glu Arg Ile Gln Glu Val Ser
                165                 170                 175
Cys Cys Leu Leu His Arg Leu Thr Leu Gly Asn Phe Phe Asn Ile Leu
                180                 185                 190
Val Leu Asn Glu Val His Glu Phe Val Val Lys Ala Val Gln Gln Tyr
                195                 200                 205
Pro Glu Asn Ala Ala Leu Gln Ile Ser Ala Leu Ser Cys Leu Ala Leu
                210                 215                 220
Leu Thr Glu Thr Ile Phe Leu Asn Gln Asp Leu Glu Glu Lys Asn Glu
225                 230                 235                 240
Asn Gln Glu Asn Asp Asp Glu Gly Glu Asp Lys Leu Phe Trp Leu
                245                 250                 255
Glu Ala Cys Tyr Lys Ala Leu Thr Trp His Arg Lys Asn Lys His Val
                260                 265                 270
Gln Glu Ala Ala Cys Trp Ala Leu Asn Asn Leu Leu Met Tyr Gln Asn
                275                 280                 285
Ser Leu His Glu Lys Ile Gly Asp Glu Asp Gly His Phe Pro Ala His
                290                 295                 300
Arg Glu Val Met Leu Ser Met Leu Met His Ser Ser Lys Glu Val
305                 310                 315                 320
Phe Gln Ala Ser Ala Asn Ala Leu Ser Thr Leu Leu Glu Gln Asn Val
                325                 330                 335
Asn Phe Arg Lys Ile Leu Leu Ser Lys Gly Ile His Leu Asn Val Leu
                340                 345                 350
Glu Leu Met Gln Lys His Ile His Ser Pro Glu Val Ala Glu Ser Gly
                355                 360                 365
Cys Lys Met Leu Asn His Leu Phe Glu Gly Ser Asn Thr Ser Leu Asp
                370                 375                 380
Ile Met Ala Ala Val Val Pro Lys Ile Leu Thr Val Met Lys Arg His
385                 390                 395                 400
Glu Thr Ser Leu
```

<210> SEQ ID NO 67
<211> LENGTH: 10
<212> TYPE: PRT
<213> ORGANISM: Artificial
<220> FEATURE:
<223> OTHER INFORMATION: Recombinant protein

<400> SEQUENCE: 67

```
Trp Trp Lys Phe Tyr Thr Leu Arg Arg Ala
1               5                   10
```

<210> SEQ ID NO 68
<211> LENGTH: 21
<212> TYPE: PRT
<213> ORGANISM: Artificial Sequence
<220> FEATURE:
<223> OTHER INFORMATION: Recombinant protein
<220> FEATURE:
<221> NAME/KEY: VARIANT
<222> LOCATION: (9)..(9)
<223> OTHER INFORMATION: Ser or Thr

```
<400> SEQUENCE: 68

Arg Leu Gly Arg Asp Lys Tyr Lys Xaa Leu Arg Gln Ile Arg Gln Gly
1               5                   10                  15

Asn Thr Lys Gln Arg
            20

<210> SEQ ID NO 69
<211> LENGTH: 2527
<212> TYPE: PRT
<213> ORGANISM: Homo sapiens

<400> SEQUENCE: 69

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Ser Thr Asn Phe Lys Asp Glu Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335
```

```
Glu Asn Asp Asp Glu Gly Glu Asp Lys Leu Phe Trp Leu Glu Ala
            340                 345                 350

Cys Tyr Lys Ala Leu Thr Trp His Arg Lys Asn Lys His Val Gln Glu
            355                 360                 365

Ala Ala Cys Trp Ala Leu Asn Asn Leu Leu Met Tyr Gln Asn Ser Leu
            370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
            435                 440                 445

Met Gln Lys His Ile His Ser Pro Glu Val Ala Glu Ser Gly Cys Lys
            450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
            485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
            515                 520                 525

Lys Leu Asn Met Val Lys Lys Gln Cys Phe Lys Asn Asp Ile His Lys
            530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
            565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
            595                 600                 605

Leu Ile Gly Tyr Leu Ile Thr Lys Lys Asn Val Phe Ile Gly Thr Gly
610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
            645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
            675                 680                 685

Gln Gln Phe Leu Asn Leu Cys Cys Lys Cys Phe Ala Lys Val Ala Met
            690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
            755                 760                 765
```

```
Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
                820                 825                 830

Thr Asn Ile Ala Ser Thr Leu Ala Arg Met Val Ile Arg Tyr Gln Met
                835                 840                 845

Lys Ser Ala Val Glu Glu Gly Thr Ala Ser Gly Ser Asp Gly Asn Phe
    850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Ser Asn Ser Ile Ser
                900                 905                 910

Val Gly Glu Phe Tyr Arg Asp Ala Val Leu Gln Arg Cys Ser Pro Asn
                915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
                980                 985                 990

Glu Leu Arg Asp Ile Asp Ala Leu  Ser Gln Lys Cys Cys  Ile Ser Val
                995                 1000                1005

His Leu  Glu His Leu Glu Lys  Leu Glu Leu His Gln  Asn Ala Leu
    1010                1015                1020

Thr Ser  Phe Pro Gln Gln Leu  Cys Glu Thr Leu Lys  Ser Leu Thr
    1025                1030                1035

His Leu  Asp Leu His Ser Asn  Lys Phe Thr Ser Phe  Pro Ser Tyr
    1040                1045                1050

Leu Leu  Lys Met Ser Cys Ile  Ala Asn Leu Asp Val  Ser Arg Asn
    1055                1060                1065

Asp Ile  Gly Pro Ser Val Val  Leu Asp Pro Thr Val  Lys Cys Pro
    1070                1075                1080

Thr Leu  Lys Gln Phe Asn Leu  Ser Tyr Asn Gln Leu  Ser Phe Val
    1085                1090                1095

Pro Glu  Asn Leu Thr Asp Val  Val Glu Lys Leu Glu  Gln Leu Ile
    1100                1105                1110

Leu Glu  Gly Asn Lys Ile Ser  Gly Ile Cys Ser Pro  Leu Arg Leu
    1115                1120                1125

Lys Glu  Leu Lys Ile Leu Asn  Leu Ser Lys Asn His  Ile Ser Ser
    1130                1135                1140

Leu Ser  Glu Asn Phe Leu Glu  Ala Cys Pro Lys Val  Glu Ser Phe
    1145                1150                1155

Ser Ala  Arg Met Asn Phe Leu  Ala Ala Met Pro Phe  Leu Pro Pro
    1160                1165                1170

Ser Met  Thr Ile Leu Lys Leu  Ser Gln Asn Lys Phe  Ser Cys Ile
```

-continued

```
        1175                1180                1185

Pro Glu Ala Ile Leu Asn Leu Pro His Leu Arg Ser Leu Asp Met
        1190                1195                1200

Ser Ser Asn Asp Ile Gln Tyr Leu Pro Gly Pro Ala His Trp Lys
        1205                1210                1215

Ser Leu Asn Leu Arg Glu Leu Leu Phe Ser His Asn Gln Ile Ser
        1220                1225                1230

Ile Leu Asp Leu Ser Glu Lys Ala Tyr Leu Trp Ser Arg Val Glu
        1235                1240                1245

Lys Leu His Leu Ser His Asn Lys Leu Lys Glu Ile Pro Pro Glu
        1250                1255                1260

Ile Gly Cys Leu Glu Asn Leu Thr Ser Leu Asp Val Ser Tyr Asn
        1265                1270                1275

Leu Glu Leu Arg Ser Phe Pro Asn Glu Met Gly Lys Leu Ser Lys
        1280                1285                1290

Ile Trp Asp Leu Pro Leu Asp Glu Leu His Leu Asn Phe Asp Phe
        1295                1300                1305

Lys His Ile Gly Cys Lys Ala Lys Asp Ile Ile Arg Phe Leu Gln
        1310                1315                1320

Gln Arg Leu Lys Lys Ala Val Pro Tyr Asn Arg Met Lys Leu Met
        1325                1330                1335

Ile Val Gly Asn Thr Gly Ser Gly Lys Thr Thr Leu Leu Gln Gln
        1340                1345                1350

Leu Met Lys Thr Lys Lys Ser Asp Leu Gly Met Gln Ser Ala Thr
        1355                1360                1365

Val Gly Ile Asp Val Lys Asp Trp Pro Ile Gln Ile Arg Asp Lys
        1370                1375                1380

Arg Lys Arg Asp Leu Val Leu Asn Val Trp Asp Phe Ala Gly Arg
        1385                1390                1395

Glu Glu Phe Tyr Ser Thr His Pro His Phe Met Thr Gln Arg Ala
        1400                1405                1410

Leu Tyr Leu Ala Val Tyr Asp Leu Ser Lys Gly Gln Ala Glu Val
        1415                1420                1425

Asp Ala Met Lys Pro Trp Leu Phe Asn Ile Lys Ala Arg Ala Ser
        1430                1435                1440

Ser Ser Pro Val Ile Leu Val Gly Thr His Leu Asp Val Ser Asp
        1445                1450                1455

Glu Lys Gln Arg Lys Ala Cys Met Ser Lys Ile Thr Lys Glu Leu
        1460                1465                1470

Leu Asn Lys Arg Gly Phe Pro Ala Ile Arg Asp Tyr His Phe Val
        1475                1480                1485

Asn Ala Thr Glu Glu Ser Asp Ala Leu Ala Lys Leu Arg Lys Thr
        1490                1495                1500

Ile Ile Asn Glu Ser Leu Asn Phe Lys Ile Arg Asp Gln Leu Val
        1505                1510                1515

Val Gly Gln Leu Ile Pro Asp Cys Tyr Val Glu Leu Glu Lys Ile
        1520                1525                1530

Ile Leu Ser Glu Arg Lys Asn Val Pro Ile Glu Phe Pro Val Ile
        1535                1540                1545

Asp Arg Lys Arg Leu Leu Gln Leu Val Arg Glu Asn Gln Leu Gln
        1550                1555                1560

Leu Asp Glu Asn Glu Leu Pro His Ala Val His Phe Leu Asn Glu
        1565                1570                1575
```

| | | | | | | | | | | | |
|---|---|---|---|---|---|---|---|---|---|---|---|
|Ser|Gly|Val|Leu|Leu|His|Phe|Gln|Asp|Pro|Ala|Leu|Gln|Leu|Ser|
| |1580| | | |1585| | | |1590| | | | | |

Ser Gly Val Leu Leu His Phe Gln Asp Pro Ala Leu Gln Leu Ser
        1580            1585            1590

Asp Leu Tyr Phe Val Glu Pro Lys Trp Leu Cys Lys Ile Met Ala
        1595            1600            1605

Gln Ile Leu Thr Val Lys Val Glu Gly Cys Pro Lys His Pro Lys
        1610            1615            1620

Gly Ile Ile Ser Arg Arg Asp Val Glu Lys Phe Leu Ser Lys Lys
        1625            1630            1635

Arg Lys Phe Pro Lys Asn Tyr Met Ser Gln Tyr Phe Lys Leu Leu
        1640            1645            1650

Glu Lys Phe Gln Ile Ala Leu Pro Ile Gly Glu Glu Tyr Leu Leu
        1655            1660            1665

Val Pro Ser Ser Leu Ser Asp His Arg Pro Val Ile Glu Leu Pro
        1670            1675            1680

His Cys Glu Asn Ser Glu Ile Ile Ile Arg Leu Tyr Glu Met Pro
        1685            1690            1695

Tyr Phe Pro Met Gly Phe Trp Ser Arg Leu Ile Asn Arg Leu Leu
        1700            1705            1710

Glu Ile Ser Pro Tyr Met Leu Ser Gly Arg Glu Arg Ala Leu Arg
        1715            1720            1725

Pro Asn Arg Met Tyr Trp Arg Gln Gly Ile Tyr Leu Asn Trp Ser
        1730            1735            1740

Pro Glu Ala Tyr Cys Leu Val Gly Ser Glu Val Leu Asp Asn His
        1745            1750            1755

Pro Glu Ser Phe Leu Lys Ile Thr Val Pro Ser Cys Arg Lys Gly
        1760            1765            1770

Cys Ile Leu Leu Gly Gln Val Val Asp His Ile Asp Ser Leu Met
        1775            1780            1785

Glu Glu Trp Phe Pro Gly Leu Leu Glu Ile Asp Ile Cys Gly Glu
        1790            1795            1800

Gly Glu Thr Leu Leu Lys Lys Trp Ala Leu Tyr Ser Phe Asn Asp
        1805            1810            1815

Gly Glu Glu His Gln Lys Ile Leu Leu Asp Asp Leu Met Lys Lys
        1820            1825            1830

Ala Glu Glu Gly Asp Leu Leu Val Asn Pro Asp Gln Pro Arg Leu
        1835            1840            1845

Thr Ile Pro Ile Ser Gln Ile Ala Pro Asp Leu Ile Leu Ala Asp
        1850            1855            1860

Leu Pro Arg Asn Ile Met Leu Asn Asn Asp Glu Leu Glu Phe Glu
        1865            1870            1875

Gln Ala Pro Glu Phe Leu Leu Gly Asp Gly Ser Phe Gly Ser Val
        1880            1885            1890

Tyr Arg Ala Ala Tyr Glu Gly Glu Glu Val Ala Val Lys Ile Phe
        1895            1900            1905

Asn Lys His Thr Ser Leu Arg Leu Leu Arg Gln Glu Leu Val Val
        1910            1915            1920

Leu Cys His Leu His His Pro Ser Leu Ile Ser Leu Leu Ala Ala
        1925            1930            1935

Gly Ile Arg Pro Arg Met Leu Val Met Glu Leu Ala Ser Lys Gly
        1940            1945            1950

Ser Leu Asp Arg Leu Leu Gln Gln Asp Lys Ala Ser Leu Thr Arg
        1955            1960            1965

Thr Leu Gln His Arg Ile Ala Leu His Val Ala Asp Gly Leu Arg
        1970            1975            1980

-continued

```
Tyr Leu His Ser Ala Met Ile Ile Tyr Arg Asp Leu Lys Pro His
    1985            1990            1995

Asn Val Leu Leu Phe Thr Leu Tyr Pro Asn Ala Ala Ile Ile Ala
    2000            2005            2010

Lys Ile Ala Asp Tyr Gly Ile Ala Gln Tyr Cys Cys Arg Met Gly
    2015            2020            2025

Ile Lys Thr Ser Glu Gly Thr Pro Gly Phe Arg Ala Pro Glu Val
    2030            2035            2040

Ala Arg Gly Asn Val Ile Tyr Asn Gln Gln Ala Asp Val Tyr Ser
    2045            2050            2055

Phe Gly Leu Leu Leu Tyr Asp Ile Leu Thr Thr Gly Gly Arg Ile
    2060            2065            2070

Val Glu Gly Leu Lys Phe Pro Asn Glu Phe Asp Glu Leu Glu Ile
    2075            2080            2085

Gln Gly Lys Leu Pro Asp Pro Val Lys Glu Tyr Gly Cys Ala Pro
    2090            2095            2100

Trp Pro Met Val Glu Lys Leu Ile Lys Gln Cys Leu Lys Glu Asn
    2105            2110            2115

Pro Gln Glu Arg Pro Thr Ser Ala Gln Val Phe Asp Ile Leu Asn
    2120            2125            2130

Ser Ala Glu Leu Val Cys Leu Thr Arg Arg Ile Leu Leu Pro Lys
    2135            2140            2145

Asn Val Ile Val Glu Cys Met Val Ala Thr His His Asn Ser Arg
    2150            2155            2160

Asn Ala Ser Ile Trp Leu Gly Cys Gly His Thr Asp Arg Gly Gln
    2165            2170            2175

Leu Ser Phe Leu Asp Leu Asn Thr Glu Gly Tyr Thr Ser Glu Glu
    2180            2185            2190

Val Ala Asp Ser Arg Ile Leu Cys Leu Ala Leu Val His Leu Pro
    2195            2200            2205

Val Glu Lys Glu Ser Trp Ile Val Ser Gly Thr Gln Ser Gly Thr
    2210            2215            2220

Leu Leu Val Ile Asn Thr Glu Asp Gly Lys Lys Arg His Thr Leu
    2225            2230            2235

Glu Lys Met Thr Asp Ser Val Thr Cys Leu Tyr Cys Asn Ser Phe
    2240            2245            2250

Ser Lys Gln Ser Lys Gln Lys Asn Phe Leu Leu Val Gly Thr Ala
    2255            2260            2265

Asp Gly Lys Leu Ala Ile Phe Glu Asp Lys Thr Val Lys Leu Lys
    2270            2275            2280

Gly Ala Ala Pro Leu Lys Ile Leu Asn Ile Gly Asn Val Ser Thr
    2285            2290            2295

Pro Leu Met Cys Leu Ser Glu Ser Thr Asn Ser Thr Glu Arg Asn
    2300            2305            2310

Val Met Trp Gly Gly Cys Gly Thr Lys Ile Phe Ser Phe Ser Asn
    2315            2320            2325

Asp Phe Thr Ile Gln Lys Leu Ile Glu Thr Arg Thr Ser Gln Leu
    2330            2335            2340

Phe Ser Tyr Ala Ala Phe Ser Asp Ser Asn Ile Ile Thr Val Val
    2345            2350            2355

Val Asp Thr Ala Leu Tyr Ile Ala Lys Gln Asn Ser Pro Val Val
    2360            2365            2370

Glu Val Trp Asp Lys Lys Thr Glu Lys Leu Cys Gly Leu Ile Asp
```

```
                2375                2380                2385
Cys Val His Phe Leu Arg Glu Val Met Val Lys Glu Asn Lys Glu
        2390                2395                2400

Ser Lys His Lys Met Ser Tyr Ser Gly Arg Val Lys Thr Leu Cys
        2405                2410                2415

Leu Gln Lys Asn Thr Ala Leu Trp Ile Gly Thr Gly Gly His
        2420                2425                2430

Ile Leu Leu Leu Asp Leu Ser Thr Arg Arg Leu Ile Arg Val Ile
        2435                2440                2445

Tyr Asn Phe Cys Asn Ser Val Arg Val Met Met Thr Ala Gln Leu
        2450                2455                2460

Gly Ser Leu Lys Asn Val Met Leu Val Leu Gly Tyr Asn Arg Lys
        2465                2470                2475

Asn Thr Glu Gly Thr Gln Lys Gln Lys Glu Ile Gln Ser Cys Leu
        2480                2485                2490

Thr Val Trp Asp Ile Asn Leu Pro His Glu Val Gln Asn Leu Glu
        2495                2500                2505

Lys His Ile Glu Val Arg Lys Glu Leu Ala Glu Lys Met Arg Arg
        2510                2515                2520

Thr Ser Val Glu
        2525

<210> SEQ ID NO 70
<211> LENGTH: 586
<212> TYPE: PRT
<213> ORGANISM: Homo sapiens

<400> SEQUENCE: 70

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45

Tyr Val Asp Asn Lys Gly Phe Pro Thr Trp Leu Lys Leu Asp Lys Lys
    50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
        115                 120                 125

Ala Val Gln Ala Lys Phe Gly Asp Tyr Asn Lys Glu Val His Lys Ser
    130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Asp Asn Ala Met Leu Glu Tyr Leu
            180                 185                 190

Lys Ile Ala Gln Asp Leu Glu Met Tyr Gly Ile Asn Tyr Phe Glu Ile
        195                 200                 205

Lys Asn Lys Lys Gly Thr Asp Leu Trp Leu Gly Val Asp Ala Leu Gly
```

```
            210             215             220
Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
            245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Gln Leu Cys Met Gly Asn His
            275                 280                 285

Glu Leu Tyr Met Arg Arg Lys Pro Asp Thr Ile Glu Val Gln Gln
        290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Arg Glu Thr Val Glu Arg Glu
                325                 330                 335

Lys Glu Gln Met Met Arg Glu Lys Glu Glu Leu Met Leu Arg Leu Gln
                340                 345                 350

Asp Tyr Glu Glu Lys Thr Lys Lys Ala Glu Arg Glu Leu Ser Glu Gln
                355                 360                 365

Ile Gln Arg Ala Leu Gln Leu Glu Glu Glu Arg Lys Arg Ala Gln Glu
        370                 375                 380

Glu Ala Glu Arg Leu Glu Ala Asp Arg Met Ala Ala Leu Arg Ala Lys
385                 390                 395                 400

Glu Glu Leu Glu Arg Gln Ala Val Asp Gln Ile Lys Ser Gln Glu Gln
                405                 410                 415

Leu Ala Ala Glu Leu Ala Glu Tyr Thr Ala Lys Ile Ala Leu Leu Glu
                420                 425                 430

Glu Ala Arg Arg Arg Lys Glu Asp Glu Val Glu Glu Trp Gln His Arg
                435                 440                 445

Ala Lys Glu Ala Gln Asp Asp Leu Val Lys Thr Lys Glu Glu Leu His
        450                 455                 460

Leu Val Met Thr Ala Pro Pro Pro Pro Pro Pro Val Tyr Glu Pro
465                 470                 475                 480

Val Ser Tyr His Val Gln Glu Ser Leu Gln Asp Glu Gly Ala Glu Pro
                485                 490                 495

Thr Gly Tyr Ser Ala Glu Leu Ser Ser Glu Gly Ile Arg Asp Asp Arg
                500                 505                 510

Asn Glu Glu Lys Arg Ile Thr Glu Ala Glu Lys Asn Glu Arg Val Gln
                515                 520                 525

Arg Gln Leu Leu Thr Leu Ser Ser Glu Leu Ser Gln Ala Arg Asp Glu
        530                 535                 540

Asn Lys Arg Thr His Asn Asp Ile Ile His Asn Glu Asn Met Arg Gln
545                 550                 555                 560

Gly Arg Asp Lys Tyr Lys Thr Leu Arg Gln Ile Arg Gln Gly Asn Thr
                565                 570                 575

Lys Gln Arg Ile Asp Glu Phe Glu Ala Leu
                580                 585
```